(12) United States Patent
Breakefield et al.

(10) Patent No.: US 11,958,887 B2
(45) Date of Patent: Apr. 16, 2024

(54) GENE THERAPY FOR TUBEROUS SCLEROSIS

(71) Applicant: The General Hospital Corporation, Boston, MA (US)

(72) Inventors: Xandra Breakefield, Newton, MA (US); Casey Maguire, Arlington, MA (US); Shilpa Prabhakar, Braintree, MA (US); David Yellen, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 770 days.

(21) Appl. No.: 16/613,907

(22) PCT Filed: May 17, 2018

(86) PCT No.: PCT/US2018/033247
§ 371 (c)(1),
(2) Date: Nov. 15, 2019

(87) PCT Pub. No.: WO2018/213618
PCT Pub. Date: Nov. 22, 2018

(65) Prior Publication Data
US 2020/0079824 A1    Mar. 12, 2020

Related U.S. Application Data

(60) Provisional application No. 62/507,358, filed on May 17, 2017.

(51) Int. Cl.
*A61P 35/00* (2006.01)
*A61K 9/00* (2006.01)
(Continued)

(52) U.S. Cl.
CPC ........ *C07K 14/4705* (2013.01); *A61K 9/0019* (2013.01); *A61K 9/007* (2013.01);
(Continued)

(58) Field of Classification Search
CPC .... A61K 38/00; A61K 38/1709; A61K 48/00; A61K 48/005; A61P 35/00; C12N 7/00;
(Continued)

(56) References Cited

U.S. PATENT DOCUMENTS 6,884,419 B1 *  4/2005  Yokoi .................. C07K 14/524
                                                        424/192.1
2006/0239966 A1  10/2006  Tornoe et al.
(Continued)

FOREIGN PATENT DOCUMENTS

| JP | 2005-535332 A | 11/2005 |
|---|---|---|
| WO | WO-2004014222 A2 | 2/2004 |
| WO | WO-2011/020118 A1 | 2/2011 |

OTHER PUBLICATIONS

Leiden Open Variation Database (LOVD3), Global Variome shared LOVD, https://databases.lovd.nl/shared/genes/TSC2; last accessed Sep. 28, 2021.*

(Continued)

*Primary Examiner* — Kevin K Hill
(74) *Attorney, Agent, or Firm* — Clark & Elbing LLP

(57) ABSTRACT

The invention provides compositions and methods for treating tuberous sclerosis complex (TSC). In particular, provided are condensed tuberins (cTuberins), cTuberin nucleic acids, and recombinant adeno-associated viruses (rAAVs) carrying a cTuberin nucleic acid for treating a patient with TSC.

21 Claims, 15 Drawing Sheets

Specification includes a Sequence Listing.

(51) Int. Cl.
| | |
|---|---|
| A61K 31/436 | (2006.01) |
| A61K 38/00 | (2006.01) |
| A61K 38/17 | (2006.01) |
| A61K 48/00 | (2006.01) |
| C07K 14/47 | (2006.01) |
| C12N 7/00 | (2006.01) |
| C12N 15/86 | (2006.01) |

(52) U.S. Cl.
CPC .......... *A61K 9/0085* (2013.01); *A61K 31/436* (2013.01); *A61K 38/1709* (2013.01); *A61K 48/005* (2013.01); *A61P 35/00* (2018.01); *C12N 7/00* (2013.01); *C12N 15/86* (2013.01); *C12N 2750/14143* (2013.01); *C12N 2750/14171* (2013.01); *C12N 2830/50* (2013.01)

(58) Field of Classification Search
CPC .. C12N 15/86; C12N 15/864; C12N 15/8645; C12N 2750/14171
See application file for complete search history.

(56) References Cited

U.S. PATENT DOCUMENTS

| | | |
|---|---|---|
| 2009/0143288 A1 | 6/2009 | Duefel et al. |
| 2012/0252877 A1* | 10/2012 | Lo .................... A61P 25/00 514/44 R |
| 2014/0107189 A1 | 4/2014 | Bancel et al. |
| 2016/0009785 A1 | 1/2016 | Lipson et al. |

OTHER PUBLICATIONS

Niida et al, Human Mutation 14: 412-422, 1999.*
He et al, Child's Nervous System 36: 1827-1830, 2020.*
Inoki et al, Nature Cell Biology 4: 648-657, 2002.*
GenBank NG_005895; Jan. 31, 2016.*
Ward et al, Blood 117(3): 798-807, 2011.*
Babchia et al, Invest. Ophthalmol. & Vis. Sci. 51(1): 421-429, 2010.*
Ji et al, Journal of Cancer 8(4): 555-562, doi: 10.7150/jca.17205; 8 pages, published online Feb. 11, 2017.*
Guvakova et al, Cell Movement: New Research Trends, Chapter VI, pp. 187-207, 2009, editors T. Abreau and G. Silva, Nova Science Publishers, Inc, ISBN: 978-1-60692-570-6.*
Xiao et al, J. Biol. Chem. 272(10): 6097-6100, 1997.*
Zech et al, J. Biol. Chem. 291(38): 20008-20020, 2016; published Sep. 16, 2016.*
GenBank XP006245971 (rat tuberin, TSC2, 2016).*
Nellist et al, Eur. J. Human Genetics 13: 59-68, 2005.*
GenBank XP027469318.1, Zalophus californianus, California sea lion, tuberin, 1747 amino acids, 2020.*
GenBank JAA04277 (Pan troglodytes, tuberous sclerosis 2, 1740 amino acids, 2012.*
Nellist et al, Human Mol. Genet. 10(25): 2889-2898, 2001.*
GenBank AAC34210, Jul. 25, 2016; *Homo sapiens* TSC2, 1784aa.*
Sabatino et al, Efficacy and Safety of Long-term Prophylaxis in Severe Hemophilia A Dogs Following Liver Gene Therapy Using AAV Vectors, Molecular Therapy 19(3): 442-449, 2011.*
Aicher et al., "Tuberin phosphorylation regulates its interaction with hamartin. Two proteins involved in tuberous sclerosis," J Biol Chem. 276(24):21017-21 (2001).
Bevan et al., "Systemic gene delivery in large species for targeting spinal cord, brain, and peripheral tissues for pediatric disorders," Mol Ther. 19(11):1971-80 (2011).
Broekman et al., "Adeno-associated virus vectors serotyped with AAV8 capsid are more efficient than AAV-1 or -2 serotypes for widespread gene delivery to the neonatal mouse brain," Neuroscience. 138(2):501-10 (2006).
Cai et al., "Activity of TSC2 is inhibited by AKT-mediated phosphorylation and membrane partitioning," J Cell Biol. 173(2):279-89 (2006).
Chapman et al., "mTOR signaling, Tregs and immune modulation," Immunotherapy. 6(12):1295-311 (2014).
Duque et al., "Intravenous administration of self-complementary AAV9 enables transgene delivery to adult motor neurons," Mol Ther. 17(7):1187-96 (2009).
Foust et al., "Intravascular AAV9 preferentially targets neonatal neurons and adult astrocytes," available in PMC Jul. 2, 2010, published in final edited form as: 27(1):59-65 (2009) (15 pages).
Fu et al., "Correction of neurological disease of mucopolysaccharidosis IIIB in adult mice by rAAV9 trans-blood-brain barrier gene delivery," Mol Ther. 19(6):1025-33 (2011).
Gaubitz et al., "TORC2 Structure and Function," Trends Biochem Sci. 41(6):532-545 (2016).
Gray et al., "Optimizing promoters for recombinant adeno-associated virus-mediated gene expression in the peripheral and central nervous system using self-complementary vectors," Hum Gene Ther. 22(9):1143-53 (2011).
Gray et al., "Preclinical differences of intravascular AAV9 delivery to neurons and glia: a comparative study of adult mice and nonhuman primates," Mol Ther. 19(6):1058-69 (2011).
Henske et al., "Tuberous sclerosis complex," Nat Rev Dis Primers. 2:16035 (2016).
Hong et al., "mTOR-raptor binds and activates SGK1 to regulate p27 phosphorylation," Mol Cell. 30(6):701-11 (2008).
Huang et al., "The TSC1-TSC2 complex is required for proper activation of mTOR complex 2," Mol Cell Biol. 28(12):4104-15 (2008).
Huang et al., "The TSC1-TSC2 complex: a molecular switchboard controlling cell growth," available in PMC Aug. 31, 2009, published in final edited form as: Biochem J. 412(2)L179-90 (2008).
Inoki et al., "TSC2 is phosphorylated and inhibited by Akt and suppresses mTOR signalling," Nat Cell Biol. 4(9):648-57 (2002).
International Preliminary Report on Patentability for International Application No. PCT/US2018/033247, dated Nov. 19, 2019 (14 pages).
International Search Report and Written Opinion for International Application No. PCT/US18/33247, dated Oct. 12, 2018 (23 pages).
Jeong et al., "mTOR Inhibitors in Children: Current Indications and Future Directions in Neurology," Curr Neurol Neurosci Rep. 16(12):102 (2016) (8 pages).
Lesma et al., "Development of a lymphangioleiomyomatosis model by endonasal administration of human TSC2-/- smooth muscle cells in mice," Am J Pathol. 181(3):947-60 (2012).
Momose et al., "Identification of the coding sequences responsible for Tsc2-mediated tumor suppression using a transgenic rat system," Hum Mol Genet. 11(24):2997-3006 (2002).
Nellist et al., "TSC2 missense mutations inhibit tuberin phosphorylation and prevent formation of the tuberin-hamartin complex," Hum Mol Genet. 10(25):2889-98 (2001).
Onda et al., "Tsc2(+/−) mice develop tumors in multiple sites that express gelsolin and are influenced by genetic background," J Clin Invest. 104(6):687-95 (1999).
Prabhakar et al., "196. AAV-Mediated Gene Replacement Therapy in Mouse Model of Tuberous Sclerosis," Abstracts of the ASGCT 18th Annual Meeting. Mol Ther. 23(Suppl. 1):S78 (2015) (1 page) (Abstract Only).
Prabhakar et al., "Long-Term Therapeutic Efficacy of Intravenous AAV-Mediated Hamartin Replacement in Mouse Model of Tuberous Sclerosis Type 1," Mol Ther Methods Clin Dev. 15:18-26 (2019).
Prabhakar et al., "Stochastic model of Tsc1 lesions in mouse brain," PLOS One 8(5):e64224 (2013) (12 pages).
Prabhakar et al., "Survival benefit and phenotypic improvement by hamartin gene therapy in a tuberous sclerosis mouse brain model," available in PMC Oct. 19, 2016, published in final edited form as: Neurobiol Dis. 82:22-31 (2015).
Rizzo et al., "An improved cyan fluorescent protein variant useful for FRET," Nat Biotechnol. 22(4):445-9 (2004).
Sena-Esteves et al., "Optimized large-scale production of high titer lentivirus vector pseudotypes," J Virol Methods. 122(2):131-9 (2004).

(56) References Cited

OTHER PUBLICATIONS

Sheth et al., "Angiographic and volumetric effects of mammalian target of rapamycin inhibitors on angiomyolipomas in tuberous sclerosis," World J Radiol. 8(3):308-15 (2016).

Tsai et al., "Prenatal rapamycin results in early and late behavioral abnormalities in wildtype C57BL/6 mice," available in PMC Jan. 1, 2014, published in final edited form as: Behav Genet. 43(1):51-9 (2013).

Yang et al., "Global CNS transduction of adult mice by intravenously delivered rAAVrh.8 and rAAVrh.10 and nonhuman primates by rAAVrh.10," Mol Ther. 22(7):1299-1309 (2014).

Yardeni et al., "Retro-orbital injections in mice," available in PMC Aug. 19, 2011, published in final edited form as: Lab Anim (NY). 40(5):155-60 (2011).

Yu et al., "Estradiol and tamoxifen stimulate LAM-associated angiomyolipoma cell growth and activate both genomic and nongenomic signaling pathway," Am J Physiol Lung Cell Mol Physiol. 286(4):L694-700 (2004).

Zhang et al., "Vigabatrin inhibits seizures and mTOR pathway activation in a mouse model of tuberous sclerosis complex," PLOS One 8(2):e57445 (2013) (8 pages).

Choudhury et al., "Viral vectors for therapy of neurologic diseases," available in PMC May 1, 2018, published in final edited form as: Neuropharmacology. 120:63-80 (Jul. 2017) (44 pages).

Gernoux et al., "Regulatory and Exhausted T Cell Responses to AAV Capsid," Hum Gene Ther. 28(4):338-349 (Apr. 2017).

Randle, "Tuberous Sclerosis Complex: A Review," Pediatr Ann. 46(4):e166-e171 (Apr. 2017).

Rosset et al., "TSC1 and TSC2 gene mutations and their implications for treatment in Tuberous Sclerosis Complex: a review," Genet Mol Biol. 40(1):69-79 (Jan.-Mar. 2017).

Wang et al., "Brain Development and Akt Signaling: the Crossroads of Signaling Pathway and Neurodevelopmental Diseases," J Mol Neurosci. 61(3):379-384 (Mar. 2017).

Hudry et al. "Exosome-associated AAV vector as a robust and convenient neuroscience tool," Gene Ther. 23(4):380-392 (Feb. 2016).

Manning et al., "Identification of the tuberous sclerosis complex-2 tumor suppressor gene product tuberin as a target of the phosphoinositide 3-kinase/akt pathway," Mol Cell. 10(1):151-62 (2002).

\* cited by examiner

FIG. 1A

MAKPTSKDSGLKEKFKILLGLGTPRPNPRSAEGKQTEFITTAEILRELSMECGLN

NRIRMIGQICEVAKTKKFEEHAVEALWKAVADLLQPERPLEARHAVLALLKAIVQGQGER

LGVLRALFFKVIKDYPSNEDLHERLEVFKALTDNGRHITYLEEELADFVLQWMDVGLSSE

FLLVLVNLVKFNSCYLDEYIARMVQMICLLCVRTASSVDIEVSLQVLDAVVCYNCLPAES

LPLFIVTLCRTIINVKELCEPCWKLMRNLLGTHLGHSAIYNMCHLMEDRAYMEDAPLLRGA

VFFVGMALWGAHRLYSLRNSPTSVLPSFYQAMACPNEVVSYEIVLSITTRLIKKYRKELQV

VAWDILLNIIERLLQQLQTLDSPELRTIVHDLLTTVEELCDQNEFHGSQERYFELVERCA

DQRPESSLLNLISYRAQSIHPAKDGWIQNLQALMESGGGSGGGSGGGGSGGGKPILLPNES

QSFERSVQLLDQIPSYDTHKIAVLYVGEGQSNSELAILSNEHGSYRYTEFLTGLRLIEL

KDCQPDKVYLGGLDVCGEDGQFTYCWHDDIMQAVFHIATLMPTKDVDKHRCDKKRHLGND

FVSIVYNDSGEDFKLGTIKGQFNFVHVIVTPLDYECNLVSLQCRKDMEGLVDTSVAKIVS

DRNLPFVARQMALHANMASQVHHSRSNPTDIYPSKWIARLRHIKRLRQRICEEAAYSNPS

LPLVHPPSHSKAPAQTPAEPTPGYEVGQRKRLISSVEDFTEFV (SEQ ID NO: 1)

FIG. 1B

GCTAGCACTAGTaccatggcgaaccgaccagcgaagataccggcctgaaagaaaaattctgctggcctgcatccccgcgc
ccgaacccgcgcggcggaagccgaccagacagcaaacagttattaccgcgaactcctgcgcgaactgaatgccgctgaac
aaccgcattcgcattgattgccagatttgcgaagtgcgaagaacatgcggttgcgaagcgctgttggaagcaggcgaacgcggtg
gcgatctgctgcagcgcggaagcgcccatgcgcgtgctgctgaaagcgcctgctgcaggcgaagtgtttaaagcg
ctgggcgtgctgcgcgcgtgtttttaaagattatcctagctggaagaagcaacgcctgcatgaacgaagtgcttaaagcg
ctaccggataacgcgctggttgctgttaacctgtgaaattaacagctgcgatctggatgcgcaggttgctgcaagtgctg
tttctgctgtcgtgctgccgcgagcacagcagccctgtgaaacgtgcgaacagtgccgtggtgcctgataatattgccgcagttgctgc
tgccgctgtttattgtgacctgcgatttgcgcacatgtcgaacctgtgaaactgcagaacctgcgcgcggcgcg
ctgctctggggccatagcgcgtgcgtgaagtgagtgacatacgcctgtgcatgaacggggcgcaacagttccgacgcccgattaaaaaatatcgcgaccggagccagaactgcagtg
accatctgtttttggccatagcgcgtgcgtggcaatttatgaacggggcgcaacagttccgacgcccgattaaaaatatcgcaaccgaggccagaactgcagtg
gtgctggatatcctggtgaaagaacgctatttgaacgcctatatagcctgcattaccgagagcagagccacgctattgaacagctatttcag
gtggcgtgggatatctgctgaacattattgaacgctatatagcctgcattaccgagagcagagccagctattgaacagctattcgcg
gatctgctgaccagccggaaagagagcctgtgaaaccctgattagccggtctgcttgcgcgatatcatccggcagagagatggtgaacctg
gtcagcgcgctgatgaaTCTGGGGGTAGCGGCGGAGAGGGTCAGGGGCCAGTGACCGAGATCCGAGACTGCTGGATCAGATCCGAGCTATGCTGCTGATGAACGAAAGCC
cagagctttgaacgcagctgctgcagcaacaacatgcggcctggtcagctctgagccgaatatgcgggcgcctgctgggccgctgattgaactg
agcaacagctttgccaacgaactgcggcgatataaagtgtatctgggcgaagatgcccagttaacctattaccgcagttgctgctgatgatatt
aaagattgcccaggcggtgtttcatattgtgtataacgatgcaactctgctgaagaacacatcgtcgatctcgatctgggcaacgat
atgcaggcggttgtgcattgtgtataacgatgcaactctgctgtaagcgcgtgattttaaacttgctatcgcatgtgcctgctggat
tttgtgagcattgcgtataacgctgtgaaccttgcggcgaatgtgcagccgcaagatggcgagccgcaggtgcattaaagcgcagtgtgagc
cgcctgaacctgattcaacctgcgaaccttgcggcgcattgccctggctgagccgcaaacgccgcgaaccgccgataccccgaaccgagc
gatcgcaacatatgcgtttgtggcccgagcctgaccgcctgaaagcgcctctggctgattgcgcgcctatcatagccgcagtatagccgag
atttatccgagcaaatggcgatttccgagccctgctgcgccatagccgagccctgaaaagccccggagccccgaacgctatgaagtgggccagccgaga
cgcctgattagcagcgtggaagattttaccgattgtaccgattttgttaccgattttgtTAGGCGCCGCCTCGAG (SEQ ID NO: 5)

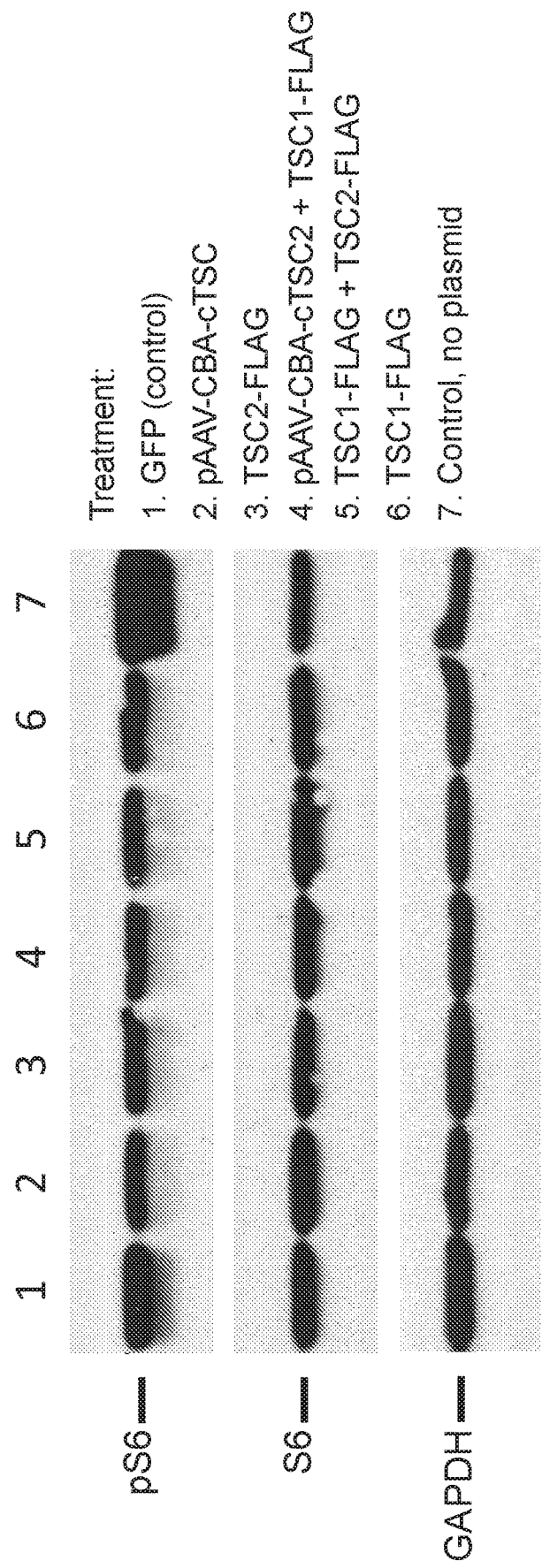

Normal, control, non-injected brain

TSC2 floxed, Cre @ P3- 1 μl/ventricle, sacrificed at 27 days

Tsc2, cTuberin injected

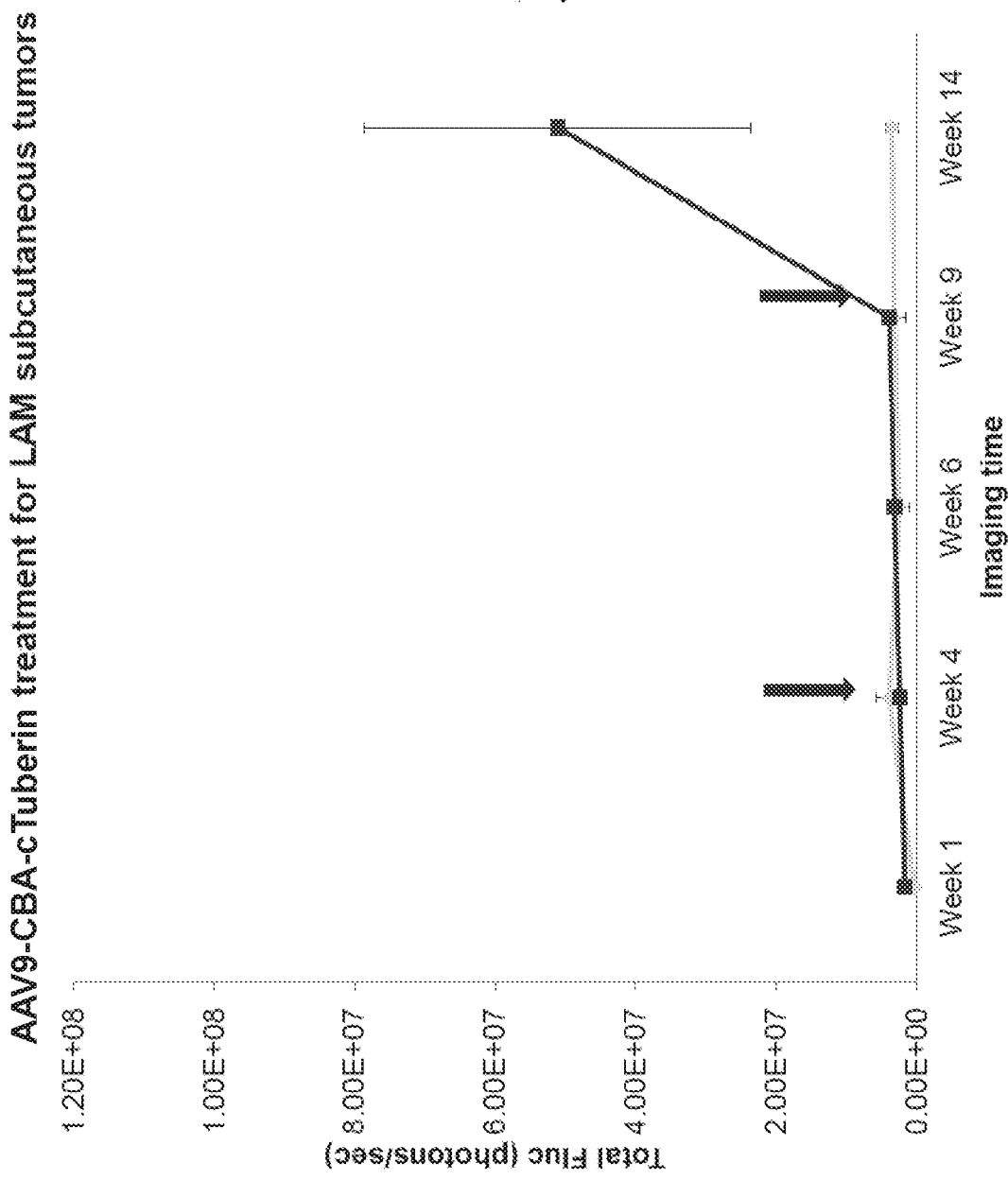

SEQUENCE LISTING

```
<160> NUMBER OF SEQ ID NOS: 13

<210> SEQ ID NO 1
<211> LENGTH: 758
<212> TYPE: PRT
<213> ORGANISM: Artificial Sequence
<220> FEATURE:
<223> OTHER INFORMATION: Synthetic Construct

<400> SEQUENCE: 1

Met Ala Lys Pro Thr Ser Lys Asp Ser Gly Leu Lys Glu Lys Phe Lys
1               5                   10                  15

Ile Leu Leu Gly Leu Gly Thr Pro Arg Pro Asn Pro Arg Ser Ala Glu
            20                  25                  30

Gly Lys Gln Thr Glu Phe Ile Ile Thr Ala Glu Ile Leu Arg Glu Leu
        35                  40                  45

Ser Met Glu Cys Gly Leu Asn Asn Arg Ile Arg Met Ile Gly Gln Ile
    50                  55                  60

Cys Glu Val Ala Lys Thr Lys Lys Phe Glu Glu His Ala Val Glu Ala
65                  70                  75                  80

Leu Trp Lys Ala Val Ala Asp Leu Leu Gln Pro Glu Arg Pro Leu Glu
                85                  90                  95

Ala Arg His Ala Val Leu Ala Leu Leu Lys Ala Ile Val Gln Gly Gln
            100                 105                 110
```

```
Gly Glu Arg Leu Gly Val Leu Arg Ala Leu Phe Phe Lys Val Ile Lys
            115                 120                 125

Asp Tyr Pro Ser Asn Glu Asp Leu His Glu Arg Leu Glu Val Phe Lys
130                 135                 140

Ala Leu Thr Asp Asn Gly Arg His Ile Thr Tyr Leu Glu Glu Glu Leu
145                 150                 155                 160

Ala Asp Phe Val Leu Gln Trp Met Asp Val Gly Leu Ser Ser Glu Phe
                165                 170                 175

Leu Leu Val Leu Val Asn Leu Val Lys Phe Asn Ser Cys Tyr Leu Asp
            180                 185                 190

Glu Tyr Ile Ala Arg Met Val Gln Met Ile Cys Leu Leu Cys Val Arg
        195                 200                 205

Thr Ala Ser Ser Val Asp Ile Glu Val Ser Leu Gln Val Leu Asp Ala
210                 215                 220

Val Val Cys Tyr Asn Cys Leu Pro Ala Glu Ser Leu Pro Leu Phe Ile
225                 230                 235                 240

Val Thr Leu Cys Arg Thr Ile Asn Val Lys Glu Leu Cys Glu Pro Cys
                245                 250                 255

Trp Lys Leu Met Arg Asn Leu Leu Gly Thr His Leu Gly His Ser Ala
            260                 265                 270

Ile Tyr Asn Met Cys His Leu Met Glu Asp Arg Ala Tyr Met Glu Asp
        275                 280                 285

Ala Pro Leu Leu Arg Gly Ala Val Phe Phe Val Gly Met Ala Leu Trp
290                 295                 300

Gly Ala His Arg Leu Tyr Ser Leu Arg Asn Ser Pro Thr Ser Val Leu
305                 310                 315                 320

Pro Ser Phe Tyr Gln Ala Met Ala Cys Pro Asn Glu Val Val Ser Tyr
                325                 330                 335

Glu Ile Val Leu Ser Ile Thr Arg Leu Ile Lys Lys Tyr Arg Lys Glu
            340                 345                 350

Leu Gln Val Val Ala Trp Asp Ile Leu Leu Asn Ile Ile Glu Arg Leu
        355                 360                 365

Leu Gln Gln Leu Gln Thr Leu Asp Ser Pro Glu Leu Arg Thr Ile Val
370                 375                 380

His Asp Leu Leu Thr Thr Val Glu Glu Leu Cys Asp Gln Asn Glu Phe
385                 390                 395                 400

His Gly Ser Gln Glu Arg Tyr Phe Glu Leu Val Glu Arg Cys Ala Asp
                405                 410                 415

Gln Arg Pro Glu Ser Ser Leu Leu Asn Leu Ile Ser Tyr Arg Ala Gln
            420                 425                 430

Ser Ile His Pro Ala Lys Asp Gly Trp Ile Gln Asn Leu Gln Ala Leu
        435                 440                 445

Met Glu Ser Gly Gly Ser Gly Gly Gly Ser Gly Gly Gly Ser Gly
450                 455                 460

Gly Gly Lys Pro Ile Leu Leu Pro Asn Glu Ser Gln Ser Phe Glu Arg
465                 470                 475                 480

Ser Val Gln Leu Leu Asp Gln Ile Pro Ser Tyr Asp Thr His Lys Ile
                485                 490                 495

Ala Val Leu Tyr Val Gly Glu Gly Gln Ser Asn Ser Glu Leu Ala Ile
            500                 505                 510

Leu Ser Asn Glu His Gly Ser Tyr Arg Tyr Thr Glu Phe Leu Thr Gly
        515                 520                 525

Leu Gly Arg Leu Ile Glu Leu Lys Asp Cys Gln Pro Asp Lys Val Tyr
```

```
                530             535             540
Leu Gly Gly Leu Asp Val Cys Gly Glu Asp Gly Gln Phe Thr Tyr Cys
545                 550                 555                 560

Trp His Asp Asp Ile Met Gln Ala Val Phe His Ile Ala Thr Leu Met
                565                 570                 575

Pro Thr Lys Asp Val Asp Lys His Arg Cys Asp Lys Lys Arg His Leu
                580                 585                 590

Gly Asn Asp Phe Val Ser Ile Val Tyr Asn Asp Ser Gly Glu Asp Phe
                595                 600                 605

Lys Leu Gly Thr Ile Lys Gly Gln Phe Asn Phe Val His Val Ile Val
                610                 615                 620

Thr Pro Leu Asp Tyr Glu Cys Asn Leu Val Ser Leu Gln Cys Arg Lys
625                 630                 635                 640

Asp Met Glu Gly Leu Val Asp Thr Ser Val Ala Lys Ile Val Ser Asp
                645                 650                 655

Arg Asn Leu Pro Phe Val Ala Arg Gln Met Ala Leu His Ala Asn Met
                660                 665                 670

Ala Ser Gln Val His His Ser Arg Ser Asn Pro Thr Asp Ile Tyr Pro
                675                 680                 685

Ser Lys Trp Ile Ala Arg Leu Arg His Ile Lys Arg Leu Arg Gln Arg
                690                 695                 700

Ile Cys Glu Glu Ala Ala Tyr Ser Asn Pro Ser Leu Pro Leu Val His
705                 710                 715                 720

Pro Pro Ser His Ser Lys Ala Pro Ala Gln Thr Pro Ala Glu Pro Thr
                725                 730                 735

Pro Gly Tyr Glu Val Gly Gln Arg Lys Arg Leu Ile Ser Ser Val Glu
                740                 745                 750

Asp Phe Thr Glu Phe Val
                755

<210> SEQ ID NO 2
<211> LENGTH: 450
<212> TYPE: PRT
<213> ORGANISM: Artificial Sequence
<220> FEATURE:
<223> OTHER INFORMATION: Synthetic Construct

<400> SEQUENCE: 2

Met Ala Lys Pro Thr Ser Lys Asp Ser Gly Leu Lys Glu Lys Phe Lys
1               5                   10                  15

Ile Leu Leu Gly Leu Gly Thr Pro Arg Pro Asn Pro Arg Ser Ala Glu
                20                  25                  30

Gly Lys Gln Thr Glu Phe Ile Ile Thr Ala Glu Ile Leu Arg Glu Leu
                35                  40                  45

Ser Met Glu Cys Gly Leu Asn Asn Arg Ile Arg Met Ile Gly Gln Ile
50                  55                  60

Cys Glu Val Ala Lys Thr Lys Lys Phe Glu Glu His Ala Val Glu Ala
65                  70                  75                  80

Leu Trp Lys Ala Val Ala Asp Leu Leu Gln Pro Glu Arg Pro Leu Glu
                85                  90                  95

Ala Arg His Ala Val Leu Ala Leu Leu Lys Ala Ile Val Gln Gly Gln
                100                 105                 110

Gly Glu Arg Leu Gly Val Leu Arg Ala Leu Phe Phe Lys Val Ile Lys
                115                 120                 125

Asp Tyr Pro Ser Asn Glu Asp Leu His Glu Arg Leu Glu Val Phe Lys
```

-continued

```
                130                 135                 140
Ala Leu Thr Asp Asn Gly Arg His Ile Thr Tyr Leu Glu Glu Leu
145                 150                 155                 160

Ala Asp Phe Val Leu Gln Trp Met Asp Val Gly Leu Ser Ser Glu Phe
                165                 170                 175

Leu Leu Val Leu Val Asn Leu Val Lys Phe Asn Ser Cys Tyr Leu Asp
                180                 185                 190

Glu Tyr Ile Ala Arg Met Val Gln Met Ile Cys Leu Leu Cys Val Arg
                195                 200                 205

Thr Ala Ser Ser Val Asp Ile Glu Val Ser Leu Gln Val Leu Asp Ala
                210                 215                 220

Val Val Cys Tyr Asn Cys Leu Pro Ala Glu Ser Leu Pro Leu Phe Ile
225                 230                 235                 240

Val Thr Leu Cys Arg Thr Ile Asn Val Lys Glu Leu Cys Glu Pro Cys
                245                 250                 255

Trp Lys Leu Met Arg Asn Leu Leu Gly Thr His Leu Gly His Ser Ala
                260                 265                 270

Ile Tyr Asn Met Cys His Leu Met Glu Asp Arg Ala Tyr Met Glu Asp
                275                 280                 285

Ala Pro Leu Leu Arg Gly Ala Val Phe Phe Val Gly Met Ala Leu Trp
                290                 295                 300

Gly Ala His Arg Leu Tyr Ser Leu Arg Asn Ser Pro Thr Ser Val Leu
305                 310                 315                 320

Pro Ser Phe Tyr Gln Ala Met Ala Cys Pro Asn Glu Val Val Ser Tyr
                325                 330                 335

Glu Ile Val Leu Ser Ile Thr Arg Leu Ile Lys Lys Tyr Arg Lys Glu
                340                 345                 350

Leu Gln Val Val Ala Trp Asp Ile Leu Leu Asn Ile Ile Glu Arg Leu
                355                 360                 365

Leu Gln Gln Leu Gln Thr Leu Asp Ser Pro Glu Leu Arg Thr Ile Val
                370                 375                 380

His Asp Leu Leu Thr Thr Val Glu Glu Leu Cys Asp Gln Asn Glu Phe
385                 390                 395                 400

His Gly Ser Gln Glu Arg Tyr Phe Glu Leu Val Glu Arg Cys Ala Asp
                405                 410                 415

Gln Arg Pro Glu Ser Ser Leu Leu Asn Leu Ile Ser Tyr Arg Ala Gln
                420                 425                 430

Ser Ile His Pro Ala Lys Asp Gly Trp Ile Gln Asn Leu Gln Ala Leu
                435                 440                 445

Met Glu
    450

<210> SEQ ID NO 3
<211> LENGTH: 292
<212> TYPE: PRT
<213> ORGANISM: Artificial Sequence
<220> FEATURE:
<223> OTHER INFORMATION: Synthetic Construct

<400> SEQUENCE: 3

Lys Pro Ile Leu Leu Pro Asn Glu Ser Gln Ser Phe Glu Arg Ser Val
1               5                   10                  15

Gln Leu Leu Asp Gln Ile Pro Ser Tyr Asp Thr His Lys Ile Ala Val
                20                  25                  30

Leu Tyr Val Gly Glu Gly Gln Ser Asn Ser Glu Leu Ala Ile Leu Ser
```

```
                       35                  40                  45
Asn Glu His Gly Ser Tyr Arg Tyr Thr Glu Phe Leu Thr Gly Leu Gly
     50                  55                  60

Arg Leu Ile Glu Leu Lys Asp Cys Gln Pro Asp Lys Val Tyr Leu Gly
65                  70                  75                  80

Gly Leu Asp Val Cys Gly Glu Asp Gly Gln Phe Thr Tyr Cys Trp His
                 85                  90                  95

Asp Asp Ile Met Gln Ala Val Phe His Ile Ala Thr Leu Met Pro Thr
            100                 105                 110

Lys Asp Val Asp Lys His Arg Cys Asp Lys Lys Arg His Leu Gly Asn
        115                 120                 125

Asp Phe Val Ser Ile Val Tyr Asn Asp Ser Gly Glu Asp Phe Lys Leu
    130                 135                 140

Gly Thr Ile Lys Gly Gln Phe Asn Phe Val His Val Ile Val Thr Pro
145                 150                 155                 160

Leu Asp Tyr Glu Cys Asn Leu Val Ser Leu Gln Cys Arg Lys Asp Met
                165                 170                 175

Glu Gly Leu Val Asp Thr Ser Val Ala Lys Ile Val Ser Asp Arg Asn
            180                 185                 190

Leu Pro Phe Val Ala Arg Gln Met Ala Leu His Ala Asn Met Ala Ser
        195                 200                 205

Gln Val His His Ser Arg Ser Asn Pro Thr Asp Ile Tyr Pro Ser Lys
    210                 215                 220

Trp Ile Ala Arg Leu Arg His Ile Lys Arg Leu Arg Gln Arg Ile Cys
225                 230                 235                 240

Glu Glu Ala Ala Tyr Ser Asn Pro Ser Leu Pro Leu Val His Pro Pro
                245                 250                 255

Ser His Ser Lys Ala Pro Ala Gln Thr Pro Ala Glu Pro Thr Pro Gly
            260                 265                 270

Tyr Glu Val Gly Gln Arg Lys Arg Leu Ile Ser Ser Val Glu Asp Phe
        275                 280                 285

Thr Glu Phe Val
    290

<210> SEQ ID NO 4
<211> LENGTH: 16
<212> TYPE: PRT
<213> ORGANISM: Artificial Sequence
<220> FEATURE:
<223> OTHER INFORMATION: Synthetic Construct

<400> SEQUENCE: 4

Ser Gly Gly Gly Ser Gly Gly Gly Ser Gly Gly Gly Ser Gly Gly Gly
1               5                  10                  15

<210> SEQ ID NO 5
<211> LENGTH: 2306
<212> TYPE: DNA
<213> ORGANISM: Artificial Sequence
<220> FEATURE:
<223> OTHER INFORMATION: Synthetic Construct

<400> SEQUENCE: 5
gctagcacta gtaccatggc gaaaccgacc agcaaagata gcggcctgaa agaaaaattt      60
aaaattctgc tgggcctggg caccccgcgc ccgaacccgc gcagcgcgga aggcaaacag     120
accgaattta ttattaccgc ggaaattctg cgcgaactga gcatggaatg cggcctgaac     180
```

-continued

| | |
|---|---|
| aaccgcattc gcatgattgg ccagatttgc gaagtggcga aaaccaaaaa atttgaagaa | 240 |
| catgcggtgg aagcgctgtg gaaagcggtg gcggatctgc tgcagccgga acgcccgctg | 300 |
| gaagcgcgcc atgcggtgct ggcgctgctg aaagcgattg tgcagggcca gggcgaacgc | 360 |
| ctgggcgtgc tgcgcgcgct gtttttaaaa gtgattaaag attatccgag caacgaagat | 420 |
| ctgcatgaac gcctggaagt gtttaaagcg ctgaccgata acggccgcca tattacctat | 480 |
| ctggaagaag aactggcgga ttttgtgctg cagtggatgg atgtgggcct gagcagcgaa | 540 |
| tttctgctgg tgctggtgaa cctggtgaaa tttaacagct gctatctgga tgaatatatt | 600 |
| gcgcgcatgg tgcagatgat ttgcctgctg tgcgtgcgca ccgcgagcag cgtggatatt | 660 |
| gaagtgagcc tgcaggtgct ggatgcggtg gtgtgctata actgcctgcc ggcggaaagc | 720 |
| ctgccgctgt ttattgtgac cctgtgccgc accattaacg tgaaagaact gtgcgaaccg | 780 |
| tgctggaaac tgatgcgcaa cctgctgggc acccatctgg ccatagcgc gatttataac | 840 |
| atgtgccatc tgatggaaga tcgcgcgtat atggaagatg cgccgctgct gcgcggcgcg | 900 |
| gtgttttttg tgggcatggc gctgtggggc gcgatccgcc tgtatagcct gcgcaacagc | 960 |
| ccgaccagcg tgctgccgag cttttatcag gcgatggcgt gcccgaacga agtggtgagc | 1020 |
| tatgaaattg tgctgagcat tacccgcctg attaaaaaat atcgcaaaga actgcaggtg | 1080 |
| gtggcgtggg atattctgct gaacattatt gaacgcctgc tgcagcagct gcagaccctg | 1140 |
| gatagcccgg aactgcgcac cattgtgcat gatctgctga ccaccgtgga agaactgtgc | 1200 |
| gatcagaacg aatttcatgg cagccaggaa cgctattttg aactggtgga acgctgcgcg | 1260 |
| gatcagcgcc cggaaagcag cctgctgaac ctgattagct atcgcgcgca gagcattcat | 1320 |
| ccggcgaaag atggctggat tcagaacctg caggcgctga tggaatctgg tgggggtagc | 1380 |
| ggaggagggt caggggcgg cagtggaggc ggaaaaccga ttctgctgcc gaacgaaagc | 1440 |
| cagagctttg aacgcagcgt gcagctgctg gatcagattc cgagctatga tacccataaa | 1500 |
| attgcggtgc tgtatgtggg cgaaggccag agcaacagcg aactggcgat tctgagcaac | 1560 |
| gaacatggca gctatcgcta taccgaattt ctgaccggcc tgggccgcct gattgaactg | 1620 |
| aaagattgcc agccggataa agtgtatctg gcggcctgg atgtgtgcgg cgaagatggc | 1680 |
| cagtttacct attgctggca tgatgatatt atgcaggcgg tgtttcatat tgcgacccctg | 1740 |
| atgccgacca aagatgtgga taaacatcgc tgcgataaaa aacgccatct gggcaacgat | 1800 |
| tttgtgagca ttgtgtataa cgatagcggc gaagatttta aactgggcac cattaaaggc | 1860 |
| cagtttaact ttgtgcatgt gattgtgacc ccgctggatt atgaatgcaa cctggtgagc | 1920 |
| ctgcagtgcc gcaaagatat ggaaggcctg gtggatacca gcgtggcgaa aattgtgagc | 1980 |
| gatcgcaacc tgccgtttgt ggcgcgccag atggcgctgc atgcgaacat ggcgagccag | 2040 |
| gtgcatcata gccgcagcaa cccgaccgat atttatccga gcaaatggat tgcgcgcctg | 2100 |
| cgccatatta aacgcctgcg ccagcgcatt tgcgaagaag cggcgtatag caacccgagc | 2160 |
| ctgccgctgg tgcatccgcc gagccatagc aaagcgccgg cgcagacccc ggcggaaccg | 2220 |
| accccgggct atgaagtggg ccagcgcaaa cgcctgatta gcagcgtgga agatttacc | 2280 |
| gaatttgtgt aggcggccgc ctcgag | 2306 |

<210> SEQ ID NO 6
<211> LENGTH: 1353
<212> TYPE: DNA
<213> ORGANISM: Artificial Sequence
<220> FEATURE:
<223> OTHER INFORMATION: Synthetic Construct

<400> SEQUENCE: 6

```
accatggcga aaccgaccag caaagatagc ggcctgaaag aaaaatttaa aattctgctg      60
ggcctgggca ccccgcgccc gaacccgcgc agcgcggaag gcaaacagac cgaatttatt     120
attaccgcgg aaattctgcg cgaactgagc atggaatgcg gcctgaacaa ccgcattcgc     180
atgattggcc agatttgcga agtggcgaaa accaaaaaat tgaagaaca tgcggtggaa      240
gcgctgtgga aagcggtggc ggatctgctg cagccggaac gcccgctgga agcgcgccat     300
gcggtgctgg cgctgctgaa agcgattgtg cagggccagg cgaacgcct gggcgtgctg      360
cgcgcgctgt tttttaaagt gattaaagat tatccgagca acgaagatct gcatgaacgc     420
ctggaagtgt ttaaagcgct gaccgataac ggccgccata ttacctatct ggaagaagaa     480
ctggcggatt ttgtgctgca gtggatggat gtgggcctga gcagcgaatt tctgctggtg     540
ctggtgaacc tggtgaaatt taacagctgc tatctggatg aatatattgc gcgcatggtg     600
cagatgattt gcctgctgtg cgtgcgcacc gcgagcagcg tggatattga agtgagcctg     660
caggtgctgg atgcggtggt gtgctataac tgcctgccgg cggaaagcct gccgctgttt     720
attgtgaccc tgtgccgcac cattaacgtg aaagaactgt gcgaaccgtg ctggaaactg     780
atgcgcaacc tgctgggcac ccatctgggc catagcgcga tttataacat gtgccatctg     840
atggaagatc gcgcgtatat ggaagatgcg ccgctgctgc gcggcgcggt gttttttgtg     900
ggcatggcgc tgtggggcgc gcatcgcctg tatagcctgc gcaacagccc gaccagcgtg     960
ctgccgagct tttatcaggc gatggcgtgc ccgaacgaag tggtgagcta tgaaattgtg    1020
ctgagcatta cccgcctgat taaaaaatat cgcaaagaac tgcaggtggt ggcgtgggat    1080
attctgctga acattattga acgcctgctg cagcagctgc agaccctgga tagcccggaa    1140
ctgcgcacca ttgtgcatga tctgctgacc accgtggaag aactgtgcga tcagaacgaa    1200
tttcatggca gccaggaacg ctattttgaa ctggtggaaa gctgcgcgga tcagcgcccg    1260
gaaagcagcc tgctgaacct gattagctat cgcgcgcaga gcattcatcc ggcgaaagat    1320
ggctggattc agaacctgca ggcgctgatg gaa                                 1353
```

<210> SEQ ID NO 7
<211> LENGTH: 876
<212> TYPE: DNA
<213> ORGANISM: Artificial Sequence
<220> FEATURE:
<223> OTHER INFORMATION: Synthetic Construct

<400> SEQUENCE: 7

```
aaaccgattc tgctgccgaa cgaaagccag agctttgaac gcagcgtgca gctgctggat      60
cagattccga gctatgatac ccataaaatt gcggtgctgt atgtgggcga aggccagagc     120
aacagcgaac tggcgattct gagcaacgaa catggcagct atcgctatac cgaatttctg     180
accggcctgg gcgcctgat tgaactgaaa gattgccagc cggataaagt gtatctgggc     240
ggcctggatg tgtgcggcga agatggccag tttacctatt gctggcatga tgatattatg     300
caggcggtgt tcatattgc gaccctgatg ccgaccaaag atgtggataa acatcgctgc      360
gataaaaaac gccatctggg caacgatttt gtgagcattg tgtataacga tagcggcgaa     420
gattttaaac tggcaccat taaaggccag tttaactttg tgcatgtgat tgtgaccccg      480
ctggattatg aatgcaacct ggtgagcctg cagtgccgca agatatgga aggcctggtg      540
gataccagcg tggcgaaaat tgtgagcgat cgcaacctgc cgtttgtggc cgccagatg     600
```

| | | |
|---|---|---|
| gcgctgcatg cgaacatggc gagccaggtg catcatagcc gcagcaaccc gaccgatatt | 660 | |
| tatccgagca aatggattgc gcgcctgcgc catattaaac gcctgcgcca gcgcatttgc | 720 | |
| gaagaagcgg cgtatagcaa cccgagcctg ccgctggtgc atccgccgag ccatagcaaa | 780 | |
| gcgccggcgc agaccccggc ggaaccgacc ccgggctatg aagtgggcca gcgcaaacgc | 840 | |
| ctgattagca gcgtggaaga ttttaccgaa tttgtg | 876 | |

<210> SEQ ID NO 8
<211> LENGTH: 48
<212> TYPE: DNA
<213> ORGANISM: Artificial Sequence
<220> FEATURE:
<223> OTHER INFORMATION: Synthetic Construct

<400> SEQUENCE: 8

| | |
|---|---|
| tctggtgggg gtagcggagg agggtcaggg ggcggcagtg gaggcgga | 48 |

<210> SEQ ID NO 9
<211> LENGTH: 7540
<212> TYPE: DNA
<213> ORGANISM: Artificial Sequence
<220> FEATURE:
<223> OTHER INFORMATION: Synthetic Construct

<400> SEQUENCE: 9

| | |
|---|---|
| ggccgctcta gaagataatc aacctctgga ttacaaaatt tgtgaaagat tgactggtat | 60 |
| tcttaactat gttgctcctt ttacgctatg tggatacgct gctttaatgc ctttgtatca | 120 |
| tgctattgct tcccgtatgg ctttcatttt ctcctccttg tataaatcct ggttgctgtc | 180 |
| tctttatgag gagttgtggc ccgttgtcag gcaacgtggc gtggtgtgca ctgtgtttgc | 240 |
| tgacgcaacc cccactggtt ggggcattgc caccacctgt cagctccttt ccgggacttt | 300 |
| cgctttcccc ctccctattg ccacggcgga actcatcgcc gcctgccttg cccgctgctg | 360 |
| gacaggggct cggctgttgg gcactgacaa ttccgtggtg ttgtcgggga agctgacgtc | 420 |
| ctttccatgg ctgctcgcct gtgttgccac ctggattctg cgcgggacgt ccttctgcta | 480 |
| cgtcccttcg gccctcaatc cagcggacct tccttcccgc ggcctgctgc cggctctgcg | 540 |
| gcctcttccg cgtcttcgcc ttcgccctca gacgagtcgg atctcccttt gggccgcctc | 600 |
| cccgcatcgg actagagaga tccagacatg ataagataca ttgatgagtt tggacaaacc | 660 |
| acaactagaa tgcagtgaaa aaaatgcttt atttgtgaaa tttgtgatgc tattgcttta | 720 |
| tttgtaacca ttataagctg caataaacaa gttaacaaca caattgcat tcattttatg | 780 |
| tttcaggttc agggggaggt gtgggaggtt ttttagtcga ctagagctcg ctgatcagcc | 840 |
| tcgactgtgc cttctagttg ccagccatct gttgtttgcc cctcccccgt gccttccttg | 900 |
| accctggaag gtgccactcc cactgtcctt tcctaataaa atgaggaaat tgcatcgcat | 960 |
| tgtctgagta ggtgtcattc tattctgggg ggtggggtgg gcaggacag caaggggggag | 1020 |
| gattgggaag acaatagcag gcatgctggg gagagatcta ggaacccta gtgatggagt | 1080 |
| tggccactcc ctctctgcgc gctcgctcgc tcactgaggc cgcccgggca agcccgggc | 1140 |
| gtcgggcgac ctttggtcgc ccggcctcag tgagcgagcg agcgcgcaga gagggagtgg | 1200 |
| ccatgcagcc agctggcgta atagcgaaga ggcccgcacc gatcgccctt cccaacagtt | 1260 |
| gcgtagcctg aatggcgaat ggcgcgacgc gccctgtagc ggcgcattaa gcgcggcggg | 1320 |
| tgtggtggtt acgcgcagcg tgaccgctac acttgccagc gccctagcgc ccgctccttt | 1380 |
| cgctttcttc ccttcctttc tcgccacgtt cgccggcttt ccccgtcaag ctctaaatcg | 1440 |

```
ggggctccct ttagggttcc gatttagtgc tttacggcac ctcgacccca aaaaacttga  1500
ttagggtgat ggttcacgta gtgggccatc gccctgatag acggttttc gcccttgac  1560
gttggagtcc acgttcttta atagtggact cttgttccaa actggaacaa cactcaaccc  1620
tatctcggtc tattcttttg atttataagg gattttgccg atttcggcct attggttaaa  1680
aaatgagctg atttaacaaa aatttaacgc gaattttaac aaaatattaa cgtttacaat  1740
ttcctgatgc ggtattttct ccttacgcat ctgtgcggta tttcacaccg catatggtgc  1800
actctcagta caatctgctc tgatgccgca tagttaagcc agccccgaca cccgccaaca  1860
cccgctgacg cgccctgacg ggcttgtctg ctcccggcat ccgcttacag acaagctgtg  1920
accgtctccg ggagctgcat gtgtcagagg ttttcaccgt catcaccgaa acgcgcgaga  1980
cgaaagggcc tcgtgatacg cctatttta taggttaatg tcatgataat aatggtttct  2040
tagacgtcag gtggcacttt tcggggaaat gtgcgcggaa cccctatttg tttattttc   2100
taaatacatt caaatatgta tccgctcatg agacaataac cctgataaat gcttcaataa  2160
tattgaaaaa ggaagagtat gagtattcaa catttccgtg tcgcccttat cccttttttt  2220
gcggcatttt gccttcctgt ttttgctcac ccagaaacgc tggtgaaagt aaaagatgct  2280
gaagatcagt tgggtgcacg agtgggttac atcgaactgg atctcaacag cggtaagatc  2340
cttgagagtt tcgccccga agaacgtttt ccaatgatga gcacttttaa agttctgcta  2400
tgtggcgcgg tattatcccg tattgacgcc gggcaagagc aactcggtcg ccgcatacac  2460
tattctcaga atgacttggt tgagtactca ccagtcacag aaaagcatct tacgatggc   2520
atgacagtaa gagaattatg cagtgctgcc ataaccatga gtgataacac tgcggccaac  2580
ttacttctga caacgatcgg aggaccgaag gagctaaccg cttttttgca acatgggg    2640
gatcatgtaa ctcgccttga tcgttgggaa ccggagctga atgaagccat accaaacgac  2700
gagcgtgaca ccacgatgcc tgtagcaatg gcaacaacgt tgcgcaaact attaactggc  2760
gaactactta ctctagcttc ccggcaacaa ttaatagact ggatggaggc ggataaagtt  2820
gcaggaccac ttctgcgctc ggcccttccg gctggctggt ttattgctga taaatctgga  2880
gccggtgagc gtgggtctcg cggtatcatt gcagcactgg ggccagatgg taagccctcc  2940
cgtatcgtag ttatctacac gacggggagt caggcaacta tggatgaacg aaatagacag  3000
atcgctgaga taggtgcctc actgattaag cattggtaac tgtcagacca agtttactca  3060
tatatacttt agattgattt aaaacttcat ttttaattta aaaggatcta ggtgaagatc  3120
cttttttgata atctcatgac caaaatccct taacgtgagt tttcgttcca ctgagcgtca  3180
gaccccgtag aaaagatcaa aggatcttct tgagatcctt ttttttctgcg cgtaatctgc  3240
tgcttgcaaa caaaaaaacc accgctacca gcggtggttt gtttgccgga tcaagagcta  3300
ccaactcttt ttccgaaggt aactggcttc agcagagcgc agataccaaa tactgtcctt  3360
ctagtgtagc cgtagttagg ccaccacttc aagaactctg tagcaccgcc tacatacctc  3420
gctctgctaa tcctgttacc agtggctgct gccagtggcg ataagtcgtg tcttaccggg  3480
ttggactcaa gacgatagtt accggataag gcgcagcggt cgggctgaac ggggggttcg  3540
tgcacacagc ccagcttgga gcgaacgacc tacaccgaac tgagatacct acagcgtgag  3600
cattgagaaa gcgccacgct tcccgaaggg agaaaggcgg acaggtatcc ggtaagcggc  3660
agggtcggaa caggagagcg cacgagggag cttccagggg gaaacgcctg gtatctttat  3720
agtcctgtcg ggtttcgcca cctctgactt gagcgtcgat ttttgtgatg ctcgtcaggg  3780
```

```
gggcggagcc tatggaaaaa cgccagcaac gcggcctttt tacggttcct ggccttttgc    3840
tggccttttg ctcacatgtt ctttcctgcg ttatcccctg attctgtgga taaccgtatt    3900
accgcctttg agtgagctga taccgctcgc cgcagccgaa cgaccgagcg cagcgagtca    3960
gtgagcgagg aagcggaaga cgcccaata cgcaaaccgc ctctccccgc gcgttggccg    4020
attcattaat gcagctgggc tgcaggggggg ggggggggggg ggtgggggggg ggggggggggg   4080 gttggccact ccctctctgc gcgctcgctc gctcactgag gccgggcgac caaaggtcgc    4140
ccgacgcccg ggctttgccc gggcggcctc agtgagcgag cgagcgcgca gagagggagt    4200
ggccaactcc atcactaggg gttcctagat ctgaattcgg taccctagtt attaatagta    4260
atcaattacg gggtcattag ttcatagccc atatatggag ttccgcgtta cataacttac    4320
ggtaaatggc ccgcctggct gaccgcccaa cgacccccgc ccattgacgt caataatgac    4380
gtatgttccc atagtaacgc caatagggac tttccattga cgtcaatggg tggactattt    4440
acggtaaact gcccacttgg cagtacatca agtgtatcat atgccaagta cgccccctat    4500
tgacgtcaat gacggtaaat ggcccgcctg gcattatgcc cagtacatga ccttatggga    4560
ctttcctact tggcagtaca tctacgtatt agtcatcgct attaccatgg tcgaggtgag    4620
ccccacgttc tgcttcactc tccccatctc ccccccctcc ccaccccaa ttttgtattt    4680 atttattttt taattatttt gtgcagcgat ggggcgggg ggggggggggg ggcgcgcgcc    4740 aggcggggcg gggcggggcg aggggcgggg cggggcgagg cggagaggtg cggcggcagc    4800
caatcagagc ggcgcgctcc gaaagtttcc tttatggcg aggcggcggc ggcggcggcc    4860
ctataaaaag cgaagcgcgc ggcgggcggg agtcgctgcg acgctgcctt cgccccgtgc    4920
cccgctccgc cgccgcctcg cgccgcccgc cccggctctg actgaccgcg ttactcccac    4980
aggtgagcgg gcgggacggc ccttctcctc cgggctgtaa ttagcgcttg gtttaatgac    5040
ggcttgtttc ttttctgtgg ctgcgtgaaa gccttgaggg gctccgggag ctagagcctc    5100
tgctaaccat gttcatgcct tcttcttttt cctacagctc ctgggcaacg tgctggttat    5160
tgtgctgtct catcattttg gcaaagaatt cctcgaagat ccgaaggggt tcaagcttaa    5220
aaactagtac catggcaaaa cctacatcaa aagatagcgg actgaaagag aagttcaaaa    5280
tcctgctggg actggggaca ccacgcccta atccacggtc cgccgagggc aagcagaccg    5340
agttcatcat cacagccgag atcctgcgcg agctgtctat ggagtgcggc ctgaacaatc    5400
ggatcagaat gatcggccag atttgcgagg tggccaagac caagaagttt gaggagcacg    5460
cagtggaggc cctgtggaag gcagtggccg atctgctgca gcctgagaga ccactggagg    5520
caaggcacgc cgtgctggcc ctgctgaagg ccatcgtgca gggacaggga gagcgcctgg    5580
gcgtgctgcg ggccctgttc tttaaagtga tcaaggacta ccctagcaac gaggatctgc    5640
acgagagact ggaggtgttc aaggccctga ccgataatgg caggcacatc acatatctgg    5700
aggaggagct ggccgacttt gtgctgcagt ggatggatgt gggcctgagc tccgagttcc    5760
tgctggtgct ggtgaacctg gtgaagttta attcctgcta cctggacgag tatatcgccc    5820
gcatggtgca gatgatctgc ctgctgtgcg tgcggaccgc ctctagcgtg gacatcgagg    5880
tgtctctgca ggtgctggat gccgtggtgt gctacaactg tctgcccgcc gagagcctgc    5940
ctctgttcat cgtgaccctg tgcagaacaa tcaatgtgaa ggagctgtgc gagccttgtt    6000
ggaagctgat gaggaacctg ctgggcacac acctgggaca cagcgccatc tacaatatgt    6060
gccacctgat ggaggaccgc gcctatatgg aggatgcacc actgctgagg ggagccgtgt    6120 tcttgtggg aatggcactg tggggagcac acagactgta ctccctgagg aactctccaa    6180
```

```
ccagcgtgct gccctctttt taccaggcta tggcctgtcc aaatgaggtg gtgtcttatg    6240
agatcgtgct gagcatcaca cgcctgatca agaagtatcg gaaggagctg caggtggtgg    6300
cctgggacat cctgctgaac atcatcgagc gcctgctgca gcagctgcag accctggaca    6360
gcccagagct gaggacaatc gtgcacgatc tgctgaccac agtggaggag ctgtgcgacc    6420
agaatgagtt ccacggctcc caggagcggt actttgagct ggtggagcgg tgcgcagatc    6480
agaggccaga gtcctctctg ctgaacctga tctcctatcg ggcccagtct atccaccctg    6540
ccaaggacgg ctggattcag aatctgcagg ccctgatgga gagcggagga ggctccggag    6600
gaggctctgg aggcggcagc ggcggcggca agccaatcct gctgcccaac gagagccaga    6660
gcttcgagcg gagcgtgcag ctgctggacc agatccccag ctacgatacc acaagatcg    6720 ccgtgctgta tgtgggcgag ggccagtcta acagcgagct ggccatcctg agcaatgagc    6780
acggctccta cagatatacc gagtttctga caggcctggg caggctgatc gagctgaagg    6840
actgccagcc cgataaggtg tacctgggag gcctggacgt gtgcgagag gatggccagt    6900 tcacctattg ttggcacgac gatatcatgc aggccgtgtt tcacatcgcc accctgatgc    6960
ctacaaagga cgtggataag cacagatgtg acaagaagag gcacctgggc aacgatttcg    7020
tgtccatcgt gtacaatgac tctggcgagg acttcaagct gggcaccatc aagggccagt    7080
tcaactttgt gcacgtgatc gtgacaccac tggattatga gtgcaatctg gtgagcctgc    7140
agtgtagaaa ggacatggag ggcctggtgg ataccagcgt ggccaagatc gtgtccgaca    7200
gaaacctgcc cttcgtggcc aggcagatgg ccctgcacgc caacatggcc agccaggtgc    7260
accactccag gtctaatcct acagacatct acccatccaa gtggatcgcc aggctgcgcc    7320
acatcaagcg gctgagacag aggatctgcg aggaggccgc ctattccaat ccctctctgc    7380
ctctggtgca cccacctagc cactccaagg cacctgcaca gaccccagca gagccaacac    7440
caggatacga agtgggacag aggaagcggc tgatctcctc cgtggaagat ttcaccgaat    7500 tgtggagca gaagctgatt agcgaagaag acctgtaagc                           7540
```

<210> SEQ ID NO 10
<211> LENGTH: 1807
<212> TYPE: PRT
<213> ORGANISM: Homo sapiens

<400> SEQUENCE: 10

```
Met Ala Lys Pro Thr Ser Lys Asp Ser Gly Leu Lys Glu Lys Phe Lys
1               5                   10                  15

Ile Leu Leu Gly Leu Gly Thr Pro Arg Pro Asn Pro Arg Ser Ala Glu
            20                  25                  30

Gly Lys Gln Thr Glu Phe Ile Ile Thr Ala Glu Ile Leu Arg Glu Leu
        35                  40                  45

Ser Met Glu Cys Gly Leu Asn Asn Arg Ile Arg Met Ile Gly Gln Ile
    50                  55                  60

Cys Glu Val Ala Lys Thr Lys Lys Phe Glu Glu His Ala Val Glu Ala
65                  70                  75                  80

Leu Trp Lys Ala Val Ala Asp Leu Leu Gln Pro Glu Arg Pro Leu Glu
                85                  90                  95

Ala Arg His Ala Val Leu Ala Leu Leu Lys Ala Ile Val Gln Gly Gln
            100                 105                 110

Gly Glu Arg Leu Gly Val Leu Arg Ala Leu Phe Phe Lys Val Ile Lys
        115                 120                 125
```

```
Asp Tyr Pro Ser Asn Glu Asp Leu His Glu Arg Leu Glu Val Phe Lys
    130                 135                 140

Ala Leu Thr Asp Asn Gly Arg His Ile Thr Tyr Leu Glu Glu Glu Leu
145                 150                 155                 160

Ala Asp Phe Val Leu Gln Trp Met Asp Val Gly Leu Ser Ser Glu Phe
                165                 170                 175

Leu Leu Val Leu Val Asn Leu Val Lys Phe Asn Ser Cys Tyr Leu Asp
            180                 185                 190

Glu Tyr Ile Ala Arg Met Val Gln Met Ile Cys Leu Cys Val Arg
        195                 200                 205

Thr Ala Ser Ser Val Asp Ile Glu Val Ser Leu Gln Val Leu Asp Ala
210                 215                 220

Val Val Cys Tyr Asn Cys Leu Pro Ala Glu Ser Leu Pro Leu Phe Ile
225                 230                 235                 240

Val Thr Leu Cys Arg Thr Ile Asn Val Lys Glu Leu Cys Glu Pro Cys
                245                 250                 255

Trp Lys Leu Met Arg Asn Leu Leu Gly Thr His Leu Gly His Ser Ala
            260                 265                 270

Ile Tyr Asn Met Cys His Leu Met Glu Asp Arg Ala Tyr Met Glu Asp
        275                 280                 285

Ala Pro Leu Leu Arg Gly Ala Val Phe Phe Val Gly Met Ala Leu Trp
290                 295                 300

Gly Ala His Arg Leu Tyr Ser Leu Arg Asn Ser Pro Thr Ser Val Leu
305                 310                 315                 320

Pro Ser Phe Tyr Gln Ala Met Ala Cys Pro Asn Glu Val Val Ser Tyr
                325                 330                 335

Glu Ile Val Leu Ser Ile Thr Arg Leu Ile Lys Lys Tyr Arg Lys Glu
            340                 345                 350

Leu Gln Val Val Ala Trp Asp Ile Leu Leu Asn Ile Ile Glu Arg Leu
        355                 360                 365

Leu Gln Gln Leu Gln Thr Leu Asp Ser Pro Glu Leu Arg Thr Ile Val
370                 375                 380

His Asp Leu Leu Thr Thr Val Glu Glu Leu Cys Asp Gln Asn Glu Phe
385                 390                 395                 400

His Gly Ser Gln Glu Arg Tyr Phe Glu Leu Val Glu Arg Cys Ala Asp
                405                 410                 415

Gln Arg Pro Glu Ser Ser Leu Leu Asn Leu Ile Ser Tyr Arg Ala Gln
            420                 425                 430

Ser Ile His Pro Ala Lys Asp Gly Trp Ile Gln Asn Leu Gln Ala Leu
        435                 440                 445

Met Glu Arg Phe Phe Arg Ser Glu Ser Arg Gly Ala Val Arg Ile Lys
450                 455                 460

Val Leu Asp Val Leu Ser Phe Val Leu Leu Ile Asn Arg Gln Phe Tyr
465                 470                 475                 480

Glu Glu Glu Leu Ile Asn Ser Val Val Ile Ser Gln Leu Ser His Ile
                485                 490                 495

Pro Glu Asp Lys Asp His Gln Val Arg Lys Leu Ala Thr Gln Leu Leu
            500                 505                 510

Val Asp Leu Ala Glu Gly Cys His Thr His His Phe Asn Ser Leu Leu
        515                 520                 525

Asp Ile Ile Glu Lys Val Met Ala Arg Ser Leu Ser Pro Pro Pro Glu
530                 535                 540

Leu Glu Glu Arg Asp Val Ala Ala Tyr Ser Ala Ser Leu Glu Asp Val
```

```
              545                 550                 555                 560
Lys Thr Ala Val Leu Gly Leu Val Ile Leu Gln Thr Lys Leu Tyr
                565                 570                 575

Thr Leu Pro Ala Ser His Ala Thr Arg Val Tyr Glu Met Leu Val Ser
                580                 585                 590

His Ile Gln Leu His Tyr Lys His Ser Tyr Thr Leu Pro Ile Ala Ser
                595                 600                 605

Ser Ile Arg Leu Gln Ala Phe Asp Phe Leu Leu Leu Arg Ala Asp
610                 615                 620

Ser Leu His Arg Leu Gly Leu Pro Asn Lys Asp Gly Val Val Arg Phe
625                 630                 635                 640

Ser Pro Tyr Cys Val Cys Asp Tyr Met Glu Pro Glu Arg Gly Ser Glu
                645                 650                 655

Lys Lys Thr Ser Gly Pro Leu Ser Pro Thr Gly Pro Pro Gly Pro
                660                 665                 670

Ala Pro Ala Gly Pro Ala Val Arg Leu Gly Ser Val Pro Tyr Ser Leu
                675                 680                 685

Leu Phe Arg Val Leu Leu Gln Cys Leu Lys Gln Glu Ser Asp Trp Lys
                690                 695                 700

Val Leu Lys Leu Val Leu Gly Arg Leu Pro Glu Ser Leu Arg Tyr Lys
705                 710                 715                 720

Val Leu Ile Phe Thr Ser Pro Cys Ser Val Asp Gln Leu Cys Ser Ala
                725                 730                 735

Leu Cys Ser Met Leu Ser Gly Pro Lys Thr Leu Glu Arg Leu Arg Gly
                740                 745                 750

Ala Pro Glu Gly Phe Ser Arg Thr Asp Leu His Leu Ala Val Val Pro
                755                 760                 765

Val Leu Thr Ala Leu Ile Ser Tyr His Asn Tyr Leu Asp Lys Thr Lys
                770                 775                 780

Gln Arg Glu Met Val Tyr Cys Leu Glu Gln Gly Leu Ile His Arg Cys
785                 790                 795                 800

Ala Ser Gln Cys Val Val Ala Leu Ser Ile Cys Ser Val Glu Met Pro
                805                 810                 815

Asp Ile Ile Ile Lys Ala Leu Pro Val Leu Val Lys Leu Thr His
                820                 825                 830

Ile Ser Ala Thr Ala Ser Met Ala Val Pro Leu Leu Glu Phe Leu Ser
                835                 840                 845

Thr Leu Ala Arg Leu Pro His Leu Tyr Arg Asn Phe Ala Ala Glu Gln
                850                 855                 860

Tyr Ala Ser Val Phe Ala Ile Ser Leu Pro Tyr Thr Asn Pro Ser Lys
865                 870                 875                 880

Phe Asn Gln Tyr Ile Val Cys Leu Ala His His Val Ile Ala Met Trp
                885                 890                 895

Phe Ile Arg Cys Arg Leu Pro Phe Arg Lys Asp Phe Val Pro Phe Ile
                900                 905                 910

Thr Lys Gly Leu Arg Ser Asn Val Leu Leu Ser Phe Asp Asp Thr Pro
                915                 920                 925

Glu Lys Asp Ser Phe Arg Ala Arg Ser Thr Ser Leu Asn Glu Arg Pro
                930                 935                 940

Lys Ser Leu Arg Ile Ala Arg Pro Pro Lys Gln Gly Leu Asn Asn Ser
945                 950                 955                 960

Pro Pro Val Lys Glu Phe Lys Glu Ser Ser Ala Ala Glu Ala Phe Arg
                965                 970                 975
```

-continued

Cys Arg Ser Ile Ser Val Ser Glu His Val Val Arg Ser Arg Ile Gln
              980                 985                 990

Thr Ser Leu Thr Ser Ala Ser Leu Gly Ser Ala Asp Glu Asn Ser Val
          995                 1000                1005

Ala Gln Ala Asp Asp Ser Leu Lys Asn Leu His Leu Glu Leu Thr
    1010                1015                1020

Glu Thr Cys Leu Asp Met Met Ala Arg Tyr Val Phe Ser Asn Phe
    1025                1030                1035

Thr Ala Val Pro Lys Arg Ser Pro Val Gly Glu Phe Leu Leu Ala
    1040                1045                1050

Gly Gly Arg Thr Lys Thr Trp Leu Val Gly Asn Lys Leu Val Thr
    1055                1060                1065

Val Thr Thr Ser Val Gly Thr Gly Thr Arg Ser Leu Leu Gly Leu
    1070                1075                1080

Asp Ser Gly Glu Leu Gln Ser Gly Pro Glu Ser Ser Ser Pro
    1085                1090                1095

Gly Val His Val Arg Gln Thr Lys Glu Ala Pro Ala Lys Leu Glu
    1100                1105                1110

Ser Gln Ala Gly Gln Gln Val Ser Arg Gly Ala Arg Asp Arg Val
    1115                1120                1125

Arg Ser Met Ser Gly Gly His Gly Leu Arg Val Gly Ala Leu Asp
    1130                1135                1140

Val Pro Ala Ser Gln Phe Leu Gly Ser Ala Thr Ser Pro Gly Pro
    1145                1150                1155

Arg Thr Ala Pro Ala Ala Lys Pro Glu Lys Ala Ser Ala Gly Thr
    1160                1165                1170

Arg Val Pro Val Gln Glu Lys Thr Asn Leu Ala Ala Tyr Val Pro
    1175                1180                1185

Leu Leu Thr Gln Gly Trp Ala Glu Ile Leu Val Arg Arg Pro Thr
    1190                1195                1200

Gly Asn Thr Ser Trp Leu Met Ser Leu Glu Asn Pro Leu Ser Pro
    1205                1210                1215

Phe Ser Ser Asp Ile Asn Asn Met Pro Leu Gln Glu Leu Ser Asn
    1220                1225                1230

Ala Leu Met Ala Ala Glu Arg Phe Lys Glu His Arg Asp Thr Ala
    1235                1240                1245

Leu Tyr Lys Ser Leu Ser Val Pro Ala Ala Ser Thr Ala Lys Pro
    1250                1255                1260

Pro Pro Leu Pro Arg Ser Asn Thr Val Ala Ser Phe Ser Ser Leu
    1265                1270                1275

Tyr Gln Ser Ser Cys Gln Gly Gln Leu His Arg Ser Val Ser Trp
    1280                1285                1290

Ala Asp Ser Ala Val Val Met Glu Glu Gly Ser Pro Gly Glu Val
    1295                1300                1305

Pro Val Leu Val Glu Pro Pro Gly Leu Glu Asp Val Glu Ala Ala
    1310                1315                1320

Leu Gly Met Asp Arg Arg Thr Asp Ala Tyr Ser Arg Ser Ser Ser
    1325                1330                1335

Val Ser Ser Gln Glu Glu Lys Ser Leu His Ala Glu Glu Leu Val
    1340                1345                1350

Gly Arg Gly Ile Pro Ile Glu Arg Val Val Ser Ser Glu Gly Gly
    1355                1360                1365

```
Arg Pro Ser Val Asp Leu Ser Phe Gln Pro Ser Gln Pro Leu Ser
    1370                1375                1380

Lys Ser Ser Ser Pro Glu Leu Gln Thr Leu Gln Asp Ile Leu
1385                1390                1395

Gly Asp Pro Gly Asp Lys Ala Asp Val Gly Arg Leu Ser Pro Glu
1400                1405                1410

Val Lys Ala Arg Ser Gln Ser Gly Thr Leu Asp Gly Glu Ser Ala
1415                1420                1425

Ala Trp Ser Ala Ser Gly Glu Asp Ser Arg Gly Gln Pro Glu Gly
1430                1435                1440

Pro Leu Pro Ser Ser Ser Pro Arg Ser Pro Ser Gly Leu Arg Pro
1445                1450                1455

Arg Gly Tyr Thr Ile Ser Asp Ser Ala Pro Ser Arg Arg Gly Lys
1460                1465                1470

Arg Val Glu Arg Asp Ala Leu Lys Ser Arg Ala Thr Ala Ser Asn
1475                1480                1485

Ala Glu Lys Val Pro Gly Ile Asn Pro Ser Phe Val Phe Leu Gln
1490                1495                1500

Leu Tyr His Ser Pro Phe Phe Gly Asp Glu Ser Asn Lys Pro Ile
1505                1510                1515

Leu Leu Pro Asn Glu Ser Gln Ser Phe Glu Arg Ser Val Gln Leu
1520                1525                1530

Leu Asp Gln Ile Pro Ser Tyr Asp Thr His Lys Ile Ala Val Leu
1535                1540                1545

Tyr Val Gly Glu Gly Gln Ser Asn Ser Glu Leu Ala Ile Leu Ser
1550                1555                1560

Asn Glu His Gly Ser Tyr Arg Tyr Thr Glu Phe Leu Thr Gly Leu
1565                1570                1575

Gly Arg Leu Ile Glu Leu Lys Asp Cys Gln Pro Asp Lys Val Tyr
1580                1585                1590

Leu Gly Gly Leu Asp Val Cys Gly Glu Asp Gly Gln Phe Thr Tyr
1595                1600                1605

Cys Trp His Asp Asp Ile Met Gln Ala Val Phe His Ile Ala Thr
1610                1615                1620

Leu Met Pro Thr Lys Asp Val Asp Lys His Arg Cys Asp Lys Lys
1625                1630                1635

Arg His Leu Gly Asn Asp Phe Val Ser Ile Val Tyr Asn Asp Ser
1640                1645                1650

Gly Glu Asp Phe Lys Leu Gly Thr Ile Lys Gly Gln Phe Asn Phe
1655                1660                1665

Val His Val Ile Val Thr Pro Leu Asp Tyr Glu Cys Asn Leu Val
1670                1675                1680

Ser Leu Gln Cys Arg Lys Asp Met Glu Gly Leu Val Asp Thr Ser
1685                1690                1695

Val Ala Lys Ile Val Ser Asp Arg Asn Leu Pro Phe Val Ala Arg
1700                1705                1710

Gln Met Ala Leu His Ala Asn Met Ala Ser Gln Val His His Ser
1715                1720                1725

Arg Ser Asn Pro Thr Asp Ile Tyr Pro Ser Lys Trp Ile Ala Arg
1730                1735                1740

Leu Arg His Ile Lys Arg Leu Arg Gln Arg Ile Cys Glu Glu Ala
1745                1750                1755

Ala Tyr Ser Asn Pro Ser Leu Pro Leu Val His Pro Pro Ser His
```

-continued

```
              1760                1765                1770

Ser Lys Ala Pro Ala Gln Thr  Pro Ala Glu Pro Thr  Pro Gly Tyr
    1775                1780                1785

Glu Val Gly Gln Arg Lys Arg  Leu Ile Ser Ser Val  Glu Asp Phe
    1790                1795                1800

Thr Glu Phe Val
    1805

<210> SEQ ID NO 11
<211> LENGTH: 768
<212> TYPE: PRT
<213> ORGANISM: Artificial Sequence
<220> FEATURE:
<223> OTHER INFORMATION: Synthetic Construct

<400> SEQUENCE: 11

Met Ala Lys Pro Thr Ser Lys Asp Ser Gly Leu Lys Glu Lys Phe Lys
1               5                   10                  15

Ile Leu Leu Gly Leu Gly Thr Pro Arg Pro Asn Pro Arg Ser Ala Glu
            20                  25                  30

Gly Lys Gln Thr Glu Phe Ile Ile Thr Ala Glu Ile Leu Arg Glu Leu
        35                  40                  45

Ser Met Glu Cys Gly Leu Asn Asn Arg Ile Arg Met Ile Gly Gln Ile
    50                  55                  60

Cys Glu Val Ala Lys Thr Lys Lys Phe Glu Glu His Ala Val Glu Ala
65                  70                  75                  80

Leu Trp Lys Ala Val Ala Asp Leu Leu Gln Pro Glu Arg Pro Leu Glu
                85                  90                  95

Ala Arg His Ala Val Leu Ala Leu Leu Lys Ala Ile Val Gln Gly Gln
            100                 105                 110

Gly Glu Arg Leu Gly Val Leu Arg Ala Leu Phe Phe Lys Val Ile Lys
        115                 120                 125

Asp Tyr Pro Ser Asn Glu Asp Leu His Glu Arg Leu Glu Val Phe Lys
    130                 135                 140

Ala Leu Thr Asp Asn Gly Arg His Ile Thr Tyr Leu Glu Glu Glu Leu
145                 150                 155                 160

Ala Asp Phe Val Leu Gln Trp Met Asp Val Gly Leu Ser Ser Glu Phe
                165                 170                 175

Leu Leu Val Leu Val Asn Leu Val Lys Phe Asn Ser Cys Tyr Leu Asp
            180                 185                 190

Glu Tyr Ile Ala Arg Met Val Gln Met Ile Cys Leu Leu Cys Val Arg
        195                 200                 205

Thr Ala Ser Ser Val Asp Ile Glu Val Ser Leu Gln Val Leu Asp Ala
    210                 215                 220

Val Val Cys Tyr Asn Cys Leu Pro Ala Glu Ser Leu Pro Leu Phe Ile
225                 230                 235                 240

Val Thr Leu Cys Arg Thr Ile Asn Val Lys Glu Leu Cys Glu Pro Cys
                245                 250                 255

Trp Lys Leu Met Arg Asn Leu Leu Gly Thr His Leu Gly His Ser Ala
            260                 265                 270

Ile Tyr Asn Met Cys His Leu Met Glu Asp Arg Ala Tyr Met Glu Asp
        275                 280                 285

Ala Pro Leu Leu Arg Gly Ala Val Phe Phe Val Gly Met Ala Leu Trp
    290                 295                 300

Gly Ala His Arg Leu Tyr Ser Leu Arg Asn Ser Pro Thr Ser Val Leu
```

-continued

```
            305                 310                 315                 320
Pro Ser Phe Tyr Gln Ala Met Ala Cys Pro Asn Glu Val Val Ser Tyr
                325                 330                 335
Glu Ile Val Leu Ser Ile Thr Arg Leu Ile Lys Lys Tyr Arg Lys Glu
            340                 345                 350
Leu Gln Val Val Ala Trp Asp Ile Leu Leu Asn Ile Ile Glu Arg Leu
            355                 360                 365
Leu Gln Gln Leu Gln Thr Leu Asp Ser Pro Glu Leu Arg Thr Ile Val
        370                 375                 380
His Asp Leu Leu Thr Thr Val Glu Glu Leu Cys Asp Gln Asn Glu Phe
385                 390                 395                 400
His Gly Ser Gln Glu Arg Tyr Phe Glu Leu Val Glu Arg Cys Ala Asp
                405                 410                 415
Gln Arg Pro Glu Ser Ser Leu Leu Asn Leu Ile Ser Tyr Arg Ala Gln
            420                 425                 430
Ser Ile His Pro Ala Lys Asp Gly Trp Ile Gln Asn Leu Gln Ala Leu
        435                 440                 445
Met Glu Ser Gly Gly Ser Gly Gly Gly Ser Gly Gly Gly Ser Gly
        450                 455                 460
Gly Gly Lys Pro Ile Leu Leu Pro Asn Glu Ser Gln Ser Phe Glu Arg
465                 470                 475                 480
Ser Val Gln Leu Leu Asp Gln Ile Pro Ser Tyr Asp Thr His Lys Ile
                485                 490                 495
Ala Val Leu Tyr Val Gly Glu Gly Gln Ser Asn Ser Glu Leu Ala Ile
            500                 505                 510
Leu Ser Asn Glu His Gly Ser Tyr Arg Tyr Thr Glu Phe Leu Thr Gly
        515                 520                 525
Leu Gly Arg Leu Ile Glu Leu Lys Asp Cys Gln Pro Asp Lys Val Tyr
        530                 535                 540
Leu Gly Gly Leu Asp Val Cys Gly Glu Asp Gly Gln Phe Thr Tyr Cys
545                 550                 555                 560
Trp His Asp Asp Ile Met Gln Ala Val Phe His Ile Ala Thr Leu Met
                565                 570                 575
Pro Thr Lys Asp Val Asp Lys His Arg Cys Asp Lys Lys Arg His Leu
            580                 585                 590
Gly Asn Asp Phe Val Ser Ile Val Tyr Asn Asp Ser Gly Glu Asp Phe
        595                 600                 605
Lys Leu Gly Thr Ile Lys Gly Gln Phe Asn Phe Val His Val Ile Val
        610                 615                 620
Thr Pro Leu Asp Tyr Glu Cys Asn Leu Val Ser Leu Gln Cys Arg Lys
625                 630                 635                 640
Asp Met Glu Gly Leu Val Asp Thr Ser Val Ala Lys Ile Val Ser Asp
                645                 650                 655
Arg Asn Leu Pro Phe Val Ala Arg Gln Met Ala Leu His Ala Asn Met
            660                 665                 670
Ala Ser Gln Val His His Ser Arg Ser Asn Pro Thr Asp Ile Tyr Pro
        675                 680                 685
Ser Lys Trp Ile Ala Arg Leu Arg His Ile Lys Arg Leu Arg Gln Arg
        690                 695                 700
Ile Cys Glu Glu Ala Ala Tyr Ser Asn Pro Ser Leu Pro Leu Val His
705                 710                 715                 720
Pro Pro Ser His Ser Lys Ala Pro Ala Gln Thr Pro Ala Glu Pro Thr
                725                 730                 735
```

```
Pro Gly Tyr Glu Val Gly Gln Arg Lys Arg Leu Ile Ser Ser Val Glu
            740                 745                 750

Asp Phe Thr Glu Phe Val Glu Gln Lys Leu Ile Ser Glu Glu Asp Leu
        755                 760                 765
```

<210> SEQ ID NO 12
<211> LENGTH: 2336
<212> TYPE: DNA
<213> ORGANISM: Artificial Sequence
<220> FEATURE:
<223> OTHER INFORMATION: Synthetic Construct

<400> SEQUENCE: 12

```
gctagcacta gtaccatggc gaaaccgacc agcaaagata gcggcctgaa agaaaaattt      60
aaaattctgc tgggcctggg caccccgcgc ccgaacccgc gcagcgcgga aggcaaacag     120
accgaattta ttattaccgc ggaaattctg cgcgaactga gcatggaatg cggcctgaac     180
aaccgcattc gcatgattgg ccagatttgc gaagtggcga aaaccaaaaa atttgaagaa     240
catgcggtgg aagcgctgtg gaaagcggtg gcggatctgc tgcagccgga acgcccgctg     300
gaagcgcgcc atgcggtgct ggcgctgctg aaagcgattg cgcagggcca gggcgaacgc     360
ctgggcgtgc tgcgcgcgct gttttttaaa gtgattaaag attatccgag caacgaagat     420
ctgcatgaac gcctggaagt gtttaaagcg ctgaccgata cggccgcca tattaccctat    480
ctggaagaag aactggcgga ttttgtgctg cagtggatgg atgtgggcct gagcagcgaa     540
tttctgctgg tgctggtgaa cctggtgaaa tttaacagct gctatctgga tgaatatatt     600
gcgcgcatgg tgcagatgat ttgcctgctg tgcgtgcgca ccgcgagcag cgtggatatt     660
gaagtgagcc tgcaggtgct ggatgcggtg gtgtgctata actgcctgcc ggcggaaagc     720
ctgccgctgt ttattgtgac cctgtgccgc accattaacg tgaaagaact gtgcgaaccg     780
tgctggaaac tgatgcgcaa cctgctgggc acccatctgg ccatagcgc gatttataac     840
atgtgccatc tgatggaaga tcgcgcgtat atggaagatg cgccgctgct gcgcggcgcg     900
gtgttttttg tgggcatggc gctgtggggc gcgatcgcc tgtatagcct gcgcaacagc     960
ccgaccagcg tgctgccgag ctttatcag gcgatggcgt gcccgaacga agtggtgagc    1020
tatgaaattg tgctgagcat acccgcctg attaaaaaat atcgcaaaga actgcaggtg    1080
gtggcgtggg atattctgct gaacattatt gaacgcctgc tgcagcagct gcagaccctg    1140
gatagcccgg aactgcgcac cattgtgcat gatctgctga ccaccgtgga agaactgtgc    1200
gatcagaacg aatttcatgg cagccaggaa cgctattttg aactggtgga acgctgcgcg    1260
gatcagcgcc cggaaagcag cctgctgaac ctgattagct atcgcgcgca gagcattcat    1320
ccggcgaaag atggctggat tcagaacctg caggcgctga tggaatctgg tgggggtagc    1380
ggaggagggt cagggggcgg cagtggaggc ggaaaaccga ttctgctgcc gaacgaaagc    1440
cagagctttg aacgcagcgt gcagctgctg atcagattc cgagctatga tacccataaa    1500
attgcggtgc tgtatgtggg cgaaggccag agcaacagcg aactggcgat ctgagcaac    1560
gaacatggca gctatcgcta taccgaattt ctgaccggcc tgggccgcct gattgaactg    1620
aaagattgcc agccggataa agtgtatctg gcggcctgg atgtgtgcgg cgaagatggc    1680
cagtttacct attgctggca tgatgatatt atgcaggcgg tgtttcatat tgcgaccctg    1740
atgccgacca agatgtgga taacatcgc tgcgataaaa aacgccatct gggcaacgat    1800
tttgtgagca ttgtgtataa cgatagcggc gaagatttta aactgggcac cattaaaggc    1860
```

```
cagtttaact ttgtgcatgt gattgtgacc ccgctggatt atgaatgcaa cctggtgagc    1920
ctgcagtgcc gcaaagatat ggaaggcctg gtggatacca gcgtggcgaa aattgtgagc    1980
gatcgcaacc tgccgtttgt ggcgcgccag atggcgctgc atgcgaacat ggcgagccag    2040
gtgcatcata gccgcagcaa cccgaccgat atttatccga gcaaatggat tgcgcgcctg    2100
cgccatatta aacgcctgcg ccagcgcatt tgcgaagaag cggcgtatag caacccgagc    2160
ctgccgctgg tgcatccgcc gagccatagc aaagcgccgg cgcagacccc ggcggaaccg    2220
accccgggct atgaagtggg ccagcgcaaa cgcctgatta gcagcgtgga agattttacc    2280
gaatttgtgg aacaaaaact catctcagaa gaggatctgt aggcggccgc ctcgag        2336

<210> SEQ ID NO 13
<211> LENGTH: 4
<212> TYPE: PRT
<213> ORGANISM: Artificial Sequence
<220> FEATURE:
<223> OTHER INFORMATION: Synthetic Construct

<400> SEQUENCE: 13

Ser Gly Gly Gly
1
```

GENE THERAPY FOR TUBEROUS SCLEROSIS

CROSS-REFERENCE TO RELATED APPLICATIONS

This application claims priority to U.S. Provisional Application No. 62/507,358, filed on May 17, 2017, which is hereby incorporated by reference in its entirety.

STATEMENT AS TO FEDERALLY FUNDED RESEARCH

This invention was made with government support under Grant No. TS120038 awarded by the Department of Defense. The government has certain rights in the invention.

SEQUENCE LISTING

The instant application contains a Sequence Listing which has been submitted electronically in ASCII format and is hereby incorporated by reference in its entirety. Said ASCII copy, created Mar. 31, 2023, is named 51317-002002_Sequence_Listing_3_31_23_ST25 and is 55,912 bytes in size.

BACKGROUND OF THE INVENTION

Tuberous sclerosis complex (TSC) is a tumor suppressor syndrome inherited in an autosomal dominant manner with an incidence of about 1 in 5,500. Patients inherit a mutation in one allele of the TSC1 gene (encoding hamartin) or the TSC2 gene (encoding tuberin). These proteins together suppress mammalian target of rapamycin complex 1 (mTORC1) activity. If a mutation in the corresponding normal allele occurs during development or in some somatic cells, it results in enlargement and increased proliferation of cells, forming benign tumors (e.g., hamartomas). These tumors can affect a variety of tissues, including the brain, heart, kidneys, skin, and lungs. In the brain, they can cause developmental delay, autism, epilepsy, and hydrocephalus. Life-threatening conditions in TSC include renal angiomyolipomas, which can cause internal bleeding, and lymphangioleiomyomatosis (LAM), which can compromise breathing. Although rapamycin and related drugs have been effective in reducing the size of lesions for some types of tumors, they must be administered continuously and have side effects, including compromised brain development and immune suppression. In addition, some patients do not respond to these medications, or respond initially and then become resistant. Accordingly, there exists a need in the art for improved treatments for TSC.

SUMMARY OF THE INVENTION

The invention provides compositions and methods for treating tuberous sclerosis complex (TSC) caused by mutations in the TSC2 gene. The compositions and methods described herein relate to a condensed tuberin (cTuberin) and nucleic acid molecules encoding cTuberin.

In a first aspect, the invention features a cTuberin including a hamartin binding region and a GTPase-activating protein (GAP) region, but lacking an Akt phosphorylation site Thr 1462.

In some embodiments, the cTuberin has at least 90% sequence identity (e.g., 90%, 91%, 92%, 93%, 94%, 95%, 96%, 97%, 98%, or 99% sequence identity) to SEQ ID NO: 1. In particular embodiments, the cTuberin is SEQ ID NO: 1.

In some embodiments, the hamartin binding region has at least 90% sequence identity (e.g., 90%, 91%, 92%, 93%, 94%, 95%, 96%, 97%, 98%, or 99% sequence identity) to SEQ ID NO: 2. In particular embodiments, the hamartin binding region is SEQ ID NO: 2.

In some embodiments, the GAP region has at least 90% sequence identity (e.g., 90%, 91%, 92%, 93%, 94%, 95%, 96%, 97%, 98%, or 99% sequence identity) to SEQ ID NO: 3. In particular embodiments, the GAP region is SEQ ID NO: 3.

An engineered cTuberin further lacks an Akt phosphorylation site of human tuberin (SEQ ID NO: 10). In particular embodiments, cTuberin lacks amino acids 451-1514 of human tuberin (SEQ ID NO: 10) which includes an Akt phosphorylation site at Thr 1462 of human tuberin.

In yet other embodiments, the cTuberin includes a spacer between the hamartin binding region and GAP region. In some embodiments, the spacer includes at least SGGG (SEQ ID NO: 13). An exemplary spacer is SGGGSGGGSGGGSGGG (SEQ ID NO: 4).

In yet other embodiments, cTuberin is produced using a human tuberin isoform as is disclosed herein.

In a second aspect, the invention features a nucleic acid molecule encoding the cTuberin of any of the foregoing embodiments.

In other embodiments, the nucleic acid molecule is codon optimized for expression in a human cell (e.g., a brain cell, a heart cell, a kidney cell, a skin cell, or a lung cell).

In some embodiments, the nucleic acid molecule is operably linked to a regulatory control sequence. Exemplary regulatory control sequences include, without limitation, a human cytomegalovirus (CMV) promoter, a chicken β-actin (CBA) promoter, a Rous sarcoma virus (RSV) LTR promoter/enhancer, an SV40 promoter, a dihydrofolate reductase promoter, a phosphoglycerol kinase promoter, a CMV immediate/early gene enhancer/CBA promoter, a synapsin promoter, or a glial fibrillary acidic protein (GFAP) promoter. In one working example, the regulatory control sequence includes CMV immediate/early gene enhancer/CBA promoter and a woodchuck hepatitis virus posttranscriptional regulatory element (WPRE).

In other embodiments, the nucleic acid molecule has at least 90% sequence identity (e.g., 90%, 91%, 92%, 93%, 94%, 95%, 96%, 97%, 98%, or 99% sequence identity) to SEQ ID NO: 5. In particular embodiments, the nucleic acid molecule is SEQ ID NO: 5.

In some embodiments, the nucleic acid molecule is operably linked to an expression cassette.

In a third aspect, the invention features a cell or virus including the nucleic acid molecule of any of the foregoing embodiments.

In a fourth aspect, the invention features a composition including the nucleic acid molecule of any of the foregoing embodiments.

In a fifth aspect, the invention features a recombinant adeno-associated virus (rAAV). Such a rAAV includes an AAV capsid and an AAV genome packaged therein, the AAV genome including a nucleic acid molecule capable of expressing cTuberin. For example, the rAAV includes an AAV capsid and an AAV genome packaged therein, the AAV genome including: (a) an AAV 5' inverted terminal repeat (ITR) sequence; (b) a regulatory control sequence; (c) a nucleic acid molecule encoding cTuberin; and (d) an AAV 3' ITR sequence. In another example, the cTuberin includes a hamartin binding region and a GAP region, but lacks an Akt phosphorylation site Thr 1462.

In some embodiments, the AAV capsid is an AAV1, AAV2, AAV3, AAV4, AAV5, AAV6, AAV7, AAV8, AAV9, AAV10, AAV11, or AAV12 capsid, or a variant of any one of the AAV capsids.

In other embodiments, the nucleic acid molecule is codon optimized for expression in a human cell. In further embodiments, the nucleic acid molecule has at least 90% sequence identity to SEQ ID NO: 5. In particular embodiments, the nucleic acid molecule is SEQ ID NO: 5.

In other embodiments, the nucleic acid is operably linked to a regulatory control sequence. Exemplary regulatory control sequences include, without limitation, a human cytomegalovirus (CMV) promoter, a chicken β-actin (CBA) promoter, a Rous sarcoma virus (RSV) LTR promoter/enhancer, an SV40 promoter, a dihydrofolate reductase promoter, a phosphoglycerol kinase promoter, a CMV immediate/early gene enhancer/CBA promoter, a synapsin promoter, or a glial fibrillary acidic protein (GFAP) promoter.

In some embodiments, the nucleic acid molecule includes an inverted terminal repeat (ITR). In some embodiments, the nucleic acid molecule includes a polyadenylation signal such as a poly A region.

In a sixth aspect, the invention features a composition including the rAAV of any one of the foregoing embodiments and a pharmaceutically acceptable carrier.

In a seventh aspect, the invention features a method of treating a patient having tuberous sclerosis complex (TSC), the method including administering to the patient a cTuberin including a hamartin binding region and a GAP region, but lacking an Akt phosphorylation site Thr 1462.

In some embodiments, the patient is administered a nucleic acid molecule encoding cTuberin.

In some embodiments, the patient is administered a rAAV of any of the preceding aspects.

In some embodiments, the patient is administered extracellular vesicles (EVs) including the nucleic acid molecule of any of the preceding aspects.

In some embodiments, the patient has a renal angiomyolipoma. In some embodiments, the cTuberin is administered intravascularly or is administered into the renal artery or vein.

In other embodiments, the patient has a lymphangioleiomyomatosis (LAM). In some embodiments, the cTuberin is administered intravascularly or is administered into the lungs.

In yet other embodiments, the patient has a brain dysfunction. In some embodiments, the cTuberin is administered intravascularly, intracerebrally, or intrathecally.

In some embodiments, the cTuberin is administered to a renal angiomyolipoma, a LAM, or the brain.

In some embodiments, the rAAV is administered to a brain cell, a heart cell, a kidney cell, a skin cell, or a lung cell. In yet other embodiments, the rAAV is administered intravascularly, intravenously, intracerebrally, intraventricularly, intrathecally, or dermally.

In some embodiments, the patient is further administered a drug used to treat TSC. Such a drug may be rapamycin or a rapamycin analog.

Definitions

As used herein, "administering" or a grammatical derivation thereof refers to the placement of an agent as disclosed herein into a subject by a method or route which results in at least partial localization of the agent at a desired site.

As used herein, "codon optimization" refers to modifying a nucleic acid sequence to change individual nucleic acids without any resulting change in the encoded amino acid. Sequences modified in this way are referred to herein as "codon optimized." This process may be performed on any of the sequences described in this specification to enhance expression or stability. Codon optimization may be performed in a manner such as that described in, e.g., U.S. Pat. Nos. 7,561,972, 7,561,973, and 7,888,112, each of which is incorporated herein by reference in its entirety. The sequence surrounding the translational start site can be converted to a consensus Kozak sequence according to known methods. See, e.g., Kozak et al, Nucleic Acids Res. 15(20): 8125-8148 (1987), incorporated herein by reference in its entirety.

As used herein, a sequence which "encodes" a particular protein is a nucleic acid molecule that is transcribed (in the case of DNA) and translated (in the case of mRNA) into a polypeptide in vitro or in vivo when placed under the control of appropriate regulatory sequences; although one of skill in the art will readily appreciate that various polynucleotides do not operate in this fashion (e.g., antisense RNA, siRNA, ribozymes, wherein the RNA transcript is the product). With respect to protein products (i.e., not RNA products), the boundaries of the coding sequence are determined by a start codon at the 5' (i.e., amino) terminus and a translation stop codon at the 3' (i.e., carboxy) terminus. A gene can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the gene sequence. Moreover, a "gene" (i) starts with a promoter region containing multiple regulatory elements, possibly including enhancers, for directing transcription of the coding region sequences; (ii) includes coding sequences, which start at the transcriptional start site that is located upstream of the translational start site and ends at the transcriptional stop site, which may be quite a bit downstream of the stop codon (a polyadenylation signal is usually associated with the transcriptional stop site and is located upstream of the transcriptional stop); and (iii) may contain introns and other regulatory sequences to modulate expression and improve stability of the RNA transcript. Still in accordance with the present invention, a "gene" may refers to a sequence encoding a protein.

As used herein, "expression" refers to the process by which a structural gene produces a polypeptide. It involves transcription of the gene into mRNA, and the translation of such mRNA into polypeptides(s).

As used herein, an "expression vector" is a vector or vehicle similar to a cloning vector but which is capable of expressing a gene which has been cloned into it after transformation into a host. The cloned gene is usually placed under the control of (i.e., operably linked to) certain control sequences such as promoter sequences. Expression control sequences will vary depending on whether the vector is designed to express the operably linked gene in a prokaryotic or eukaryotic host and can additionally contain transcriptional elements such as enhancer elements, termination sequences, tissue-specificity elements, and/or translational initiation and termination sites.

As used herein, "nucleic acid" or "nucleic acid molecule," as generally understood and used herein, refers to chains of nucleotides joined together by phosphodiester bonds to form a nucleic acid heteropolymer. The nucleic acid molecules can be double stranded or single stranded and can be deoxyribonucleotide (DNA) molecules, such as cDNA or genomic DNA, or ribonucleotide (RNA) molecules. As such, the nucleic acid molecule can include one or more exons, with or without, as appropriate, introns.

As used herein, "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. Additionally, two portions of a transcription regulatory element are operably linked to one another if they are joined such that the transcription-activating functionality of one portion is not adversely affected by the presence of the other portion. Two transcription regulatory elements may be operably linked to one another by way of a linker nucleic acid (e.g., an intervening non-coding nucleic acid) or may be operably linked to one another with no intervening nucleotides present.

As used herein, "percent identity" between two sequences is determined by the BLAST 2.0 algorithm, which is described in Altschul et al., (1990) J. Mol. Biol. 215:403-410. Software for performing BLAST analyses is publicly available through the National Center for Biotechnology Information.

As used herein, "pharmaceutically acceptable" refers to those compounds, materials, compositions and/or dosage forms, which are suitable for contact with the tissues of a subject, such as a mammal (e.g., a human) without excessive toxicity, irritation, allergic response and other problem complications commensurate with a reasonable benefit/risk ratio.

As used herein, "protein" and "polypeptide" are used interchangeably herein and refer to a polymer of amino acids. A peptide is a relatively short polypeptide, typically between about 2 and 60 amino acids in length. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

As used herein, "regulatory control element" or "regulatory control sequence" refers collectively to promoter regions, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. These control elements need not always be present, so long as the selected coding sequence is capable of being replicated, transcribed and translated in an appropriate host cell.

As used herein, "recombinant virus" refers to a virus that has been genetically altered (e.g., by the addition or insertion of a heterologous nucleic acid construct into the particle).

As used herein, the terms "subject" and "patient" are interchangeable and refer to an organism that receive treatment for a particular disease or condition as described herein.

As used herein, "treat," "treatment," "treating," or "amelioration" are used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease-state is reduced or halted. That is, "treatment" includes not just the improvement of symptoms or markers, but also a cessation or at least slowing of progress or worsening of symptoms that would be expected in the absence of treatment. For example, in the case of renal angiomyolipomas, tumor size can be monitored by MRI and the shrinkage in cell size due to replacement of tuberin function can be revealed according to standard procedures (e.g., such as those used to monitor treatment of TSC using rapamycin).

Beneficial or desired clinical results include, but are not limited to, alleviation of one or more symptom(s), diminishment of extent of the deficit, stabilized (i.e., not worsening) state of tuberous sclerosis complex progression, delay or slowing of invasiveness or growth of tumors or hamartomas, and amelioration or palliation of symptoms associated with such tumors or hamartomas. Treatment also includes a decrease in mortality or an increase in the lifespan of a subject as compared to one not receiving the treatment.

As used herein, "vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

Unless otherwise defined herein, scientific and technical terms used regarding the present application shall have the meanings that are commonly understood by those of ordinary skill in the art to which this disclosure belongs. This invention is not limited to the particular methodology, protocols, and reagents, etc., described herein and as such can vary. The terminology used herein is for describing particular embodiments only, and is not intended to limit the scope of the present invention, which is defined solely by the claims.

The invention described herein provides numerous advantages. For example, described herein are compositions and methods useful for treating tuberous sclerosis complex by gene therapy using recombinant adeno-associated viruses. Previously, TSC caused by mutations in TSC2 were not corrected with gene therapy due to the relatively small insert capacity of an AAV vector of 4.7 kb compared to the 5.4 kb cDNA of human tuberin. As is described herein, the disclosed methods for correcting mutations in TSC2 utilizes a condensed form of human tuberin, cTuberin. The cDNA of the cTuberin described herein is about 2.3 kb, which is readily expressed in an AAV vector. Indeed, AAV vectors have proven safe and beneficial in gene therapy. These vectors can be delivered, e.g., intravascularly to reach many tissues in a single injection, with some serotypes able to cross the blood brain barrier. Typically, a single injection confers beneficial outcome over a long term. Our compositions and methods allow for the use of AAV vectors expressing cTuberin for treatment of manifestations of tuberous sclerosis complex in patients with mutations in TSC2. Such vectors are not only useful for treating renal angiomyolipomas, but also for LAM and brain dysfunctions resulting from TSC2.

Further, the invention provides an alternative method of treating TSC not necessarily requiring rapamycin or its analogues, which may cause toxicity and adverse events related to over-suppression of mTORC1. Instead, the disclosed compositions and methods employ the functionality of tuberin, which is only active when complexed with hamartin. Because hamartin levels are normal in TSC2 patients, it is envisioned that there is little-to-low toxicity due to overexpression of cTuberin through vector delivery. Additionally, while rapamycin and related drugs can inhibit mTORC1 activity, cTuberin is capable of inhibiting both mTORC1 and mTORC1-independent Rheb-dependent pathological actions, and is therefore potentially more efficacious than previous therapies for tuberous sclerosis.

Other features and advantages of the invention will be apparent from the following description of the preferred embodiments thereof, and from the claims.

BRIEF DESCRIPTION OF THE DRAWINGS

FIG. 1A shows the amino acid sequence of cTuberin (SEQ ID NO: 1).

FIG. 1B shows the nucleic acid sequence encoding cTuberin (SEQ ID NO: 5).

FIG. 3B is a Western blot showing the expression levels of pS6, S6, and GAPDH in cells transfected with various constructs. pS6 expression was elevated in the cells lacking cTuberin activity.

FIG. 5A show the staining in a normal, non-injected mice (control); FIGS. 5B-5E show the staining in mice injected at P0 with AAV1-CBA-Cre vector, and FIG. 5F shows the staining for the mice further treated at P3 with AAV1-CBA-cTuberin.

FIG. 6B is a graph showing the growth of LAM tumors in non-injected mice and mice injected with AAV9-CBA-cTuberin at weeks 4 and 9.

DETAILED DESCRIPTION OF THE EMBODIMENTS OF THE INVENTION

Figure 2A:
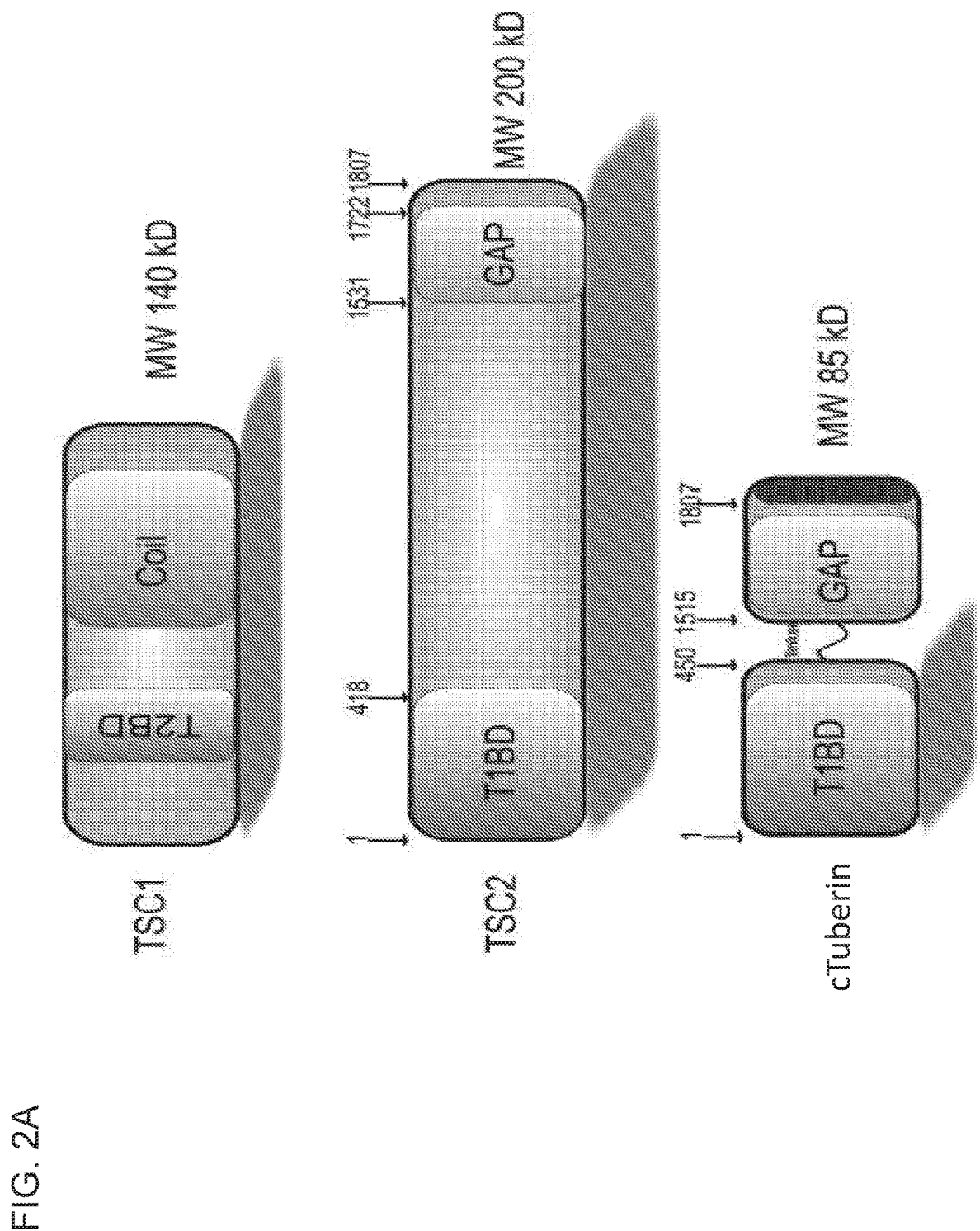
FIG. 2A is a schematic diagram of the functional domains of the TSC1 and TSC2 full-length human proteins and the condensed tuberin (cTuberin) protein. Amino acid residues are indicated by the numbers above the arrows. T2BD refers to the TSC2-binding domain, T1BD refers to the TSC1-binding domain, coil refers to the predicted coiled-coil domain, and GAP refers to GTPase-activating protein, which is a domain in human tuberin homologous to that in Rap1GAP.
Figure 2B:
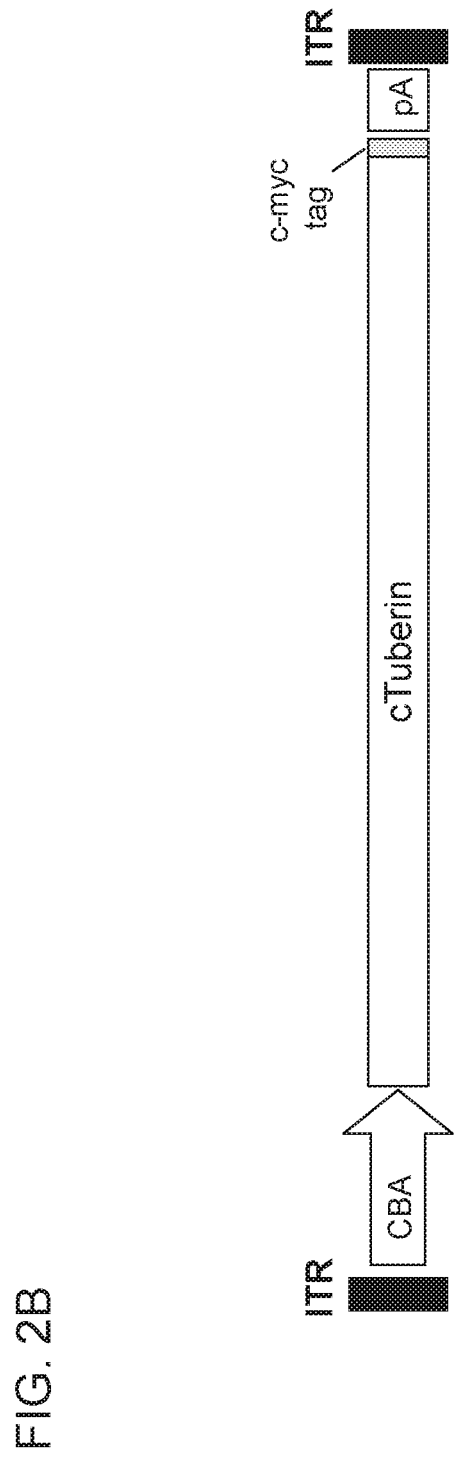
FIG. 2B is a schematic diagram of the cTuberin AAV vector.

Systemic gene therapy, as is disclosed herein, can be achieved in TSC patients by delivery (e.g., via the vascular system) of a condensed tuberin (cTuberin) such as one encoded in an AAV vector, which is useful for decreasing the size of affected cells and reduction of hamartomas in multiple tissues, including throughout the central nervous system, kidneys, and lungs. cTuberin is useful, for example, for its ability to suppress mTOR activity. Useful forms of cTuberin may be identified according to any method, e.g., by testing their ability to suppress S6 phosphorylation in cells in vitro lacking tuberin as is described herein. Below we describe a useful design of a cTuberin in treating TSC.

In the Examples below, we describe engineering a condensed version of human tuberin, termed cTuberin, which fits into an AAV vector. The size of human tuberin cDNA is 5.4 kb, exceeding the transgene packaging capacity of AAV. To this end, engineering our condensed form of tuberin was accomplished by deleting the central portion of the human tuberin cDNA. Our cTuberin retains the hamartin binding region in the N-terminal and the GAP region in the C-terminal of human tuberin, but lacks an Akt phosphorylation site Thr1462, such that Akt activation of mTORC1 is decreased or eliminated. The central region of the protein is replaced by a glycine-serine linker to confer conformational flexibility. This cTuberin cDNA was then cloned into an AAV vector under a strong ubiquitous chicken beta actin promoter. We have transduced mouse embryonic fibroblasts with this AAV-CBA-cTuberin construct and as is shown by Western blot analysis that it reduces S6 kinase activity, which is a marker of mTORC1 activation, thus establishing biologic activity of cTuberin.

I. cTuberin cTuberin, as is described herein, in general, includes a hamartin binding region, a GTPase-activating protein (GAP) region, and a spacer linking the hamartin binding region to the GAP region, and lacks the Akt phosphorylation site at Thr 1462 of human tuberin.

An exemplary cTuberin useful for treating TSC has the amino acid sequence of SEQ ID NO: 1. In this cTuberin (SEQ ID NO: 1), the amino acid sequence of the hamartin binding region is SEQ ID NO: 2. Also in this cTuberin (SEQ ID NO: 1), the amino acid sequence of the GAP region is SEQ ID NO: 3.

The hamartin binding region and GAP region of this cTuberin (SEQ ID NO: 1) are connected by a protein spacer sequence. In one example, the spacer sequence includes a glycine-serine (SGGG) (SEQ ID NO: 13) linker sequence. In this instance, a 16 a.a. linker connects the hamartin binding region and the GAP region. The cTuberin protein relative to human tuberin (SEQ ID NO: 10) lacks the Akt phosphorylation site Thr 1462 of human tuberin, which is one of several phosphorylation sites involved in the regulation of tuberin activity (Huang et al., *Biochem. J.* 412(2): 179-190 2008).

In another example, cTuberin has at least 80% sequence identity (e.g., 80%, 85%, 90%, 91%, 92%, 93%, 94%, 95%, 96%, 97%, 98%, or 99% sequence identity) to SEQ ID NO: 1. Of this cTuberin, the hamartin binding region of cTuberin has at least 80% sequence identity (e.g., 80%, 85%, 90%, 91%, 92%, 93%, 94%, 95%, 96%, 97%, 98%, or 99% sequence identity) to SEQ ID NO: 2, and the GAP region of cTuberin has at least 80% sequence identity (e.g., 80%, 85%, 90%, 91%, 92%, 93%, 94%, 95%, 96%, 97%, 98%, or 99% sequence identity) to SEQ ID NO: 3. In some cTuberins, the hamartin binding region and GAP region of cTuberin are connected by a protein spacer sequence. In one example, the spacer sequence includes a glycine-serine (SGGG) linker sequence, (SEQ ID NO: 13) linker sequence.

The cTuberin of SEQ ID NO: 1 described herein was produced using human tuberin, the amino acid and nucleic acid sequences of which can be found at NCBI Accession No. NP_000539.2 and GenBank Accession No. X75621.1, respectively. Other human tuberin isoforms may also be used for producing additional cTuberins. Exemplary human tuberin isoforms useful to produce such molecules include, but are not limited to, tuberin isoform 4 (NCBI Accession No. NP_001070651.1), tuberin isoform 5 (NCBI Accession No. NP_001107854.1), tuberin isoform 6 (NCBI Accession No. NP_001305756.1), tuberin isoform 7 (NCBI Accession No. NP_001305758.1), tuberin isoform 8 (NCBI Accession No. NP_001305760.1), tuberin isoform 9 (NCBI Accession No. NP_001305761.1), tuberin isoform X7 (NCBI Accession No. XP_024306181.1), tuberin isoform X8 (NCBI Accession No. XP_005255586.2), tuberin isoform X9 (NCBI Accession No. XP_016879105.1), tuberin isoform X10 (NCBI Accession No. XP_005255588.2), tuberin isoform X11 (NCBI Accession No. XP_016879106.1), tuberin isoform X12 (NCBI Accession No. XP_016879107.1), and others. Such tuberins are useful for engineering any cTuberin as described herein.

For example, a cTuberin can be engineered using human tuberin isoform 4 (NCBI Accession No. NP_001070651.1). Using human tuberin isoform 4, the amino acid sequence of a hamartin binding region having at least 80% (e.g., 80%, 85%, 90%, 91%, 92%, 93%, 94%, 95%, 96%, 97%, 98%, or 99% sequence identity) sequence identity to SEQ ID NO: 2 and the amino acid sequence of a GAP region having at least 80% (e.g., 80%, 85%, 90%, 91%, 92%, 93%, 94%, 95%, 96%, 97%, 98%, or 99% sequence identity) sequence identity to SEQ ID NO: 3 are produced as described for cTuberin (SEQ ID NO:1). Further, the hamartin binding and GAP regions can be connected by a protein spacer sequence. In one example, the spacer sequence includes a glycine-serine (SGGG) linker sequence, e.g., SEQ ID NO: 4. A cTuberin engineered from human tuberin isoform 4 further lacks an Akt phosphorylation site.

II. cTuberin Nucleic Acid Molecules

Further, the exemplary cTuberin of SEQ ID NO: 1 is encoded by a nucleic acid molecule having the sequence of SEQ ID NO: 5. In this cTuberin nucleic acid molecule (SEQ ID NO: 5), the hamartin binding region is encoded by SEQ ID NO: 6. Also in this cTuberin nucleic acid molecule (SEQ ID NO: 5), the GAP region is encoded by SEQ ID NO: 7.

In this exemplary cTuberin of SEQ ID NO: 1, encoded by the nucleic acid molecule of SEQ ID NO: 5, the hamartin binding region and GAP region are linked by a protein spacer sequence, i.e., a glycine-serine linker of SEQ ID NO: 4. The glycine-serine linker is encoded by SEQ ID NO: 8.

In a further embodiments, the cTuberin encoding nucleic acid has at least 80% sequence identity (e.g., 80%, 85%, 90%, 91%, 92%, 93%, 94%, 95%, 96%, 97%, 98%, or 99% sequence identity) to SEQ ID NO: 5. Of this cTuberin, the hamartin binding region is encoded by a nucleic acid having at least at least 80% sequence identity (e.g., 80%, 85%, 90%, 91%, 92%, 93%, 94%, 95%, 96%, 97%, 98%, or 99% sequence identity) to SEQ ID NO: 6, and the GAP region is encoded by a nucleic acid having at least at least 80% sequence identity (e.g., 80%, 85%, 90%, 91%, 92%, 93%, 94%, 95%, 96%, 97%, 98%, or 99% sequence identity) to SEQ ID NO: 7. Further, the cTuberin encoding nucleic acid may include a protein spacer encoding sequence, for example, SEQ ID NO: 8.

The cTuberin nucleic acid molecule may be codon optimized for expression in a human cell. Further, the cTuberin nucleic acid molecule may be operably linked to a regulatory control sequence, such as, for example, a CMV immediate/early gene enhancer/CBA promoter and a woodchuck hepatitis virus posttranscriptional regulatory element (WRPE), or, without limitation, a human cytomegalovirus (CMV) promoter, a chicken β-actin (CBA) promoter, a Rous sarcoma virus (RSV) LTR promoter/enhancer, an SV40 promoter, a dihydrofolate reductase promoter, a phosphoglycerol kinase promoter, a CMV immediate/early gene enhancer/CBA promoter, a synapsin promoter, or a glial fibrillary acidic protein (GFAP) promoter. The nucleic acid molecule may also be operably linked to an expression cassette.

For example, the cTuberin nucleic acid molecule (SEQ ID NO: 5) may be inserted under a CBA promoter with a Kozak sequence followed by a wood chuck hepatitis virus post-transcriptional regulatory element (WPRE) and a SV40 and bovine growth hormone polyadenylation signal sequence. The vector is inserted into an AAV2-LTR backbone and is flanked by AAV2 ITR sequences.

Further, the cTuberin nucleic acid molecule (SEQ ID NO: 5) may be incorporated into a vector plasmid genome. An exemplary vector plasmid genome that includes the cTuberin nucleic acid molecule (SEQ ID NO: 5) has the sequence of SEQ ID NO: 11.

III. Recombinant AAV Molecules

Any suitable nucleic acid vector may be used in conjunction with the present compositions and methods to design and assemble the components of a nucleic acid molecule encoding cTuberin and a recombinant adeno-associated virus (AAV). rAAV vectors useful in the compositions and methods described herein are recombinant nucleic acid constructs that include (1) a heterologous sequence to be expressed (e.g., a nucleic acid molecule encoding cTuberin) and (2) viral sequences that facilitate integration and expression of the heterologous genes. The viral sequences may include those sequences of AAV that are required in cis for replication and packaging (e.g., functional ITRs) of the DNA into a virion. Such rAAV vectors may also contain marker or reporter genes. Useful rAAV vectors have one or more of the AAV WT genes deleted in whole or in part, but retain functional flanking ITR sequences. The AAV ITRs may be of any serotype suitable for a particular application. Methods for using rAAV vectors are described, for example, in Tal et al., *J. Biomed. Sci.* 7:279-291 (2000), and Monahan et al., *Gene Therapy.* 7:24-30 (2000), the disclosures of each of which are incorporated herein by reference as they pertain to AAV vectors for gene delivery.

In one embodiment, the vector is a recombinant AAV carrying the cTuberin nucleic acid molecule and driven by a promoter that expresses a cTuberin molecule in selected cells of a subject. Methods for assembly of the recombinant vectors are known in the art. See, e.g., Ausubel et al., *Current Protocols in Molecular Biology*, John Wiley & Sons, New York, 1989; Kay, M. A. et al., *Nat. Med.* 7(1):33-40 (2001); and Walther W. and Stein U., *Drugs* 2000, 60(2):249-71.

In certain embodiments described herein, the cTuberin nucleic acid molecule is delivered to the selected cells, e.g., a brain, heart, kidney, skin, or lung cell, in need of treatment by means of an AAV vector according to standard methods known in the art. More than 30 naturally occurring serotypes of AAV are available. Many natural variants in the AAV capsid exist, allowing identification and use of an AAV with properties specifically suited for the selected cells. AAV viruses may be engineered by conventional molecular biology techniques, making it possible to optimize these particles for cell specific delivery of the cTuberin nucleic acid molecule sequences, for minimizing immunogenicity, for tuning stability and particle lifetime, for efficient degradation, for accurate intracellular delivery, e.g., to the nucleus.

The expression of the cTuberin nucleic acid molecules described herein can be achieved in the selected cells through delivery by recombinantly engineered AAVs or artificial AAVs that contain sequences encoding the desired cTuberin nucleic acid molecule. The use of AAVs is a common mode of exogenous delivery of DNA as it is relatively non-toxic, provides efficient gene transfer, and can be easily optimized for specific purposes. Among the well-characterized serotypes of AAVs isolated from human or non-human primates, human serotype 2 has been widely used for efficient gene transfer experiments in different target tissues and animal models. Other AAV serotypes include, but are not limited to, AAV1, AAV3, AAV4, AAV5, AAV6, AAV7, AAV8, AAV9, AAV10, AAV11, AAV12, or a hybrid serotype thereof. Unless otherwise specified, the AAV ITRs, and other selected AAV components described herein, may be readily selected from among any AAV serotype, including, without limitation, AAV1, AAV2, AAV3, AAV4, AAV5, AAV6, AAV7, AAV8, AAV9, AAV10, AAV11, AAV12, a hybrid serotype thereof, or other known and unknown AAV serotypes. In one embodiment, the ITRs are from AAV2. These ITRs or other AAV components may be readily isolated using techniques available to those of skill in the art from an AAV serotype. Such AAV may be isolated or obtained from academic, commercial, or public sources (e.g., the American Type Culture Collection, Manassas, VA). Alternatively, the AAV sequences may be obtained through synthetic or other suitable means by reference to published sequences such as are available in the literature or in databases such as, e.g., GenBank, PubMed, or the like.

Desirable AAV fragments for assembly into vectors include the cap proteins, including the vp1, vp2, vp3, and hypervariable regions, the rep proteins, including rep 78, rep 68, rep 52, and rep 40, and the sequences encoding these proteins. These fragments may be readily utilized in a variety of vector systems and host cells. Such fragments may be used alone, in combination with other AAV serotype sequences or fragments, or in combination with elements from other AAV or non-AAV viral sequences. As used herein, artificial AAV serotypes include, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a pseudotyped AAV, a chimeric AAV capsid, a recombinant AAV capsid, or a "humanized" AAV capsid. Pseudotyped vectors, wherein the capsid of one AAV is utilized with the ITRs from an AAV having a different capsid protein, are useful in the compositions and methods described herein.

In one example, the AAV includes a capsid sequence derived from AAV1. In another embodiment, the AAV includes a capsid sequence derived from AAV9. The use of AAV1 and AAV9 have been previously described in Broekman et al., *Neuroscience.* 138:501-510, 2006, which is incorporated herein by reference.

In another example, the vectors useful in compositions and methods described herein contain, sequences encoding a selected AAV serotype capsid, e.g., an AAV1 or AAV9 capsid, or a fragment thereof. Other useful vectors contain, sequences encoding a selected AAV serotype rep protein, e.g., AAV1 or AAV9 rep protein, or a fragment thereof. Optionally, such vectors may contain both AAV cap and rep proteins. In vectors in which both AAV rep and cap are provided, the AAV rep and AAV cap sequences can both be of one serotype origin, e.g., an AAV1 or AAV9 origin.

Alternatively, vectors may be used in which the rep sequences are from an AAV serotype which differs from that which is providing the cap sequences. In one embodiment, the rep and cap sequences are expressed from separate sources (e.g., separate vectors, or a host cell and a vector). In another embodiment, these rep sequences are fused in frame to cap sequences of a different AAV serotype to form a chimeric AAV vector described in U.S. Pat. No. 7,282,199, which is incorporated by reference herein.

A suitable recombinant AAV (rAAV) is generated by culturing a host cell which contains a nucleic acid sequence encoding an AAV serotype capsid protein, or fragment thereof, as defined herein; a functional rep gene; a minigene composed of, e.g., AAV ITRs and the cTuberin nucleic acid sequence; and sufficient helper functions to permit packaging of the minigene into the AAV capsid protein. The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art.

In one working example, the AAV includes a promoter (or a functional fragment of a promoter). The selection of the promoter to be employed in the rAAV may be made from among a wide number of constitutive or inducible promoters that can express the selected transgene in the desired target cell, which are known in the art. In one embodiment, the promoter is cell-specific. The term "cell-specific" means that the particular promoter selected for the recombinant vector can direct expression of the selected transgene in a particular cell type. In one embodiment, the promoter is specific for expression of the transgene in a brain cell, a heart cell, a kidney cell, a skin cell, or a lung cell.

In another embodiment, the promoter is the native promoter for the target gene to be expressed. Useful promoters include, without limitation, human cytomegalovirus (CMV) promoter, chicken β-actin (CBA) promoter, Rous sarcoma virus (RSV) LTR promoter/enhancer, SV40 promoter, dihydrofolate reductase promoter, phosphoglycerol kinase promoter, CMV-immediate early (IE) enhancer/CBA promoter, synapsin promoter, and glial fibrillary acidic protein (GFAP) promoter.

Other conventional regulatory sequences contained in the minigene or rAAV are known in the art. One of skill in the art may make a selection among these, and other, expression control sequences without departing from the scope described herein An AAV minigene may include the cTuberin nucleic acid molecule described herein and its regulatory sequences, and 5' and 3' AAV ITRs. In one embodiment, the ITRs of AAV serotype 2 are used. However, ITRs from other suitable serotypes may be selected. In some embodiments, the minigene is packaged into a capsid protein and delivered to a selected host cell.

The minigene, rep sequences, cap sequences, and helper functions required for producing the rAAV may be delivered to the packaging host cell in the form of any genetic element which transfers the sequences carried thereon. The selected genetic element may be delivered by any suitable method, including those described herein. The methods used to construct any embodiment described herein are known to those with skill in nucleic acid manipulation and include genetic engineering, recombinant engineering, and synthetic techniques. See, e.g., Sambrook et al., *Molecular Cloning: A Laboratory Manual*, Cold Spring Harbor Press, Cold Spring Harbor, NY. Similarly, methods of generating rAAV virions are well known and the selection of a suitable method is not a limitation on the present invention. See, e.g., K. Fisher et al., *J. Virol.*, 1993 70: 520-532 and U.S. Pat. No. 5,478,745, each of which is incorporated by reference herein.

In another working example, a cTuberin minigene is prepared in a proviral plasmid, such as those disclosed in International Patent Publication No. WO 2012/158757, incorporated herein by reference. Such a proviral plasmid contains a modular recombinant AAV genome comprising in operative association comprising: a wildtype 5' AAV2 ITR sequence flanked by unique restriction sites that permit ready removal or replacement of said ITR; a promoter comprising a cytomegalovirus sequence upstream of a cytomegalovirus (CMV)-chicken beta actin sequence, or a cell-specific promoter/enhancer, the promoter flanked by unique restriction sites that permit ready removal or replacement of the entire promoter sequence, and the upstream sequence flanked by unique restriction sites that permit ready removal or replacement of only the upstream CMV or enhancer sequence, from the promoter sequence. The cTuberin nucleic acid molecule described herein can be inserted into the site of a multi-cloning poly linker, wherein the cTuberin nucleic acid molecule is operatively linked to, and under the regulatory control of, the promoter. A bovine growth hormone polyadenylation sequence flanked by unique restriction sites that permit ready removal or replacement of said poly A sequence; and a wildtype 3' AAV2 ITR sequence flanked by unique restriction sites that permit ready removal or replacement of the 3' ITR; are also part of this plasmid. The plasmid backbone comprises the elements necessary for replication in bacterial cells and is itself flanked by transcriptional terminator/insulator sequences.

In yet another working example, a proviral plasmid comprises a modular recombinant AAV genome comprising in operative association comprising: (i) a wildtype 5' AAV2 ITR sequence flanked by unique restriction sites that permit ready removal or replacement of said ITR; (ii) a promoter comprising (A) a CMV immediate/early enhancer sequence upstream of a CMV-chicken beta actin sequence; or (B) a cell-specific promoter/enhancer including, for example, a human cytomegalovirus (CMV) promoter, a chicken β-actin (CBA) promoter, a Rous sarcoma virus (RSV) LTR promoter/enhancer, an SV40 promoter, a dihydrofolate reductase promoter, a phosphoglycerol kinase promoter, a CMV immediate/early gene enhancer/CBA promoter, a synapsin promoter, or a glial fibrillary acidic protein (GFAP) promoter, and others. The promoter is flanked by unique restriction sites that permit ready removal or replacement of the entire promoter sequence, and the upstream sequence flanked by unique restriction sites that permit ready removal or replacement of only the upstream CMV or enhancer sequence, from the promoter sequence. Also part of this proviral plasmid is a multi-cloning polylinker sequence that permits insertion of a cTuberin nucleic acid sequence including any of those described herein, wherein the cTuberin nucleic acid molecule is operatively linked to, and under the regulatory control of, the promoter; a bovine growth hormone polyadenylation sequence flanked by unique restriction sites that permit ready removal or replacement of said poly A sequence; and a wildtype 3' AAV2 ITR sequence flanked by unique restriction sites that permit ready removal or replacement of the 3' ITR. The proviral plasmid also contains a plasmid backbone comprising the elements necessary for replication in bacterial cells, and further comprising a kanamycin resistance gene, said plasmid backbone flanked by transcriptional terminator/insulator sequences. The proviral plasmid described herein may also contain in the plasmid backbone a non-coding lambda phage 5.1 kb stuffer sequence to increase backbone length and prevent reverse packaging of non-functional AAV genomes.

In some embodiments, a proviral plasmid contains multiple copies of a cTuberin nucleic acid molecule. For example, cTuberin nucleic acid molecules that are less than half the packaging limit for AAV can therefore be repeated once, twice, three times, four times, five times, six times, seven times, eight times, nine times, 10 times, 11 times, 12 times, 13 times, 14 times, 15 times, 16 times, 17 times, 18 times, 19 times, 20 times, or more on a single proviral plasmid.

In yet a further aspect, the promoter of the proviral plasmid is modified to reduce the size of the promoter to permit larger cTuberin nucleic acid molecule sequences to be inserted in the rAAV. In one embodiment, the CMV/CBA hybrid promoter, which normally includes a non-coding exon and intron totaling about 1,000 base pairs, is replaced with a 130-base pair chimeric intron, as is known in the art.

These proviral plasmids are then employed in currently conventional packaging methodologies to generate a recombinant virus expressing the cTuberin molecule transgene carried by the proviral plasmids. Suitable production cell lines are readily selected by one of skill in the art. For example, a suitable host cell can be selected from any biological organism, including prokaryotic (e.g., bacterial) cells, and eukaryotic cells, including, insect cells, yeast cells and mammalian cells. Briefly, the proviral plasmid is transfected into a selected packaging cell, where it may exist transiently. Alternatively, the minigene or gene expression cassette with its flanking ITRs is stably integrated into the genome of the host cell, either chromosomally or as an episome. Suitable transfection techniques are known and may readily be utilized to deliver the recombinant AAV genome to the host cell. Typically, the proviral plasmids are cultured in the host cells which express the cap and/or rep proteins. In the host cells, the minigene consisting of the cTuberin nucleic acid molecule with flanking AAV ITRs is rescued and packaged into the capsid protein or envelope protein to form an infectious viral particle. Thus, a recombinant AAV infectious particle is produced by culturing a packaging cell carrying the proviral plasmid in the presence of sufficient viral sequences to permit packaging of the gene expression cassette viral genome into an infectious AAV envelope or capsid.

IV. Extracellular Vesicles

Extracellular vesicles (EVs) are useful in the methods and compositions described herein. For example, EVs including any cTuberin described herein can be administered to a subject according to standard methods. In a further example, EVs including any nucleic acid molecule encoding cTuberin can be administered to a subject as well.

Extracellular vesicles, including but not limited to exosomes, microvesicles, microparticles, circulating microvesicles, shedding microvesicles, nanovesicles, nanoparticles, apoptotic bodies, and membrane vesicles, are fragments of plasma membrane ranging from for example, 20 nm to 10 μm, shed from almost all cell types. Microvesicles play a role in intercellular communication and can transport mRNA, miRNA, and proteins between cells. As will be apparent to a person of skill in the art, there are various EV isolation and purification protocols based on filtration, differential centrifugation, ultracentrifugation, flotation of vesicles in gradients (sucrose, OptiPrep™), and immunoaffinity capture utilizing antibodies against membrane proteins. Exemplary information for isolating extracelluar vesicles may be found in Simpson R J, Mathivanan S (2012) Extracellular Microvesicles: The Need for Internationally Recognised Nomenclature and Stringent Purification Criteria. J Proteomics Bioinform 5: ii-ii; van der Pol et al., Classification, functions, and clinical relevance of extracellular vesicles, Pharmacol Rev. 2012 July; 64(3):676-705; Raposo and Stoorvogel, Extracellular vesicles: exosomes, microvesicles, and friends, J Cell Biol. 2013 Feb. 18; 200(4):373-83; and Witwer et al., Standardization of sample collection, isolation and analysis methods in extracellular vesicle research, J Extracell Vesicles. 2013 May 27; 2, which are incorporated herein by reference in their entirety. Also, see Sarkar el al., 2009, Taylor and Gercel-Taylor, 2008, and Balaj et al., 2011, which are incorporated herein by reference in their entirety.

Typically, EVs are loaded according to standard procedures with any of the cTuberins described herein. For example, the EV can be loaded with the cTuberin of SEQ ID NO: 1.

Similarly, EVs are loaded with any of the nucleic acid molecules encoding cTuberin described herein. The nucleic acid molecule may be incorporated into an AAV genome. Further, the nucleic acid molecule can be operably linked to a regulatory control sequence including, for example, a human cytomegalovirus (CMV) promoter, a chicken β-actin (CBA) promoter, a Rous sarcoma virus (RSV) LTR promoter/enhancer, an SV40 promoter, a dihydrofolate reductase promoter, a phosphoglycerol kinase promoter, a CMV immediate/early gene enhancer/CBA promoter, a synapsin promoter, or a glial fibrillary acidic protein (GFAP) promoter. In one example, the regulatory control sequence includes CMV immediate/early gene enhancer/CBA promoter and a woodchuck hepatitis virus posttranscriptional regulatory element (WPRE). In a further example, the nucleic acid molecule can include an ITR. In another example, the nucleic acid molecule includes a poly A.

Any EVs as described herein may also be included in a composition with a pharmaceutically acceptable carrier.

V. Pharmaceutical Compositions and Kits

Provided herein are pharmaceutical compositions including a cTuberin nucleic acid molecule, EVs that includes a cTuberin nucleic acid molecule described herein (e.g., a rAAV), or a rAAV including a cTuberin nucleic acid molecule as is described herein. Such pharmaceutical compositions include any of the cTuberin nucleic acid molecules or cTuberins described herein.

The pharmaceutical compositions described herein may be assessed for contamination by conventional methods and then formulated into a pharmaceutical composition intended for a suitable route of administration. Still other compositions containing a cTuberin nucleic acid molecule, EVs comprising a cTuberin nucleic acid molecule, or a rAAV comprising a cTuberin nucleic acid molecule, may be formulated similarly with a suitable carrier. Such formulation involves the use of a pharmaceutically and/or physiologically acceptable vehicle or carrier, particularly directed for administration to the target cell. In one embodiment, carriers suitable for administration to the target cells include buffered saline, an isotonic sodium chloride solution, or other buffers, e.g., HEPES, to maintain pH at appropriate physiological levels, and, optionally, other medicinal agents, pharmaceutical agents, stabilizing agents, buffers, carriers, adjuvants, diluents, etc.

Typically, the carrier is a liquid for injection. Exemplary physiologically acceptable carriers include sterile, pyrogen-free water and sterile, pyrogen-free, phosphate buffered saline. In one embodiment, the carrier is an isotonic sodium chloride solution. In other examples, the carrier is a balanced salt solution. Other carriers include Tween. If the virus is to be stored long-term, it may be frozen in the presence of glycerol or Tween20.

Compositions containing cTuberin nucleic acid molecules described herein may also include a surfactant. Useful surfactants, such as Pluronic F68 (Poloxamer 188, also known as LUTROL® F68) may be included as they prevent AAV from sticking to inert surfaces and thus ensure delivery of the desired dose. As an example, one illustrative composition designed for the treatment of the diseases or disorders caused by a mutation in TSC2, e.g., tuberous sclerosis complex, as described herein comprises a recombinant adeno-associated vector carrying a nucleic acid sequence encoding cTuberin as described herein, under the control of regulatory sequences which express the cTuberin nucleic acid molecule in a brain cell, a heart cell, a kidney cell, a skin cell, or a lung cell of a mammalian subject, and a pharmaceutically acceptable carrier. The carrier is isotonic sodium chloride solution and includes a surfactant Pluronic F68. In one embodiment, the cTuberin nucleic acid molecule is any of those described herein.

In yet another exemplary embodiment, the composition includes a recombinant AAV1 or AAV9 pseudotyped adeno-associated virus carrying a cTuberin nucleic acid molecule for replacement, the nucleic acid sequence under the control of promoter which directs expression of the cTuberin nucleic acid molecule in brain, heart, kidney, skin, or lung cells, wherein the composition is formulated with a carrier and additional components suitable for dermal administration or intravascular, intracerebroventricular, intracranial, or intrathecal injection. In still another embodiment, the composition or components for production or assembly of this composition, including carriers, rAAV particles, surfactants, and/or the components for generating the rAAV, as well as suitable laboratory hardware to prepare the composition, may be incorporated into a kit.

Additionally, provided herein are kits containing a first pharmaceutical composition including a cTuberin nucleic acid molecule and a second pharmaceutical composition including drugs used for the treatment of tuberous sclerosis complex including, for example, rapamycin and its analogues. In some embodiments, the kit includes instructions for mixing the two pharmaceutical compositions prior to administration.

VI. Methods

The compositions described above are useful in methods of treating diseases or disorders caused by a mutation in TSC2 by replacing a normal allele of TSC2. Such methods involve contacting a target TSC2 gene with a cTuberin nucleic acid molecule as described herein, under conditions in which the cTuberin nucleic acid molecule is delivered to a selected cell to correct expression of TSC2 in the target cell. Thus, the methods and compositions are used to treat the diseases or disorders caused by a mutation in the TSC2 associated with the specific mutations and/or gene expression.

In some embodiments, a cTuberin nucleic acid molecule, EVs including a cTuberin nucleic acid molecule, or a rAAV including a cTuberin nucleic acid molecule is administered to a brain cell, a heart cell, a kidney cell, a skin cell, or a lung cell. In some embodiments, a cTuberin nucleic acid molecule, EVs including a cTuberin nucleic acid molecule, or a rAAV including a cTuberin nucleic acid molecule is administered to the affected subject dermally, or by intravascular, intracerebroventricular, intracranial, or intrathecal injection.

In some embodiments, the methods include the administration of a cTuberin nucleic acid molecule, EVs including a cTuberin nucleic acid molecule, or a rAAV including a cTuberin nucleic acid molecule for treating a subject having a disorder associated with a mutation in TSC2, such as tuberous sclerosis complex. Such selection can be based on the genotype of the subject. In some embodiments, a disorder associated with TSC2 may be an autosomal dominant disorder. In some instances, the subject is homozygous or compound heterozygous for the mutation in TSC2. Methods of screening for and identifying particular mutations in TSC2 are known in the art.

Dosing and Combination Therapies

Standards methods of dosing are used herein. Further, dosing for treatment of a renal angiomyolipoma, a lymphangioleiomyomatosis (LAM), and a brain dysfunction, as well as administration to a brain cell, heart cell, kidney cell, skin cell, or lung cell, are described below. Also described are dosing methods for administration by dermal, intravascular, intracerebral, intraventricular, or intrathecal injection.

An effective concentration of a recombinant adeno-associated virus carrying a cTuberin nucleic acid molecule as described herein ranges between about $10^9$ and $10^{15}$ genome copies (gc) per kg of body weight of the subject (gc/kg). For example, the effective concentration ranges between $10^9$ and $10^{15}$ gc/kg, e.g., $10^9$, $10^{10}$, $10^{11}$, $10^{12}$, $10^{13}$, $10^{14}$, and $10^{15}$ gc/kg. In another example, the effective concentration ranges between $10^{10}$ and $10^{13}$ gc/kg, e.g., $10^{10}$, $10^{11}$, $10^{12}$, and $10^{13}$ gc/kg. Still other dosages in these ranges or in other units may be selected by the attending physician, taking into account the physical state of the subject being treated, including the age of the subject; the composition being administered, and the particular disorder; the targeted cell and the degree to which the disorder, if progressive, has developed.

Renal Angiomyolipoma

For example, a rAAV carrying a cTuberin nucleic acid molecule can be used to treat a patient with a renal angiomyolipoma. The rAAV can be administered to the patient according to any method, e.g., by intravascular injection, for example, into the renal artery or vein. The effective dosage of the rAAV for treatment of renal angiomyolipoma by intravascular injection is between $10^9$ and $10^{15}$ gc/kg. In one embodiment, the amount of rAAV administered to the patient is about $10^9$ gc/kg. In a further embodiment, the amount of rAAV administered to the patient is about $10^{10}$ gc/kg. In a further embodiment, the amount of rAAV administered to the patient is about $10^{11}$ gc/kg. In a further embodiment, the amount of rAAV administered to the patient is about $10^{12}$ gc/kg. In a further embodiment, the amount of rAAV administered to the patient is about $10^{13}$ gc/kg. In a further embodiment, the amount of rAAV administered to the patient is about $10^{14}$ gc/kg. In a further embodiment, the amount of rAAV administered to the patient is about $10^{15}$ gc/kg.

LAM

A rAAV carrying a cTuberin nucleic acid molecule can also be used to treat a patient with a lymphangioleiomyomatosis (LAM). The rAAV can be administered to the patient according to any method, e.g., by intravascular injection. The effective dosage of the rAAV for treatment of a LAM by intravascular injection is between $10^9$ and $10^{15}$ gc/kg. In one embodiment, the amount of rAAV administered to the patient is about $10^9$ gc/kg. In a further embodiment, the amount of rAAV administered to the patient is about $10^{10}$ gc/kg. In a further embodiment, the amount of rAAV administered to the patient is about $10^{11}$ gc/kg. In a further embodiment, the amount of rAAV administered to the patient is about $10^{12}$ gc/kg. In a further embodiment, the amount of rAAV administered to the patient is about $10^{13}$ gc/kg. In a further embodiment, the amount of rAAV administered to the patient is about $10^{14}$ gc/kg. In a further embodiment, the amount of rAAV administered to the patient is about $10^{15}$ gc/kg. Further, the rAAV can administered to a patient with a LAM via a nasal route or other medically approved route into the lungs.

Brain Dysfunction

In another example, a rAAV carrying a cTuberin nucleic acid molecule can be used to a patient with a brain dysfunction. The rAAV can be administered to the patient according to any method, e.g., by intravascular, intracerebroventricular, intracranial, or intrathecal injection.

For treatment of a brain dysfunction by intravascular injection, the effective dosage of the rAAV is between $10^9$ and $10^{15}$ gc/kg. In one embodiment, the amount of rAAV administered to the patient is about $10^9$ gc/kg. In a further embodiment, the amount of rAAV administered to the patient is about $10^{10}$ gc/kg. In a further embodiment, the amount of rAAV administered to the patient is about $10^{11}$ gc/kg. In a further embodiment, the amount of rAAV administered to the patient is about $10^{12}$ gc/kg. In a further embodiment, the amount of rAAV administered to the patient is about $10^{13}$ gc/kg. In a further embodiment, the amount of rAAV administered to the patient is about $10^{14}$ gc/kg. In a further embodiment, the amount of rAAV administered to the patient is about $10^{15}$ gc/kg.

Further, for treatment of a brain dysfunction by intracerebroventricular injection, the effective dosage of the rAAV is between $10^{10}$ and $10^{13}$ gc/kg. In one embodiment, the amount of rAAV administered to the patient is about $10^{10}$ gc/kg. In a further embodiment, the amount of rAAV administered to the patient is about $10^{11}$ gc/kg. In a further embodiment, the amount of rAAV administered to the patient is about $10^{12}$ gc/kg. In a further embodiment, the amount of rAAV administered to the patient is about $10^{13}$ gc/kg.

Further, for treatment of a brain dysfunction by intracranial injection, the effective dosage of the rAAV is between $10^{10}$ and $10^{13}$ gc/kg. In one embodiment, the amount of rAAV administered to the patient is about $10^{10}$ gc/kg. In a further embodiment, the amount of rAAV administered to the patient is about $10^{11}$ gc/kg. In a further embodiment, the amount of rAAV administered to the patient is about $10^{12}$ gc/kg. In a further embodiment, the amount of rAAV administered to the patient is about $10^{13}$ gc/kg.

Further, for treatment of a brain dysfunction by intrathecal injection, the effective dosage of the rAAV is between $10^{10}$ and $10^{13}$ gc/kg. In one embodiment, the amount of rAAV administered to the patient is about $10^{10}$ gc/kg. In a further embodiment, the amount of rAAV administered to the patient is about $10^{11}$ gc/kg. In a further embodiment, the amount of rAAV administered to the patient is about $10^{12}$ gc/kg. In a further embodiment, the amount of rAAV administered to the patient is about $10^{13}$ gc/kg.

Delivery

The composition may be delivered in a volume of from about 50 µL to about 1 mL, including all numbers within the range, depending on the size of the area to be treated, the viral titer used, the route of administration, and the desired effect of the method. In one embodiment, the volume is about 50 µL. In another embodiment, the volume is about 70 µL. In another embodiment, the volume is about 100 µL. In another embodiment, the volume is about 125 µL. In another embodiment, the volume is about 150 µL. In another embodiment, the volume is about 175 µL. In yet another embodiment, the volume is about 200 µL. In another embodiment, the volume is about 250 µL. In another embodiment, the volume is about 300 µL. In another embodiment, the volume is about 350 µL. In another embodiment, the volume is about 400 µL In another embodiment, the volume is about 450 µL. In another embodiment, the volume is about 500 µL. In another embodiment, the volume is about 600 µL. In another embodiment, the volume is about 750 µL. In another embodiment, the volume is about 850 µL. In another embodiment, the volume is about 1,000 µL.

In one embodiment, the volume and concentration of the rAAV composition is selected so that only certain anatomical regions having target cells are impacted. In another embodiment, the volume and/or concentration of the rAAV composition is a greater amount, in order reach larger portions of the targeted organ, e.g., brain, heart, kidney, skin, or lung. Similarly dosages are adjusted for administration to other organs.

Provided herein are methods to treat tuberous sclerosis complex in a patient. In some embodiments, the invention provides a method to treat a renal angiomyolipoma, a LAM, or a brain dysfunction a subject. For each of the described methods, the treatment may be used to prevent the occurrence of further damage or to rescue tissue having mild or advanced disease. As used herein, the term "rescue" means to prevent progression of the disease, prevent spread of damage to uninjured cells or to improve damage in injured cells.

Thus, in one embodiment, the composition is administered before disease onset. In another embodiment, the composition is administered prior to the development of symptoms. In another embodiment, the composition is administered after development of symptoms. In yet another embodiment, the composition is administered when less than 90% of the target cells are functioning or remaining, e.g., as compared to a reference tissue. In yet another embodiment, the composition is administered when more than 10% of the target cells are functioning or remaining, e.g., as compared to a reference tissue. In yet another embodiment, the composition is administered when more than 20% of the target cells are functioning or remaining. In yet another embodiment, the composition is administered when more than 30% of the target cells are functioning or remaining.

In yet another embodiment, any of the above described methods is performed in combination with another, or secondary, therapy. The therapy may be any now known, or as yet unknown, therapy which helps prevent, arrest or ameliorate these mutations or defects or any of the effects associated therewith. The secondary therapy can be administered before, concurrently with, or after administration of the cTuberin nucleic acid molecule or rAAV carrying a cTuberin nucleic acid molecule as described above. In one embodiment, a secondary therapy involves the treatment of seizures in the subject, including, for example, the administration of an anti-seizure drug. In a further embodiment, the secondary therapy involves the administration of rapamycin. In a further embodiment, the secondary therapy involves co-administration with rapamycin. The administration or co-administration of rapamycin can be to a subject having tuberous sclerosis complex. Further, the administration or co-administration of rapamycin can be to a subject having a renal angiomyolipoma, a LAM, or a brain dysfunction. In some embodiments, the administration or co-administration of rapamycin can be during early childhood at the time of infantile seizures. In further embodiments, the administration or co-administration of rapamycin can be after detection of subependymal overgrowths by, for example, MRI. In further embodiments, the administration or co-administration of rapamycin can be any time later in life due to symptoms caused by overgrowths due to somatic loss of tuberin function.

For use in these methods, the volume and viral titer of each injection is determined individually. The dosages, administrations, and regimens may be determined by the attending physician given the teachings of this disclosure.

EXAMPLES

The following are examples of the methods and compositions of the invention. It is understood that various other embodiments may be practiced, given the general description provided above.

Example 1. Cell Culture

Tsc2-null mouse embryonic fibroblasts (MEFs) (Huang et al., *Biochem. J.* 412(2):179-190 2008) and immortalized TR1102 human angiomyolipoma cells (Hong et al., *Mol. Cell.* 30:701-711, 2008; Yu et al., *Am. J. Physiol. Lung Cell. Mol. Physiol.* 286:L694-L700, 2004) were grown in Dulbecco's Modified Eagle's medium (DMEM) (Cellgro®, Manassas, VA) growth media, supplemented with 10% fetal bovine serum (FBS) (Sigma-Aldrich®, St. Louis, MO) and 1% penicillin/streptomycin (Cellgro®) and cells were maintained at 37° C. in a humidified atmosphere of 5% $CO_2$ and 95% air. Lentivirus vectors were generated using CSCW-IG, a self-inactivating lentiviral vector, which has a CMV promoter controlling expression of both transgene and GFP cDNAs separated by an IRES element (Sena-Esteves et al., *J. Virol. Methods.* 122(2):131-139, 2004). The cDNA-encoding Fluc (pGL3-basic; Promega®, Madison, WI) and monomeric red fluorescent protein (mCherry) (Rizzo et al., 2004) were amplified by PCR. Fluc sequences were inserted directly downstream of the CMV promoter at the Nhe I site and mCherry sequences were inserted in place of the GFP cDNA at Bsa I and Sal I sites, generating pCSCW-Fluc-IRES-mCherry. Lentivirus vectors were generated as described with a typical titer of $10^8$-$10^{10}$ transducing units (tu) per ml (Sena-Esteves et al., *J. Virol. Methods.* 122(2): 131-139, 2004). To confer stable expression of Fluc and mCherry on lymphangioleiomyomatosis (LAM) cells, they were infected with CSCW-Fluc-IRES-mCherry lentivirus at a multiplicity of infection (M.O.I) of 100, which gave >90% infectability (cell line termed as TSC2-LAM-FC). COS-7 cells were cultured in DMEM supplemented with 10% FBS and 1% penicillin/streptomycin and transfected with a plasmid vector containing cDNA for cTuberin (pAAV-CBA-cTuberin) using Lipofectamine™ 3000 (Thermo Fisher Scientific®, Waltham, MA).

Example 2. AAV Vector Design and Packaging

Figure 2C:
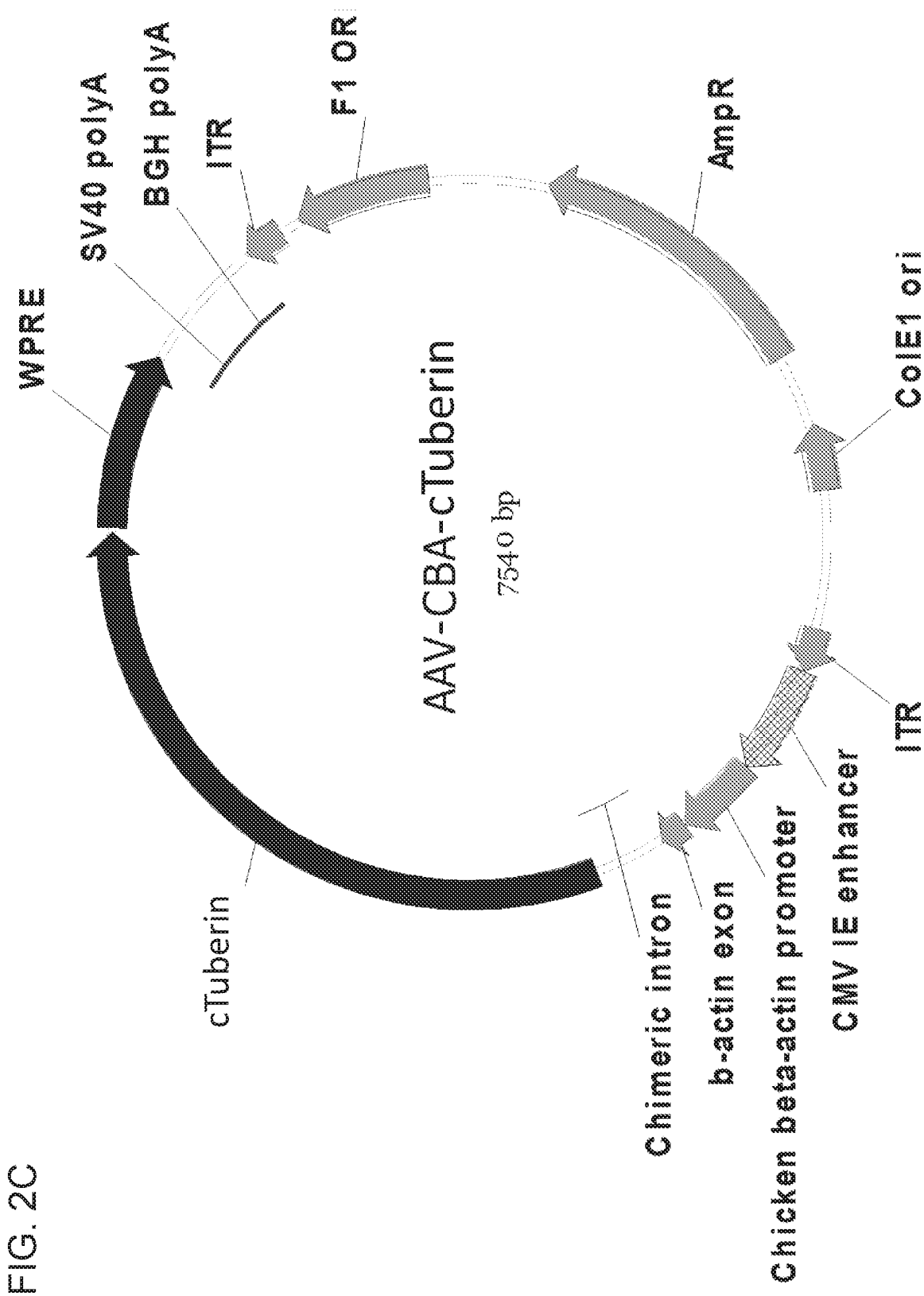
FIG. 2C is a schematic diagram of the AAV-CBA-cTuberin vector plasmid construct.

The AAV vector plasmid AAV-CBA-Cre-BGHpA was derived as described in Prabhakar et al., *PLoS One.* 8(5): e64224, 2013. These AAV vectors carry AAV2 ITR elements and gene expression is controlled by a hybrid promoter (chicken β-actin (CBA)) composed of the CMV immediate/early gene enhancer fused to the beta-actin promoter (Gray et al., *Hum. Gene Ther.* 22:1143-1153 2011). The AAV vector plasmid AAV-CBA-cTuberin was derived from the plasmid pAAV-CBA-W (CSCW-IG) (Sena-Esteves et al., *J. Virol. Methods.* 122(2):131-139, 2004). This vector contains the CBA promoter driving cTuberin, followed by a wood chuck hepatitis virus posttranscriptional regulatory element (WPRE) and SV40 and bovine growth hormone (BGH) polyadenylation (poly A) signal sequences (FIG. 2C). The condensed tuberin (cTuberin) construct contains: ACC (Kozak sequence)::amino acids 1-450 of human tuberin::gly/ser linker::amino acids 1515-1807 of human tuberin::cmyc tag. The 2,307 bp cDNA sequence encodes an 85 kDa protein (FIG. 1A).

AAV1 and AAV9 serotype vectors were produced by transient co-transfection of 293T cells by calcium phosphate precipitation of vector plasmids (AAV-CBA-cTuberin-cmyc), adenoviral helper plasmid pFΔ6, and a plasmid encoding AAV9 (pXR9) or AAV1 (pXR1) capsid genes, as previously described in Broekman et al., *Neuroscience.* 138:501-510, 2006. The identity of all PCR amplified sequences was confirmed by sequencing. Briefly, AAV vectors were purified by iodixanol density gradient centrifugation. The virus-containing fractions were concentrated using Amicon® Ultra 100 kDa MWCO centrifugal devices (EMD Millipore®, Billerica, MA) and the titer (genome copies (gc)/ml) was determined by real-time PCR amplification with primers and probe specific for the bovine growth hormone polyadenylation signal.

Example 3. Western Blots

Briefly, cultured cells were lysed in lysis buffer (50 mM HEPES pH 8.0, 150 mM NaCl, 2 mM EDTA, 2.5% sodium dodecyl sulfate, 2% CHAPS, 2.5 mM sucrose, 10% glycerol, 10 mM sodium fluoride, 2 mM sodium vanadate, 1 mM PMSF, 10 mM sodium pyrophosphate, protease inhibitor cocktail). After sonication and incubation at 8° C. for 10 min, the samples were centrifuged at 14,000 g for 30 min at 8° C. Equal amounts of protein, determined by detergent-compatible protein assay kit (Bio-Rad®, Hercules, CA), were boiled for 5 min in Laemmli sample buffer, separated by SDS-PAGE, and transferred onto nitrocellulose membranes (Bio-Rad®). The equal protein loading was confirmed by Ponceau S staining. The membranes were blocked in 2% blocking reagent (GE Healthcare, Pittsburgh, PA) for 1 h at room temperature and incubated with primary antibodies overnight at 4° C. Anti-Tuberin/TSC2 (#3612), anti-phospho-S6 (#2211), anti-S6 (#2212) (Cell Signaling Technology®), and anti-glyceraldehyde-3-phosphate dehydrogenase (GAPDH) (#2275-PC) (Trevigen®, Gaithersburg, MD) antibodies were used as primary antibodies. Anti-rabbit or anti-mouse IgG antibody conjugated with horseradish peroxidase was used as a secondary antibody. Enhanced chemiluminescence reagent, Lumigen® ECL Ultra (TMA-6) (Lumigen®, Southfield, MI) was used to detect the antigen-antibody complex.

Example 4. Animals and Intracerebroventricular (ICV) Injections

Experimental research protocols were approved by the Institutional Animal Care and Use Committee (IACUC) for the Massachusetts General Hospital (MGH) following the guidelines of the National Institutes of Health for the Care and Use of Laboratory Animals. Experiments were performed on $Tsc2^{c/c}$ floxed mice (Onda et al., *J. Clin. Invest.* 104(6):687-695, 1999). In response to Cre recombinase, the $Tsc2^{c/c}$ alleles are converted to null alleles, and the lacZallele expresses β-galactosidase. These mice have a normal, healthy lifespan.

For vector injections, on the day of birth (postnatal day 0 (P0)) or on P3, neonates were cryo-anesthetized and injected with 1 μl or 2 μl of viral vector AAV1-CBA-Cre into each cerebral lateral ventricle with a glass micropipette (70-100 mm diameter at the tip) using a Narishige® IM300 microinjector at a rate of 2.4 psi/sec (Narshige International, East Meadow, NY). Mice were then placed on a warming pad and returned to their mothers after regaining normal color and full activity typical of newborn mice.

Example 5. Retro-Orbital (RO) Injections

At 3 weeks of age (P21) mice were anesthetized by isoflurane inhalation (3.5% isoflurane in an induction chamber, then maintained anesthetized with 2-3% isoflurane and 1-2 liter/min oxygen for the duration of the experiment). AAV vectors were injected retro-orbitally into the vasculature right behind one of the eyeballs in a volume of 70 μl of solution (10 μl of AAV1- or AAV9-CBA-cTuberin+60 μl saline) or non-injected using a 0.3 ml insulin syringe over less than 2 min (Yardeni et al., *Lab. Anim. (NY).* 40(5):155-160, 2011).

Example 6. Subcutaneous Lymphangioleiomyomatosis (LAM) Model

Three million human TSC2 null, immortalized angiomyolipoma cells expressing Fluc were suspended in 50 µl reduced serum media (Opti-MEM®, Gibco®), mixed with 50 µl of Matrigel® (BD Matrigel™ Matrix HC) (BD Biosciences, Bedford, MA) and implanted subcutaneously in the backs of NOD-SCID Il2R gamma (NSG™) mice. After 4 weeks, mice were injected intraperitoneally with the Fluc substrate D-luciferin (LUCNA-1 G) (Gold Biotechnology®, St. Louis, MO), and a signal was acquired 5 min later with a high efficiency IVIS® Spectrum (Caliper Life Sciences, Hopkinton, MA) with an XGI-8 gas anesthesia system (Caliper Life Sciences).

Example 7. Histology and Immunohistochemistry (IHC)

Standard histology of mouse brains was carried out as described in Prabhakar et al., *PLoS One.* 8(5):e64224, 2013. Five µm sections were stained with Haematoxylin and Eosin (H&E) or used for IHC, as described (ibid.) using antibodies for pS6 (#2211, Cell Signaling), with secondary antibodies, as described (ibid.).

Example 8. Statistical Analysis

All analyses of survival curves (chi-squared test) were performed using GraphPad Prism software (GraphPad Software, Inc., La Jolla, CA). The P-values depicted are statistically significant.

Figure 3A:
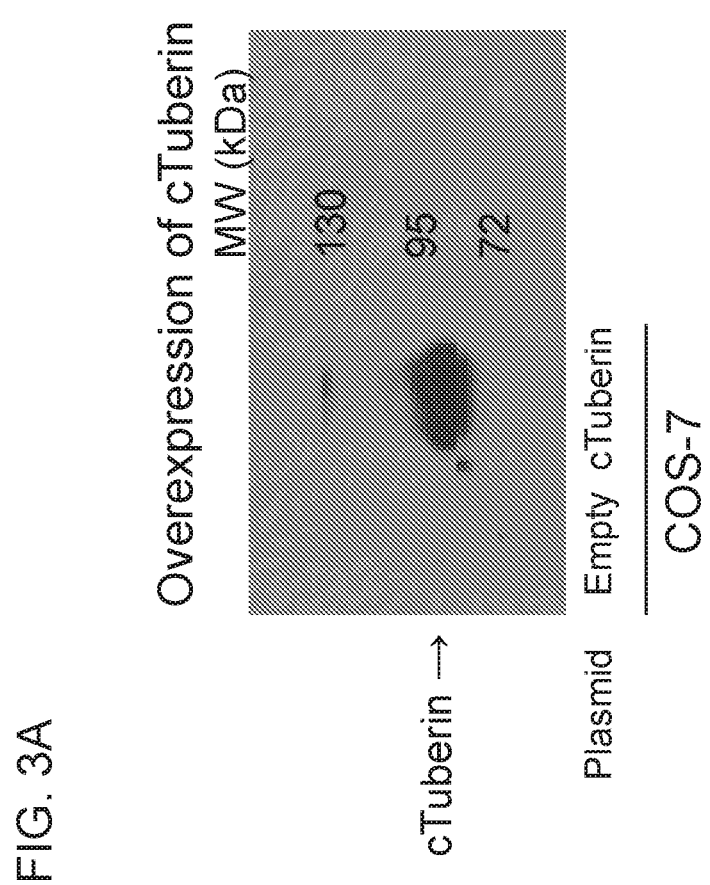
FIG. 3A is a Western blot showing the expression level of cTuberin in COS-7 cells transfected with the AAV-CBA-cTuberin vector plasmid construct. A band appears at the predicted molecular weight for cTuberin of approximately 85 kDa.

Example 9. Expression of cTuberin in COS-7 Cells Transfected with AAV-CBA-cTuberin Vector Plasmid COS-7 cells were transfected according to the procedure in Example 1 with the AAV-CBA-cTuberin vector plasmid of Example 2. After 24 hours, expression of cTuberin was detected by Western blotting as described in the preceding examples with anti-Tuberin/TSC2 antibody. Expression of cTuberin was apparent at the expected molecular weight (MW) of 85 kDa, as shown in FIG. 3A.

Example 10. pS6 Kinase Activity in COS-7 Cells Transfected with Various AAV Constructs To test the activity of cTuberin, COS-7 cells were transfected with GFP, pAAV-CBA-cTSC2, TSC2-FLAG, pAAV-CBA-cTSC2+TSC1-FLAG, TSC1-FLAG+TSC2-FLAG, and TSC1-FLAG vectors. Expression levels of phosphorylated S6 (pS6), S6, and GAPDH were detected by Western blotting. While pS6 kinase levels are normally elevated in the absence of tuberin activity, cells transfected with the AAV-CBA-cTuberin plasmid showed lower pS6 levels, indicating decreased pS6 kinase activity. This is shown in FIG. 3B, where pS6 levels are elevated in columns 1 (GFP (control)) and 7 (control, no plasmid) as compared to the other cells.

Figure 4A:
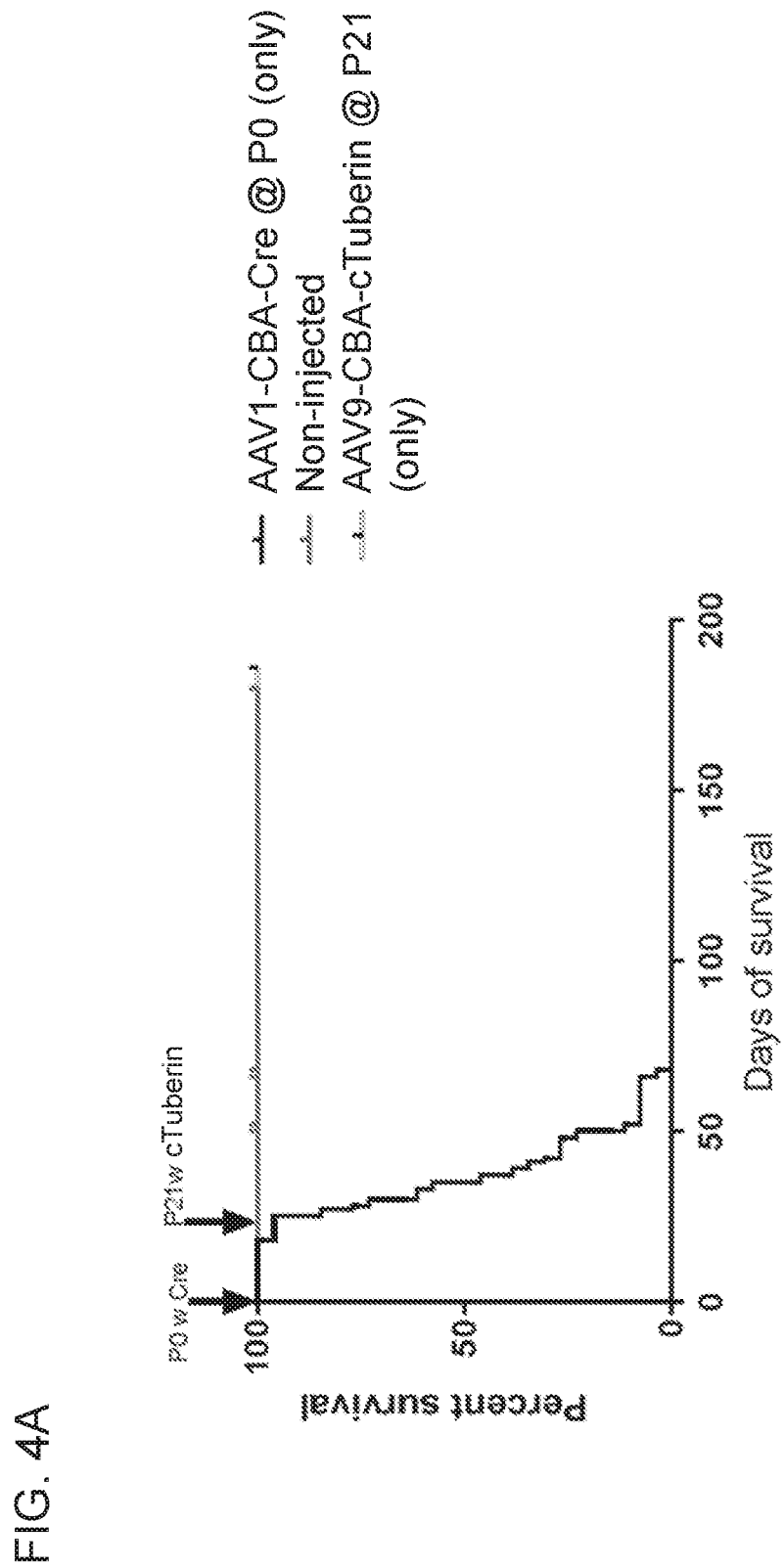
FIG. 4A is a graph showing the survival of Tsc2$^{c/c}$ mice injected with AAV1-CBA-Cre vector at birth (postnatal day 0 (P0)), Tsc2$^{c/c}$ mice injected with AAV9-CBA-cTuberin at P21, and non-injected mice. The median lifespan of the AAV1-CBA-Cre injected mice was 35 days, while the median lifespan was >185 days for the AAV9-CBA-cTuberin injected mice and >175 days for the non-injected mice.

Example 11. Survival of Mice Injected P0 with AAV1-CBA-Cre Vector, Mice Injected P21 with AAV9-CBA-cTuberin Vector, and Non-Injected Mice The efficacy of the AAV-CBA-cTuberin vector was tested on Tsc2$^{c/c}$ mice. Intraceroboventricular (ICV) and retroorbital (RO) injections were carried out as described in the preceding examples. AAV1-CBA-Cre and AAV9-CBA-cTuberin vectors were prepared as described above. Mice were injected ICV at P0 with AAV1-CBA-Cre (N=16), injected RO at P21 with AAV9-CBA-cTuberin (N=7), or non-injected (N=6). The titers of the AAV1-CBA-Cre and AAV9-CBA-cTuberin injections were $9.1 \times 10^{12}$ g.c./ml and $4.5 \times 10^{12}$ g.c./ml, respectively. The median survival was 35 days for the AAV1-CBA-Cre mice, >175 days for the non-injected mice, and >185 days for the AAV9-CBA-cTuberin mice. The difference between the groups was P<0.0001 (log-rank) or P<0.0001 (Gehan-Breslow-Wilcoxon), both statistically significant. Survival curves are depicted in FIG. 4A.

Figure 4B:
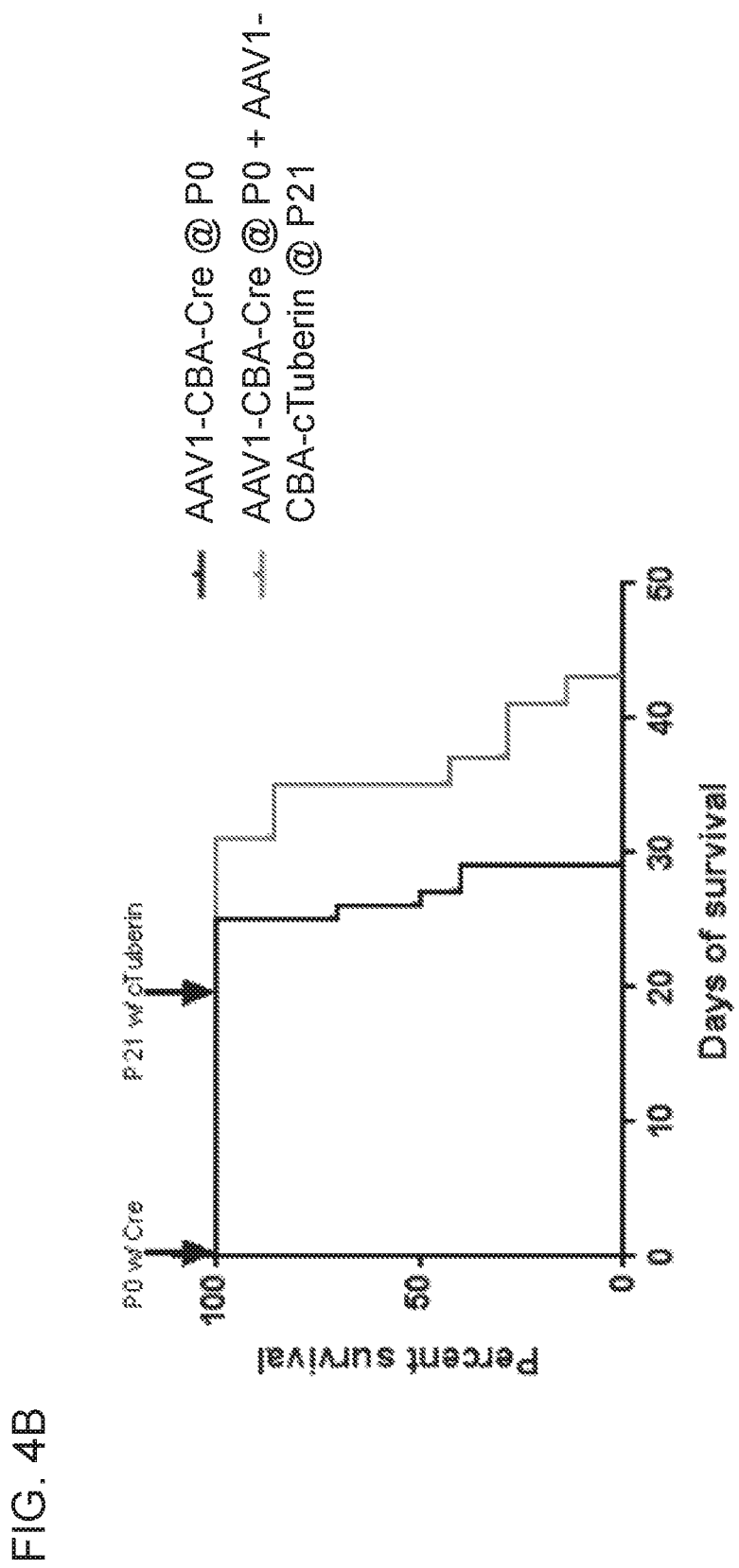
FIG. 4B is a graph showing the survival of Tsc2$^{c/c}$ mice injected with AAV1-CBA-Cre vector at P0 and mice injected with AAV1-CBA-Cre vector at P0 followed by injection with AAV1-CBA-cTuberin vector at P21. The median lifespan was 26.5 days for the non-injected mice and 35 days for the AAV1-CBA-cTuberin injected mice.

Example 12. Survival and Histology of Mice Injected P0 with AAV1-CBA-Cre Vector+P21 with AAV1-CBA-cTuberin Vector The efficacy of gene therapy with the AAV1-CBA-cTuberin vector was tested on mice lacking tuberin. The AAV1-CBA-cTuberin vector was prepared as described in the preceding examples. All mice were injected ICV at P0 with AAV1-CBA-Cre. At P21, one group of mice was injected RO with AAV1-CBA-cTuberin (N=7), while a second group was non-injected (N=10). The titers of the AAV1-CBA-Cre and AAV1-CBA-cTuberin injections were $5.1 \times 10^{13}$ g.c./ml and $3 \times 10^{11}$ g.c./ml, respectively. The median survival of the non-injected mice was 26.5 days, while the AAV1-CBA-cTuberin injected mice survived for a median of 35 days. The difference between the two groups was P=0.0001 (log-rank) or P=0.0004 (Gehan-Breslow-Wilcoxon), both statistically significant. Survival curves are depicted in FIG. 4B.

Figure 5A:
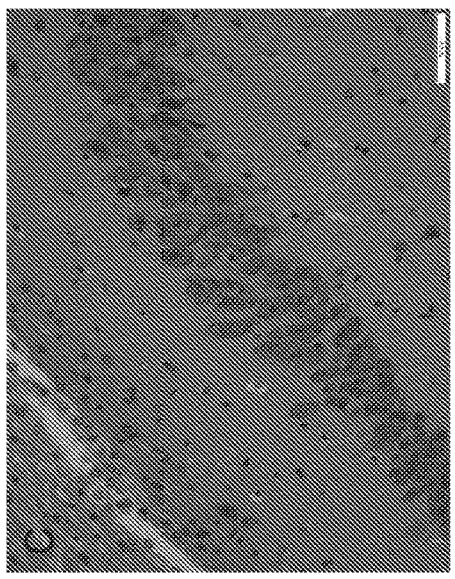
FIGS. 5A-5F shows the staining of mice brains treated according to the experimental design of FIG. 4B using Hematoxylin and Eosin (H&E) staining or immunohistochemistry (IHC) for pS6.
Figure 5B:
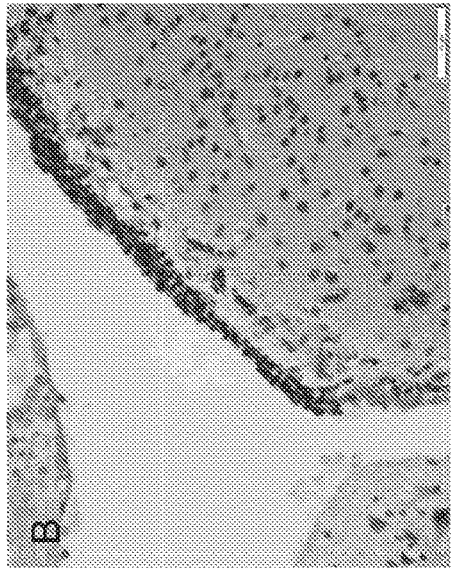
Figure 5C:
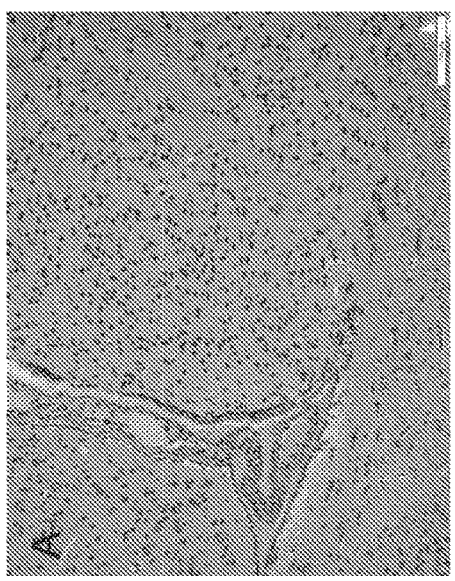
Figure 5D:
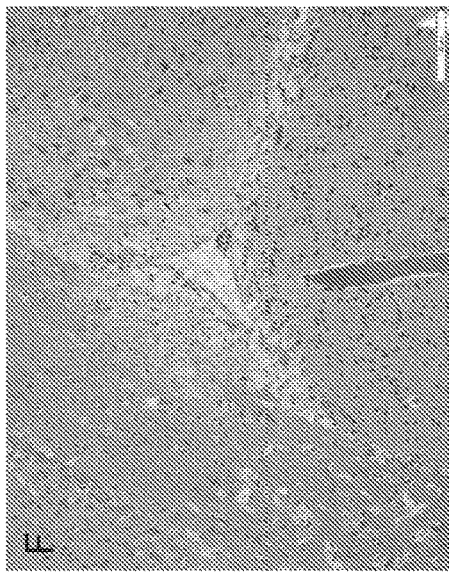
Figure 5E:
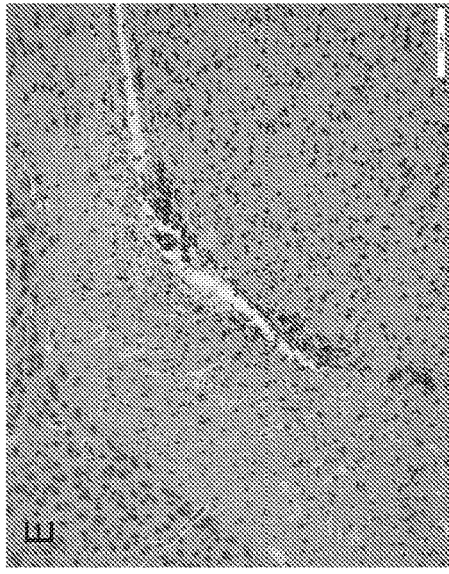
Figure 5F:
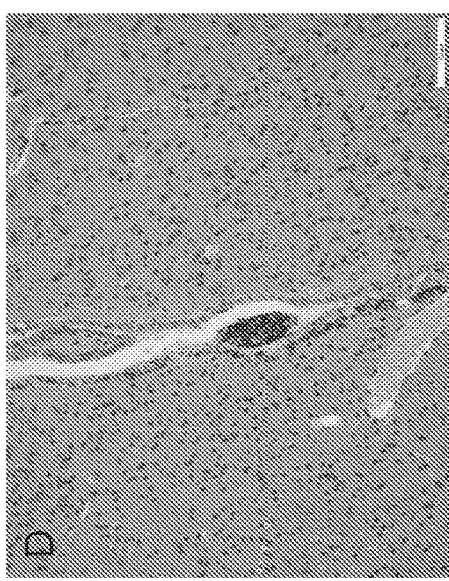

Additionally, the brains of the tuberin-lacking mice and AAV-CBA-cTuberin treated mice were studied using H&E staining or IHC for pS6 performed as described in Example 7. Tsc2$^{c/c}$ mice were injected at P0 with AAV1-CBA-Cre and at P21 AAV1-CBA-cTuberin according to the same design of the preceding experiment, then sacrificed at P27. Results are shown in FIGS. 5A-5F. FIG. 5A shows the staining in a normal, non-injected brain (control). FIGS. 5B-5E show the staining in a mouse injected only with AAV1-CBA-Cre at P0, showing proliferation of ependymal cells (FIG. 5B), enlarged pyramidal cell in the hippocampus (FIG. 5C), a subependymal nodule (FIG. 5D), and multiple subependymal nodules and proliferation (FIG. 5E). Finally, in the mouse treated with AAV1-CBA-cTuberin at P21, FIG. 5F shows a very small nodule, inflammation, and edema in the subependymal region.

Example 13. Survival of Mice Injected P3 with AAV1-CBA-Cre Vector+P21 with AAV1- or AAV9-CBA-cTuberin Vectors The efficacy of gene therapy with either AAV1-CBA-cTuberin vector or AAV9-CBA-cTuberin vector was further tested in the following two experiments. Mice were initially injected at P3 instead of P0 with AAV1-CBA-Cre when the cerebral spinal fluid (CSF) barrier is somewhat less penetrable than at P0, which should cause less loss of tuberin in the brain.

AAV1-CBA-cTuberin

Figure 4C:
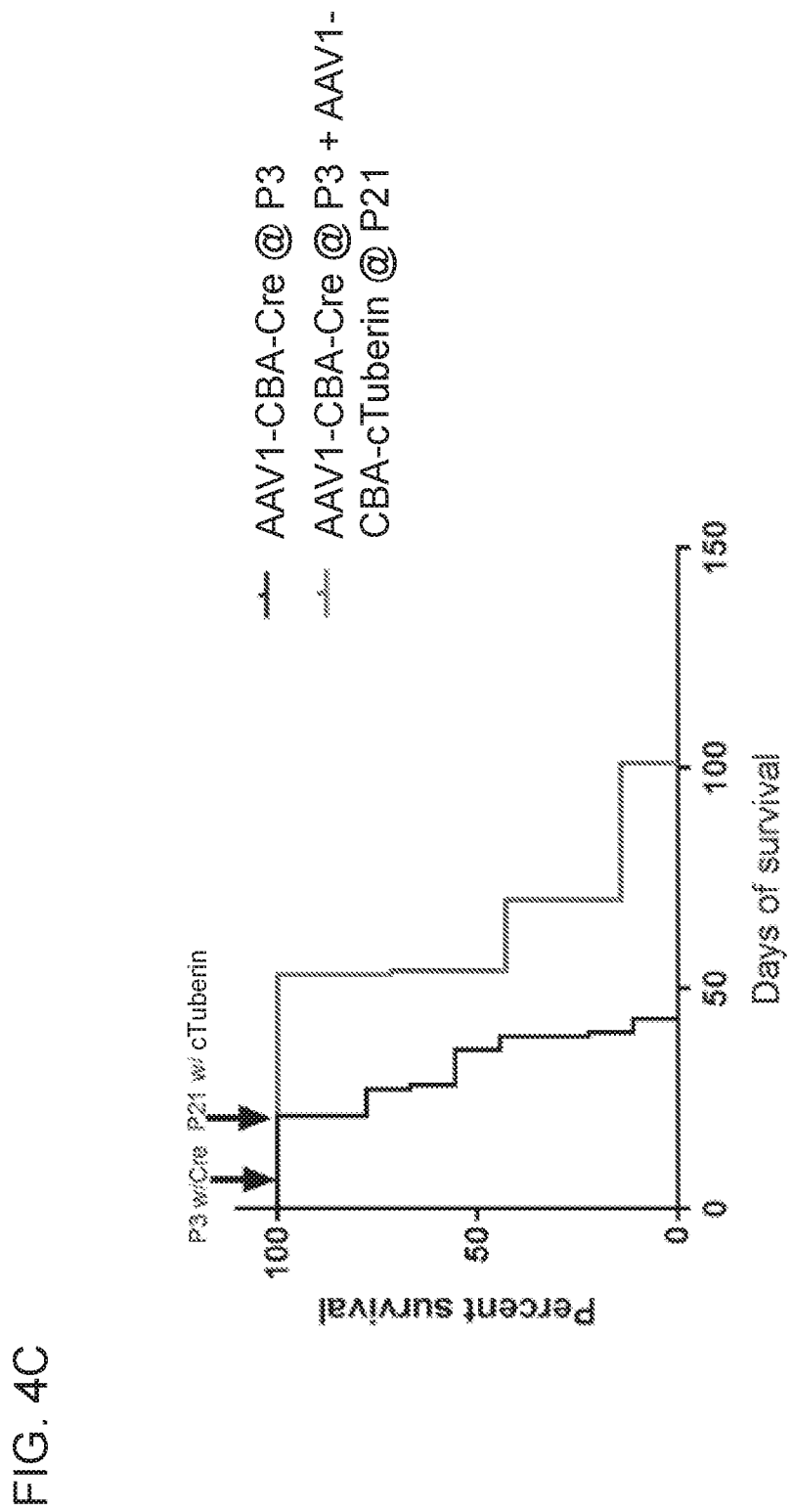
FIG. 4C is a graph showing the survival of Tsc2$^{c/c}$ mice injected with AAV1-CBA-Cre vector at P3 and mice injected with AAV1-CBA-Cre vector at P3 followed by injection with AAV1-CBA-cTuberin vector at P21. The median lifespan was 36 days for the non-injected mice and 54 days for the AAV1-CBA-cTuberin injected mice.

All Tsc2$^{c/c}$ mice were injected ICV at P3 with AAV1-CBA-Cre. At P21, one group of mice was injected RO with AAV1-CBA-cTuberin (N=9), while a second group was non-injected (N=7). The titers of the AAV1-CBA-Cre and AAV1-CBA-cTuberin injections were $5.1 \times 10^{13}$ g.c./ml and $3 \times 10^{11}$ g.c./ml, respectively. The median survival of the non-injected mice was 36 days, while the AAV1-CBA-cTuberin injected mice survived for a median of 54 days. The difference between the two groups was P<0.0001 (log-rank) or P=0.0004 (Gehan-Breslow-Wilcoxon), both statistically significant. Survival curves are depicted in FIG. 4C.

AAV9-CBA-cTuberin

Figure 4D:
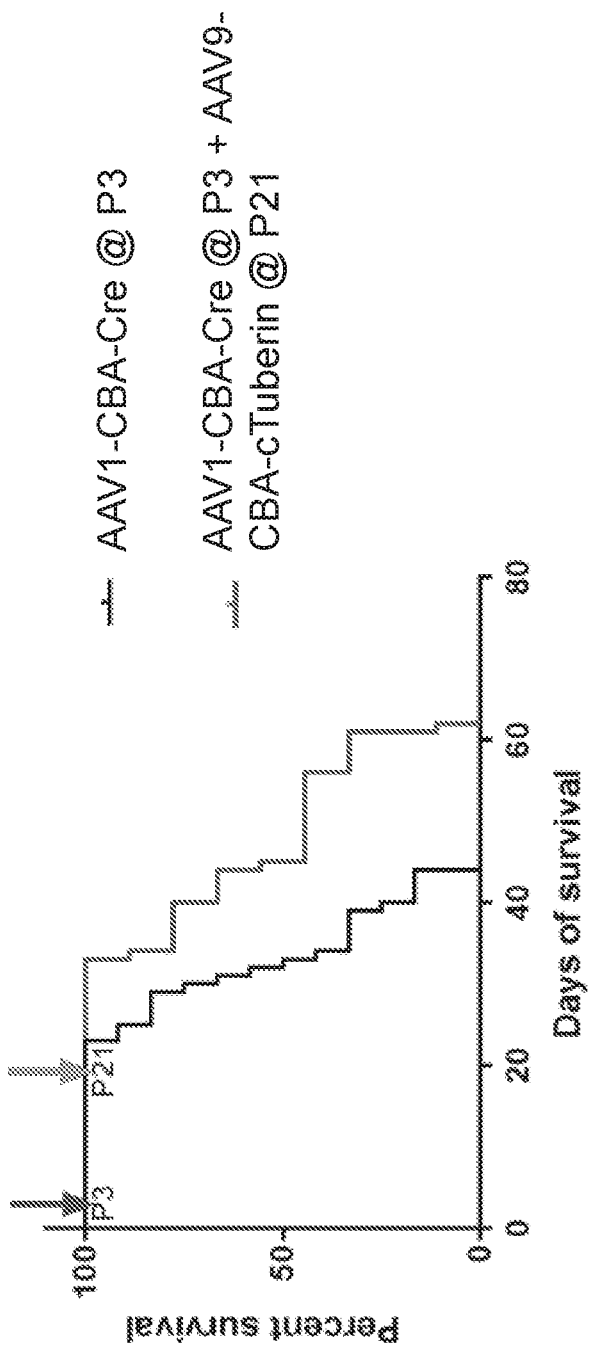
FIG. 4D is a graph showing the survival of Tsc2$^{c/c}$ mice injected with AAV1-CBA-Cre vector at P3 and mice injected with AAV1-CBA-Cre vector at P3 followed by injection with AAV9-CBA-cTuberin vector at P21. The median lifespan was 32 days for the non-injected mice and 45 days for the AAV9-CBA-cTuberin injected mice.
Figure 4E:
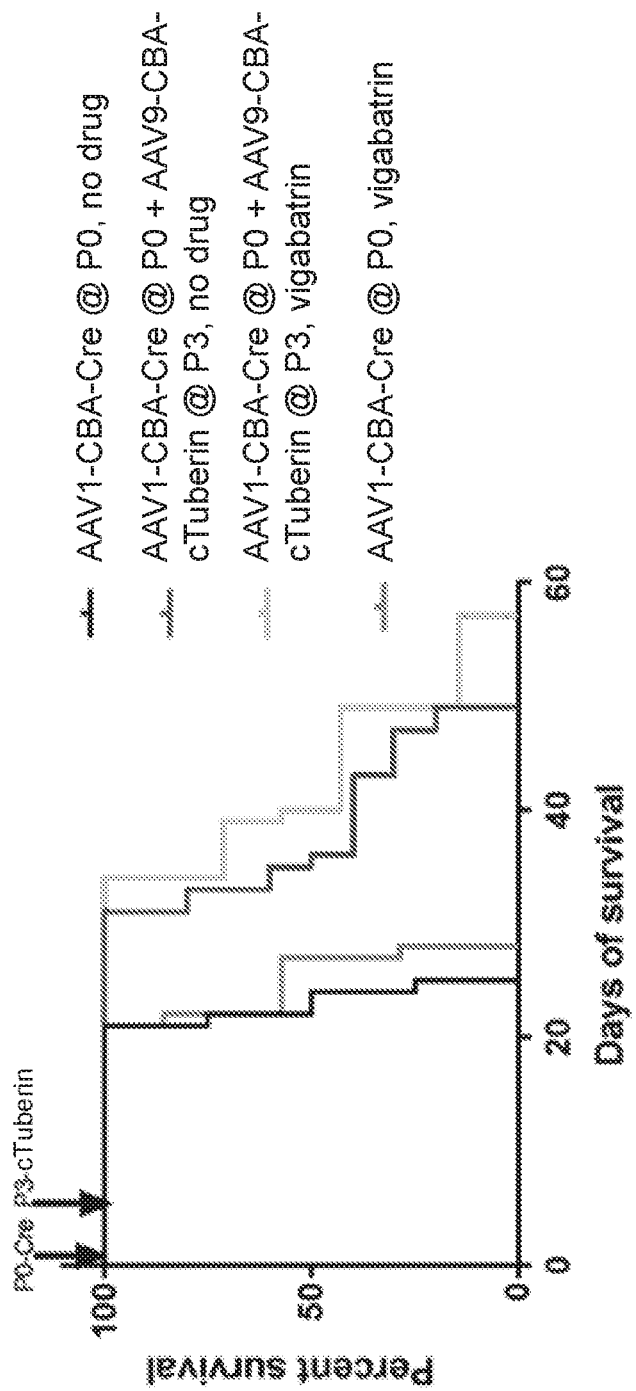
FIG. 4E is a graph showing the survival of four groups of Tsc2$^{c/c}$ mice. The first group was injected with AAV1-CBA-Cre vector at P0 only; the second group was injected with AAV1-CBA-Cre vector at P0 followed by injection with AAV9-CBA-cTuberin at P3; the third group mice was injected with AAV1-CBA-Cre vector at P0 only and treated with vigabatrin; and the fourth group was injected with AAV1-CBA-Cre vector at P0 followed by injection with AAV9-CBA-cTuberin at P3 and treated with vigabatrin. The median lifespan of non-injected, no drug mice was 23 days; of non-injected, vigabatrin-treated mice was 27 days; of injected, no drug mice was 35.5 days; and injected, vigabatrin-treated mice was 40 days.

All Tsc2$^{c/c}$ mice were injected ICV at P3 with AAV1-CBA-Cre. At P21, one group of mice was injected RO with AAV9-CBA-cTuberin (N=11), while a second group was non-injected (N=9). The titers of the AAV1-CBA-Cre and AAV9-CBA-cTuberin injections were $5.1 \times 10^{13}$ g.c./ml and $4.5 \times 10^{12}$ g.c./ml, respectively. The median survival of the non-injected mice was 32 days, while the AAV9-CBA-cTuberin injected mice survived for a median of 45 days. The difference between the two groups was P<0.0006 (log-rank) or P=0.0014 (Gehan-Breslow-Wilcoxon), both statistically significant. Survival curves are depicted in FIG. 4D.

Example 14. Survival of Mice Injected with AAV9-CBA-cTuberin Vector and Vigabatrin It is possible that the therapeutic vector will also decrease seizures. If not, seizures may be the cause of early death, i.e., death prior to hydrocephalus produced by subependymal nodules (SENs). The efficacy of AAV9-CBA-cTuberin was further tested in combination with vigabatrin, which is effective at blocking seizures in Tsc1-floxed/GFAP-Cre mice (Zhang et al., *PLoS One.* 8(2):e57445, 2013).

All mice were injected ICV at P0 with AAV1-CBA-Cre. One group of mice was injected RO at P3 with AAV9-CBA-cTuberin, while a second group was non-injected. Of the injected mice, one group was treated with vigabatrin (50 mg/kg) (N=7), while a second group was untreated (N=10). Of the non-injected mice, one group was treated with vigabatrin (200 mg/kg) (N=7), while a second group was untreated (N=8). The titers of the AAV1-CBA-Cre and AAV9-CBA-cTuberin were $5.1 \times 10^{13}$ g.c./ml and $4.5 \times 10^{12}$ g.c./ml, respectively. The dose of vigabatrin delivered was 50 mg/kg for the AAV9-CBA-cTuberin injected mice and 200 mg/kg for the non-injected mice. The median survival was 23 days for the non-injected, no drug mice; 27 days for the non-injected, vigabatrin-treated mice; 35.5 days for the injected, no drug mice; and 40 days for the injected, vigabatrin-treated mice. The difference between the two AAV9-CBA-cTuberin injected groups was P<0.0001 (log-rank) or P<0.0001 (Gehan-Breslow-Wilcoxon), both statistically significant.

Example 15. Efficacy of AAV9-CBA-cTuberin on LAM Tumors In Vivo

Figure 6A:
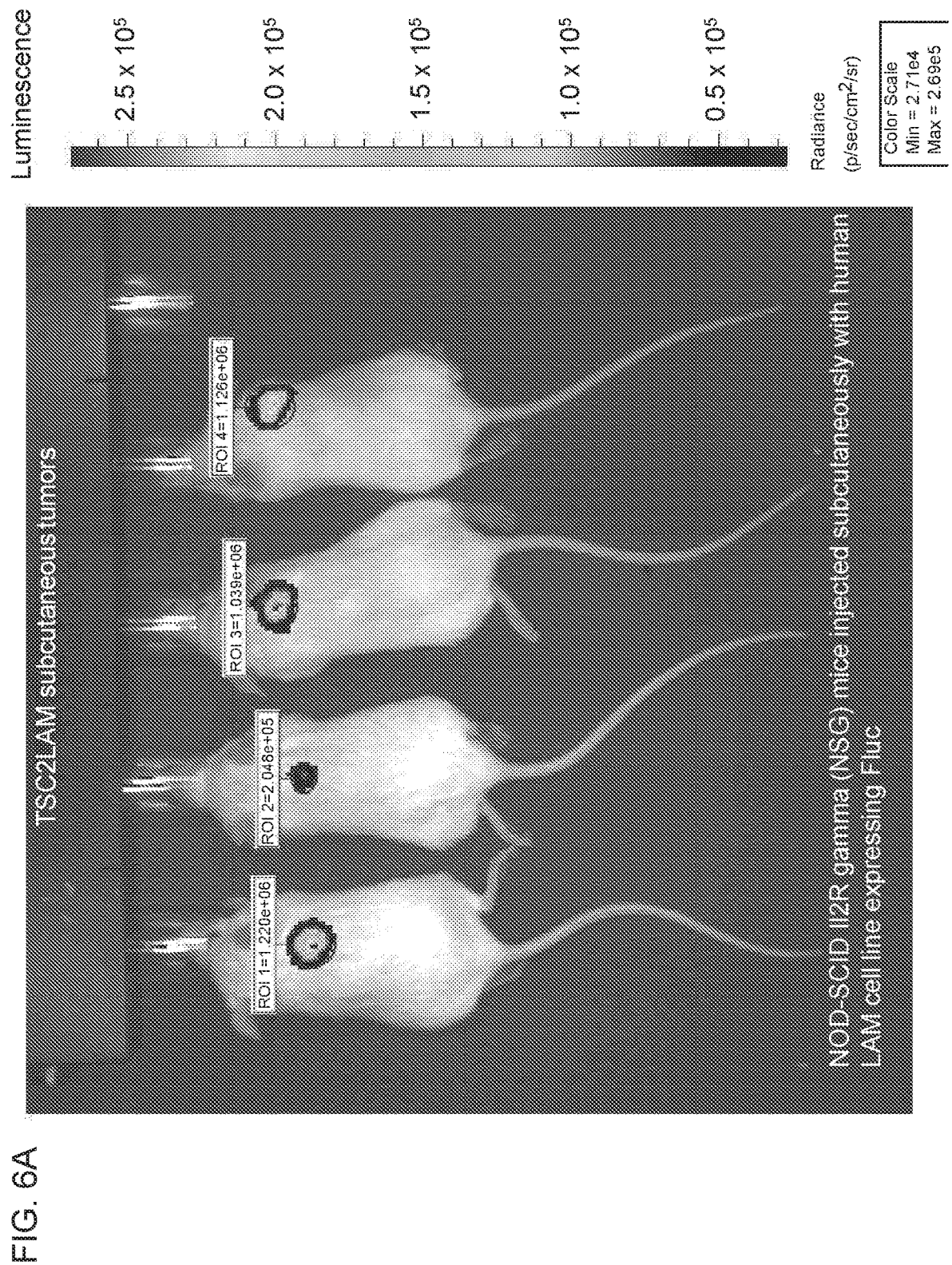
FIG. 6A shows the volumes of the lymphangioleiomyomatosis (LAM) tumors injected subcutaneously into NOD-SCID Il2R gamma (NSG) mice.

The efficacy of AAV9-CBA-cTuberin was also tested in vivo on lymphangioleiomyomatosis (LAM) tumors injected subcutaneously in immunocompromised NSG mice, which were prepared as described in Example 4. The Fluc-expressing LAM tumors are shown in FIG. 6A. Tumor volume was monitored via bioluminescence at weeks 1, 4, 6, 9 and 14. At weeks 4 and 9, tumors were either injected with AAV9-CBA-cTuberin vector (N=7) or non-injected (N=5). The titer of the AAV9-CBA-cTuberin vector was $4.3 \times 10^{10}$ g.c./ml. By week 14, tumors injected with the cTuberin vector had ceased increasing in size, while the non-injected tumors continued to expand in volume, as depicted in FIG. 6B.

OTHER EMBODIMENTS

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

---

What is claimed is:

1. A protein, comprising a hamartin binding region and a GTPase-activating protein (GAP) region, wherein said protein comprises: (i) a hamartin binding region having at least 94% sequence identity to SEQ ID NO: 2, (ii) a GTPase-activating protein (GAP) region having at least 93% sequence identity to SEQ ID NO: 3, and iii) a spacer sequence linking the hamartin binding region to the GAP region, wherein the spacer sequence comprises SGGG (SEQ ID NO: 13), and wherein said protein lacks amino acids 451-1514 of human tuberin (SEQ ID NO: 10).

2. The protein of claim 1, wherein said hamartin binding region is SEQ ID NO: 2.

3. The protein of claim 1, wherein said GAP region is SEQ ID NO: 3.

4. The protein of claim 1, wherein said spacer is SEQ ID NO: 4.

5. The protein of claim 1, wherein said protein has at least 92% sequence identity to SEQ ID NO: 1.

6. The protein of claim 1, wherein said protein is SEQ ID NO: 1.

7. A nucleic acid molecule encoding the protein of claim 1.

8. The nucleic acid molecule of claim 7, wherein said nucleic acid molecule is codon optimized for expression in a human cell.

9. The nucleic acid molecule of claim 8, wherein said nucleic acid molecule is operably linked to a regulatory control sequence.

10. The nucleic acid molecule of claim 7, wherein said nucleic acid molecule has at least 90% sequence identity to SEQ ID NO: 5.

11. An isolated cell comprising the nucleic acid molecule of claim 7.

12. A composition comprising the nucleic acid molecule claim 7.

13. A recombinant adeno-associated virus (rAAV), said rAAV comprising an AAV capsid and an AAV genome packaged therein, said AAV genome comprising a nucleic acid molecule capable of expressing a protein comprising a hamartin binding region and a GAP region, wherein said protein comprises: (i) a hamartin binding region having at least 94% sequence identity to SEQ ID NO: 2, (ii) a GTPase-activating protein (GAP) region having at least 93% sequence identity to SEQ ID NO: 3, and (iii) a spacer sequence linking the hamartin binding region to the GAP region, wherein the spacer sequence comprises SGGG (SEQ ID NO: 13), and wherein said protein lacks amino acids 451-1514 of human tuberin (SEQ ID NO: 10).

14. A composition comprising the rAAV of claim 13 and a pharmaceutically acceptable carrier.

15. A method of treating a patient having tuberous sclerosis complex (TSC), said method comprising administering to said patient a protein comprising a hamartin binding region and a GAP region, wherein said protein comprises: (i) a hamartin binding region having at least 94% sequence identity to SEQ ID NO: 2, (ii) a GTPase-activating protein (GAP) region having at least 93% sequence identity to SEQ ID NO: 3, and (iii) a spacer sequence linking the hamartin binding region to the GAP region, wherein the spacer sequence comprises SGGG (SEQ ID NO: 13), and wherein said protein lacks amino acids 451-1514 of human tuberin (SEQ ID NO: 10).

16. The method of claim 15, wherein said patient has a renal angiomyolipoma.

17. The method of claim 15, wherein said patient is further administered rapamycin.

18. A virus comprising the nucleic acid molecule of claim 7.

19. A method of treating a patient having tuberous sclerosis complex (TSC), said method comprising administering to said patient the rAAV of claim 13.

20. The method of claim 19, wherein said patient has a renal angiomyolipoma.

21. The method of claim 19, wherein said patient is further administered rapamycin.

* * * * *

UNITED STATES PATENT AND TRADEMARK OFFICE
CERTIFICATE OF CORRECTION

PATENT NO. : 11,958,887 B2
APPLICATION NO. : 16/613907
DATED : April 16, 2024
INVENTOR(S) : Xandra Breakefield et al.

It is certified that error appears in the above-identified patent and that said Letters Patent is hereby corrected as shown below:

In the Claims

Column 61, Claim 1, Line 34, replace "iii)" with --(iii)--.

Column 61, Claim 12, Line 63, replace "claim 7" with --of claim 7--.

Signed and Sealed this
Twenty-eighth Day of May, 2024

Katherine Kelly Vidal
*Director of the United States Patent and Trademark Office*